(12) United States Patent
Mathews et al.

(10) Patent No.: US 8,680,339 B2
(45) Date of Patent: Mar. 25, 2014

(54) HERBICIDES

(75) Inventors: Christopher John Mathews, Bracknell (GB); John Finney, Bracknell (GB); James Nicholas Scutt, Bracknell (GB); Louisa Robinson, Bracknell (GB); John Stephen Delaney, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 87 days.

(21) Appl. No.: 13/147,997

(22) PCT Filed: Jan. 25, 2010

(86) PCT No.: PCT/EP2010/050758
§ 371 (c)(1),
(2), (4) Date: Oct. 17, 2011

(87) PCT Pub. No.: WO2010/089210
PCT Pub. Date: Aug. 12, 2010

(65) Prior Publication Data
US 2012/0028800 A1    Feb. 2, 2012

(30) Foreign Application Priority Data
Feb. 4, 2009 (GB) .................................. 0901834.2

(51) Int. Cl.
| C07C 49/747 | (2006.01) |
| C07C 49/753 | (2006.01) |
| C07C 45/64 | (2006.01) |
| C07D 213/64 | (2006.01) |
| A01N 35/06 | (2006.01) |
| A01N 43/16 | (2006.01) |
| A01N 25/32 | (2006.01) |

(52) U.S. Cl.
USPC ........... 568/315; 565/330; 549/427; 549/459; 546/157; 546/282.7; 546/285; 548/187; 548/188; 504/118; 504/121; 504/124

(58) Field of Classification Search
USPC ........... 568/315, 330; 549/427, 459; 546/157, 546/282.7, 285; 548/187, 188, 364.4; 504/118, 121, 124
See application file for complete search history.

(56) References Cited

U.S. PATENT DOCUMENTS

| 4,175,135 A | 11/1979 | Haines |
| 4,209,532 A | 6/1980 | Wheeler |
| 4,283,348 A * | 8/1981 | Wheeler .................. 558/412 |
| 4,409,153 A | 10/1983 | Hodakowski |
| 4,489,012 A | 12/1984 | Hodakowski |
| 4,526,723 A | 7/1985 | Wheeler et al. |
| 4,659,372 A | 4/1987 | Wheeler |
| 5,801,120 A | 9/1998 | Lee et al. |
| 6,251,833 B1 | 6/2001 | Erdelen et al. |
| 6,458,965 B1 | 10/2002 | Lieb et al. |
| 6,894,005 B1 | 5/2005 | Maetzke et al. |
| 8,058,210 B2 | 11/2011 | Lieb et al. |
| 8,084,649 B2 | 12/2011 | Muehlebach et al. |
| 2003/0216260 A1 | 11/2003 | Ruther et al. |
| 2006/0166829 A1 | 7/2006 | Fischer et al. |
| 2010/0113270 A1 | 5/2010 | Mathews et al. |
| 2010/0210466 A1 | 8/2010 | Muehlebach et al. |
| 2010/0216638 A1 | 8/2010 | Mathews et al. |
| 2010/0279868 A1 | 11/2010 | Jeanmart et al. |
| 2010/0298140 A1 | 11/2010 | Jeanmart et al. |
| 2012/0021907 A1 | 1/2012 | Mathews et al. |
| 2012/0021909 A1 | 1/2012 | Mathews et al. |
| 2012/0021912 A1 | 1/2012 | Mathews et al. |
| 2012/0040826 A1 | 2/2012 | Jeanmart et al. |
| 2012/0094832 A1 | 4/2012 | Mathews et al. |
| 2012/0142529 A1 | 6/2012 | Tyte et al. |

FOREIGN PATENT DOCUMENTS

| CA | 2322158 A1 | 8/2000 |
| CA | 2325526 A1 | 9/2000 |
| CA | 2382432 A1 | 2/2002 |
| CA | 2382435 A1 | 2/2002 |
| CA | 2456776 A1 | 2/2004 |
| DE | 2813341 C2 | 4/1983 |
| WO | WO 92/16510 A1 | 10/1992 |
| WO | 9603366 | 2/1996 |
| WO | WO 96/11574 A1 | 4/1996 |
| WO | WO96/21652 A1 | 7/1996 |

(Continued)

OTHER PUBLICATIONS

Muehlebach et al., "Discovery and SAR of pinoxaden: a new broad spectrum, postemergence cereal herbicide," in Pesticide Chemistry. Crop Protection, Public Health, Environmental Safety, ed. H. Ohkawa et al., Jun. 2007, Wiley-VCH Verlag, Weinheim, pp. 101-110.

Wenger, J. and Nidermann, T., "Chapter 9: Acetyl-CoA Carboxylase Inhibitors", in Modern Crop Protection Compounds, ed. W. Kraemer et al., Wiley-VCH Verlag, Weinheim, 2007, pp. 335-357.

Wenger, et al., "Chapter 11: Acetyl-CoA Carboxylase Inhibitors", in Modern Crop Protection Compounds, Second Edition, ed. W. Kraemer et al., Wiley-VCH Verlag, Weinheim, available online Jan. 2012, pp. 447-477.

*Primary Examiner* — Sikarl Witherspoon
(74) *Attorney, Agent, or Firm* — R. Kody Jones

(57) ABSTRACT

Compounds of Formula (I), wherein the substituents are as defined in claim 1, are suitable for use as herbicides.

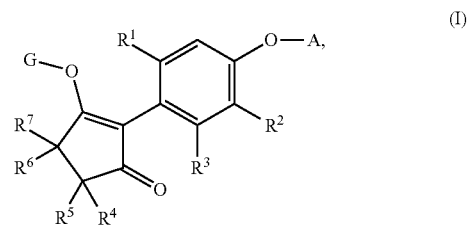

25 Claims, No Drawings

(56) References Cited

FOREIGN PATENT DOCUMENTS

| WO | 9839281 | | 9/1998 |
|---|---|---|---|
| WO | WO99/43649 | A1 | 9/1999 |
| WO | WO 99/47525 | A1 | 9/1999 |
| WO | WO99/48869 | A1 | 9/1999 |
| WO | WO 00/37437 | A1 | 6/2000 |
| WO | WO01/17972 | A2 | 3/2001 |
| WO | WO 01/17973 | A2 | 3/2001 |
| WO | WO01/74770 | A1 | 10/2001 |
| WO | WO03/013249 | A1 | 2/2003 |
| WO | WO98/39281 | A1 | 12/2004 |
| WO | WO2004/111042 | A1 | 12/2004 |
| WO | WO 2005/123667 | A1 | 12/2005 |
| WO | WO 2006/034315 | A2 | 3/2006 |
| WO | WO 2006/034446 | A2 | 3/2006 |
| WO | WO2008/071405 | A1 | 6/2008 |
| WO | WO2008/110307 | A1 | 9/2008 |
| WO | WO2008/110308 | A2 | 9/2008 |
| WO | WO2008/145336 | A1 | 12/2008 |
| WO | WO2009/000533 | A1 | 12/2008 |
| WO | WO2009/015877 | A1 | 2/2009 |
| WO | WO2009/019015 | A1 | 2/2009 |
| WO | WO2009/074314 | A1 | 6/2009 |
| WO | WO2010081755 | A1 | 7/2010 |
| WO | WO2010/089210 | A1 | 8/2010 |
| WO | WO2010/102848 | A1 | 9/2010 |

* cited by examiner

HERBICIDES

This application is a 371 of International Application No. PCT/EP2010/050758 filed Jan. 25, 2010, which claims priority to GB 0901834.2 filed Feb. 4, 2009, the contents of which are incorporated herein by reference.

The present invention relates to novel, herbicidally active cyclopentanediones, and derivatives thereof, to processes for their preparation, to compositions comprising those compounds, and to their use in controlling weeds, especially in crops of useful plants, or in inhibiting undesired plant growth.

Cyclopentanediones having herbicidal action are described, for example, in WO 01/74770, WO 96/03366 and U.S. Pat. No. 4,283,348.

Novel cyclopentanediones, and derivatives thereof, having herbicidal and growth-inhibiting properties have now been found.

The present invention accordingly relates to compounds of formula I

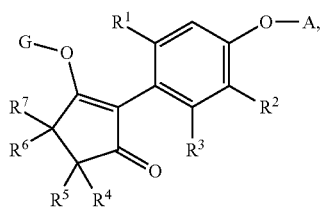

wherein
A is a mono- or bicyclic aryl or heteroaryl which contains a heteroatom selected from nitrogen, oxygen and sulfur, and which is unsubstituted or substituted,
$R^1$ is methyl, ethyl, n-propyl, isopropyl, cyclopropyl, halomethyl, haloethyl, vinyl, propenyl, ethynyl, propynyl, halogen, methoxy, ethoxy, halomethoxy or haloethoxy,
$R^2$ and $R^3$ are independently of each other hydrogen, methyl, ethyl, n-propyl, isopropyl, cyclopropyl, halomethyl, haloethyl, vinyl, propenyl, ethynyl, propynyl, halogen, methoxy, ethoxy, halomethoxy or haloethoxy,
$R^4$, $R^5$, $R^6$, and $R^7$ are independently of each other hydrogen, halogen, optionally substituted $C_1$-$C_6$alkyl, optionally substituted $C_3$-$C_7$cycloalkyl, optionally substituted $C_2$-$C_6$ alkenyl, optionally substituted $C_5$-$C_7$cycloalkenyl, optionally substituted $C_2$-$C_6$alkynyl, optionally substituted $C_1$-$C_6$ alkoxy, optionally substituted $C_3$-$C_7$cycloalkyloxy, optionally substituted $C_1$-$C_6$alkylthio, optionally substituted $C_1$-$C_6$alkylsulfinyl, optionally substituted $C_1$-$C_6$alkylsulfonyl, optionally substituted aryl, optionally substituted aryloxy, optionally substituted arylthio, optionally substituted arylsulfinyl, optionally substituted arylsulfonyl, optionally substituted heterocyclyl, optionally substituted heterocyclyloxy, optionally substituted heterocyclylthio, optionally substituted heterocyclylsulfinyl, optionally substituted heterocyclylsulfonyl, optionally substituted heteroaryl, optionally substituted heteroaryloxy, optionally substituted heteroarylthio, optionally substituted heteroarylsulfinyl, optionally substituted heteroarylsulfonyl, cyano or optionally substituted amino, or $R^4$ and $R^5$, or $R^6$ and $R^7$ together with the atoms to which they are bonded form an optionally substituted saturated or unsaturated carbocyclyl or heterocyclyl which contains one or two heteroatoms selected from nitrogen, oxygen or sulfur, or $R^5$ and $R^6$, together with the atoms to which they are bonded form an optionally substituted saturated or unsaturated carbocyclyl or heterocyclyl which contains one or two heteroatoms selected from nitrogen, oxygen or sulfur, and which carbocyclyl may further be bridged by optionally substituted $C_1$-$C_2$ alkyldiyl or by oxygen, and G is hydrogen or an agriculturally acceptable metal, sulfonium, ammonium or latentiating group.

In the substituent definitions of the compounds of the formula I, each alkyl moiety either alone or as part of a larger group (such as alkoxy, alkylthio, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, isopropyl, n-butyl, sec-butyl, isobutyl, tert-butyl or neopentyl. The alkyl groups are suitably $C_1$-$C_6$alkyl groups, but are preferably $C_1$-$C_4$alkyl or $C_1$-$C_3$alkyl groups, and, more preferably, $C_1$-$C_2$alkyl groups.

When present, the optional substituents on an alkyl moiety (alone or as part of a larger group such as alkoxy, alkoxycarbonyl, alkylcarbonyl, alkylaminocarbonyl, dialkylaminocarbonyl) include one or more of halogen, nitro, cyano, $C_3$-$C_7$cycloalkyl (itself optionally substituted with $C_1$-$C_6$alkyl or halogen), $C_5$-$C_7$cycloalkenyl (itself optionally substituted with $C_1$-$C_4$alkyl or halogen), hydroxy, $C_1$-$C_{10}$alkoxy, $C_1$-$C_{10}$alkoxy($C_1$-$C_{10}$)alkoxy, tri($C_1$-$C_4$)alkylsilyl($C_1$-$C_6$)alkoxy, $C_1$-$C_6$alkoxycarbonyl($C_1$-$C_{10}$)alkoxy, $C_1$-$C_{10}$haloalkoxy, aryl($C_1$-$C_4$)alkoxy (where the aryl group is optionally substituted), $C_3$-$C_7$cycloalkyloxy (where the cycloalkyl group is optionally substituted with $C_1$-$C_6$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio (where the aryl group is optionally substituted), $C_3$-$C_7$cycloalkylthio (where the cycloalkyl group is optionally substituted with $C_1$-$C_6$alkyl or halogen), tri($C_1$-$C_4$)alkylsilyl($C_1$-$C_6$)alkylthio, arylthio (where the aryl group is optionally substituted), $C_1$-$C_6$alkylsulfonyl, $C_1$-$C_6$haloalkylsulfonyl, $C_1$-$C_6$alkylsulfinyl, $C_1$-$C_6$haloalkylsulfinyl, arylsulfonyl (where the aryl group is optionally substituted), tri($C_1$-$C_4$)alkylsilyl, aryldi($C_1$-$C_4$)alkylsilyl, ($C_1$-$C_4$)alkyldiarylsilyl, triarylsilyl, aryl($C_1$-$C_4$)alkylthio($C_1$-$C_4$)alkyl, aryloxy($C_1$-$C_4$)alkyl, formyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$ alkyl)aminocarbonyl, N—($C_1$-$C_3$alkyl)-N—($C_1$-$C_3$ alkoxy)aminocarbonyl, $C_1$-$C_6$alkylcarbonyloxy, arylcarbonyloxy (where the aryl group is optionally substituted), di($C_1$-$C_6$)alkylaminocarbonyloxy, $C_1$-$C_6$alkyliminooxy, $C_3$-$C_6$alkenyloxyimino, aryloxyimino, aryl (itself optionally substituted), heteroaryl (itself optionally substituted), heterocyclyl (itself optionally substituted with $C_1$-$C_6$alkyl or halogen), aryloxy (where the aryl group is optionally substituted), heteroaryloxy, (where the heteroaryl group is optionally substituted), heterocyclyloxy (where the heterocyclyl group is optionally substituted with $C_1$-$C_6$alkyl or halogen), amino, $C_1$-$C_6$alkylamino, di($C_1$-$C_6$)alkylamino, $C_1$-$C_6$alkylcarbonylamino, N—($C_1$-$C_6$)alkylcarbonyl-N—($C_1$-$C_6$)alkylamino, $C_2$-$C_6$alkenylcarbonyl, $C_2$-$C_6$alkynylcarbonyl, $C_3$-$C_6$alkenyloxycarbonyl, $C_3$-$C_6$alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. It is understood, that allenyl and alkylinylalkenyl are included in these terms.

When present, the optional substituents on alkenyl or alkynyl include those optional substituents given above for an alkyl moiety.

Halogen is fluorine, chlorine, bromine or iodine.

Haloalkyl groups are alkyl groups which are substituted with one or more of the same or different halogen atoms and are, for example, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

In the context of the present specification the term "aryl" refers to ring systems which may be mono-, or bicyclic. Examples of such rings include phenyl and naphthyl. A preferred aryl group is phenyl.

The term "heteroaryl" preferably refers to an aromatic ring system containing at least one heteroatom and consisting either of a single ring or of two fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl.

The term "heterocyclyl" preferably refers to a non-aromatic preferably monocyclic or bicyclic ring systems containing up to 7 atoms including one or more (preferably one or two) heteroatoms selected from O, S and N. Examples of such rings include 1,3-dioxolane, oxetane, tetrahydrofuran, morpholine, thiomorpholin and piperazine. When present, the optional substituents on heterocyclyl include $C_1$-$C_6$alkyl and $C_1$-$C_6$haloalkyl as well as those optional substituents given above for an alkyl moiety.

Cycloalkyl includes preferably cyclopropyl, cyclobutyl, cyclopentyl and cyclohexyl. Cycloalkylalkyl is preferentially cyclopropylmethyl. Cycloalkenyl includes preferably cyclopentenyl and cyclohexenyl. When present, the optional substituents on cycloalkyl or cycloalkenyl include $C_1$-$C_3$alkyl as well as those optional substituents given above for an alkyl moiety.

Carbocyclic rings (carbocyclyl) include aryl, cycloalkyl or carbocyclic groups, and cycloalkenyl groups.

When present, the optional substituents on aryl, heteroaryl and carbocycles are preferably selected independently, from halogen, nitro, cyano, rhodano, isothiocyanato, $C_1$-$C_6$alkyl, $C_1$-$C_6$haloalkyl, $C_1$-$C_6$alkoxy($C_1$-$C_6$)alkyl, $C_2$-$C_6$alkenyl, $C_2$-$C_6$haloalkenyl, $C_2$-$C_6$alkynyl, $C_3$-$C_7$cycloalkyl (itself optionally substituted with $C_1$-$C_6$alkyl or halogen), $C_{5-7}$cycloalkenyl (itself optionally substituted with $C_1$-$C_6$alkyl or halogen), hydroxy, $C_1$-$C_{10}$alkoxy, $C_1$-$C_{10}$alkoxy($C_1$-$C_{10}$)alkoxy, tri($C_1$-$C_4$)alkylsilyl($C_1$-$C_6$)alkoxy, $C_1$-$C_6$alkoxycarbonyl($C_1$-$C_{10}$)alkoxy, $C_1$-$C_{10}$haloalkoxy, aryl($C_1$-$C_4$)alkoxy (where the aryl group is optionally substituted with halogen or $C_1$-$C_6$alkyl), $C_3$-$C_7$cycloalkyloxy (where the cycloalkyl group is optionally substituted with $C_1$-$C_6$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio, $C_3$-$C_7$cycloalkylthio (where the cycloalkyl group is optionally substituted with $C_1$-$C_6$alkyl or halogen), tri($C_1$-$C_4$)-alkylsilyl($C_1$-$C_6$)alkylthio, arylthio, $C_1$-$C_6$alkylsulfonyl, $C_1$-$C_6$haloalkylsulfonyl, $C_1$-$C_6$alkylsulfinyl, $C_1$-$C_6$haloalkylsulfinyl, arylsulfonyl, tri($C_1$-$C_4$)alkylsilyl, aryldi($C_1$-$C_4$)alkylsilyl, $C_1$-$C_4$alkyldiarylsilyl, triarylsilyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$alkyl)aminocarbonyl, N—($C_1$-$C_3$ alkyl)-N—($C_1$-$C_3$alkoxy)aminocarbonyl, $C_1$-$C_6$alkylcarbonyloxy, arylcarbonyloxy, di($C_1$-$C_6$) alkylaminocarbonyloxy, aryl (itself optionally substituted with $C_1$-$C_6$alkyl or halogen), heteroaryl (itself optionally substituted with $C_1$-$C_6$alkyl or halogen), heterocyclyl (itself optionally substituted with $C_1$-$C_6$alkyl or halogen), aryloxy (where the aryl group is optionally substituted with $C_1$-$C_6$alkyl or halogen), heteroaryloxy (where the heteroaryl group is optionally substituted with $C_1$-$C_6$alkyl or halogen), heterocyclyloxy (where the heterocyclyl group is optionally substituted with $C_1$-$C_6$alkyl or halogen), amino, $C_1$-$C_6$alkylamino, di($C_1$-$C_6$)alkylamino, $C_1$-$C_6$alkylcarbonylamino, N($C_1$-$C_6$)alkylcarbonyl-N—($C_1$-$C_6$)alkylamino, arylcarbonyl, (where the aryl group is itself optionally substituted with halogen or $C_1$-$C_6$alkyl) or two adjacent positions on an aryl or heteroaryl system may be cyclised to form a 5, 6 or 7 membered carbocyclic or heterocyclic ring, itself optionally substituted with halogen or $C_1$-$C_6$alkyl. Further substituents for aryl or heteroaryl include arylcarbonylamino (where the aryl group is substituted by $C_1$-$C_6$alkyl or halogen), ($C_1$-$C_6$)alkoxycarbonylamino, ($C_1$-$C_6$)alkoxycarbonyl-N—($C_1$-$C_6$)alkylamino, aryloxycarbonylamino (where the aryl group is substituted by $C_1$-$C_6$alkyl or halogen), aryloxycarbonyl-N—($C_1$-$C_6$)alkylamino, (where the aryl group is substituted by $C_1$-$C_6$alkyl or halogen), arylsulphonylamino (where the aryl group is substituted by $C_1$-$C_6$alkyl or halogen), arylsulphonyl-N—($C_1$-$C_6$)alkylamino (where the aryl group is substituted by $C_1$-$C_6$alkyl or halogen), aryl-N—($C_1$-$C_6$)alkylamino (where the aryl group is substituted by $C_1$-$C_6$alkyl or halogen), arylamino (where the aryl group is substituted by $C_1$-$C_6$alkyl or halogen), heteroaryl amino (where the heteroaryl group is substituted by $C_1$-$C_6$alkyl or halogen), heterocyclylamino (where the heterocyclyl group is substituted by $C_1$-$C_6$alkyl or halogen), aminocarbonylamino, $C_1$-$C_6$alkylaminocarbonylamino, di($C_1$-$C_6$)alkylaminocarbonylamino, arylaminocarbonylamino where the aryl group is substituted by $C_1$-$C_6$alkyl or halogen), aryl-N—($C_1$-$C_6$)alkylaminocarbonylamino where the aryl group is substituted by $C_1$-$C_6$alkyl or halogen), $C_1$-$C_6$alkylaminocarbonyl-N—($C_1$-$C_6$)alkylamino, di($C_1$-$C_6$)alkylaminocarbonyl-N—($C_1$-$C_6$)alkylamino, arylaminocarbonyl-N—($C_1$-$C_6$)alkylamino where the aryl group is substituted by $C_1$-$C_6$alkyl or halogen) and aryl-N—($C_1$-$C_6$) alkylaminocarbonyl-N—($C_1$-$C_6$)alkylamino where the aryl group is substituted by $C_1$-$C_6$alkyl or halogen).

For substituted heterocyclyl groups it is preferred that one or more substituents are independently selected from halogen, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, nitro and cyano. It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected $C_1$-$C_6$alkyl groups. When heterocyclic rings are formed by joining two groups on an N atom, the resulting rings are suitably pyrrolidine, piperidine, thiomorpholine and morpholine each of which may be substituted by one or two independently selected $C_1$-$C_6$alkyl groups.

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and di-isopropylamine.

Preferred quaternary ammonium bases suitable for salt formation correspond, for example, to the formula $[N(R_aR_bR_cR_d)]OH$, wherein $R_a$, $R_b$, $R_c$ and $R_d$ are each independently of the others hydrogen, $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula $[SR_eR_fR_g]OH$, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O=C—C=O unit.

The compounds of formula I according to the invention also include hydrates which may be formed during the salt formation.

The latentiating groups G are selected to allow its removal by one or a combination of biochemical, chemical or physical processes to afford compounds of formula I where G is H before, during or following application to the treated area or plants. Examples of these processes include enzymatic cleavage, chemical hydrolysis and photolysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

The latentiating group G is preferably selected from the groups $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—N($R^c$)—$R^d$, —$SO_2$—$R^e$, —$P(X^e)(R^f)$—$R^g$ or $CH_2$—$X^f$—$R^h$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$—($C_1$-$C_5$)oxyalkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_1$-$C_5$)alkylamino($C_1$-$C_5$)alkyl, $C_3$-$C_8$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{18}$haloalkyl, $C_1$-$C_{10}$cyanoalkyl, $C_1$-$C_{10}$nitroalkyl, $C_2$-$C_{18}$-aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$) alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_1$-$C_5$)alkylamino($C_1$-$C_5$)alkyl, $C_3$-$C_8$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$-aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino, $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_2$-$C_{10}$haloalkyl, $C_1$-$C_{10}$cyanoalkyl, $C_1$-$C_{10}$nitroalkyl, $C_1$-$C_{10}$-aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{18}$-aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_8$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In particular, the latentiating group G is a group —C($X^a$)—$R^a$ or —C($X^b$)—$X^c$—$R^b$, and the meanings of $X^a$, $R^a$, $X^b$, $X^c$ and $R^b$ are as defined above.

It is preferred that G is hydrogen, an alkali metal or alkaline earth metal, where hydrogen is especially preferred.

Depending on the nature of the substituents, compounds of formula I may exist in different isomeric forms. For example, when G is hydrogen and $R^4$ and $R^5$ are different from $R^6$ and $R^7$, compounds of formula I may exist in different tautomeric forms:

Preferably, in the compounds of formula I, A is substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro, cyano, $C_3$-$C_6$cycloalkyl, $C_1$-$C_3$alkylcarbonyl, $C_1$-$C_4$alkoxycarbonyl, aminocarbonyl, $C_1$-$C_3$alkylaminocarbonyl, di-$C_1$-$C_3$alkylaminocarbonyl, $C_1$-$C_3$alkylaminocarbonyloxy, di-$C_1$-$C_3$alkylaminocarbonyloxy, aminothiocarbonyl, $C_1$-$C_3$alkylaminothiocarbonyl, di$C_1$-$C_3$alkylaminothiocarbonyl, $C_1$-$C_4$alkylcarbonylamino, $C_3$-$C_6$cycloalkylcarbonylamino, $C_1$-$C_4$alkoxycarbonylamino, $C_1$-$C_4$alkylthiocarbonylamino, $C_1$-$C_3$alkoxy$C_1$-$C_3$alkyl, $C_1$-$C_6$alkylthio$C_1$-$C_6$alkyl, $C_1$-$C_6$alkylsulfinyl$C_1$-$C_6$alkyl, $C_1$-$C_6$alkylsulfonyl$C_1$-$C_6$alkyl, $C_1$-$C_3$alkylsulfonyloxy, $C_1$-$C_3$haloalkylsulfonyloxy or di$C_1$-$C_6$alkylaminosulfonyl, or 2 substituents on adjacent carbon atoms of A together form a $C_3$-$C_4$alkylene, wherein 1 or 2 methylene groups are optionally substituted by halogen, or wherein 1 or 2 of these methylene groups are replaced by oxygen.

More preferably, A is phenyl, naphthyl, pyridyl, pyrazinyl, pyrimidinyl, pyridazinyl, benzothiazolyl, benzoxazolyl, cinnolinyl, quinolinyl, quinazolinyl, quinoxalinyl or benzotriazinyl in each case substituted by halogen, methyl, ethyl, trifluoromethyl, methoxy, difluoromethoxy, trifluoromethoxy, nitro or cyano.

$R^1$ is preferably methyl, ethyl, n-propyl, cyclopropyl, halogen, halomethoxy or haloethoxy, especially methyl or ethyl.

Preferably, $R^2$ is hydrogen, methyl or halogen, especially hydrogen.

Preferably, $R^3$ is hydrogen, methyl, ethyl, n-propyl, cyclopropyl, halogen, halomethoxy or haloethoxy, especially hydrogen, methyl or ethyl.

Preferably, $R^4$, $R^5$, $R^6$ and $R^7$ are independently of each other hydrogen, $C_1$-$C_6$alkyl, $C_1$-$C_4$haloalkyl, $C_1$-$C_4$alkoxy$C_1$-$C_4$alkyl, optionally substituted five- or six-membered heterocyclyl, or optionally substituted five- or six-membered heterocyclyl$C_1$-$C_2$alkyl, or $R^4$ and $R^5$, or $R^6$ and $R^7$, together with the atoms to which they are bonded form an optionally substituted saturated or unsaturated five- or six-membered carbocyclyl or heterocyclyl which contains one or two oxygen atoms, or $R^5$ and $R^6$, with the atoms to which they are bonded form an optionally substituted five- or six-membered saturated or unsaturated carbocyclyl which is optionally bridged by $C_1$-$C_2$ alkyldiyl or by oxygen.

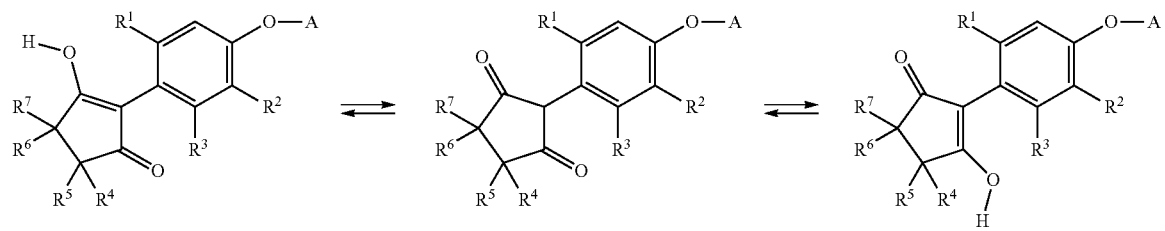

More preferably, $R^4$ and $R^7$ are hydrogen and $R^5$ and $R^6$, with the atoms to which they are bonded form a six-membered saturated or unsaturated carbocyclyl which is bridged by $C_1$-$C_2$ alkyldiyl or by oxygen.

This invention covers all such isomers and tautomers and mixtures thereof in all proportions. Also, when substituents contain double bonds, cis- and trans-isomers can exist. These isomers, too, are within the scope of the claimed compounds of the formula I.

Preferably, in the compounds of formula I, A is phenyl, naphthyl, a 5- or a 6-membered heteroaryl or a bicyclic 8- to 10-membered heteroaryl, A compound of formula I wherein G is $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating a compound of formula (A), which is a compound of formula (I) wherein G is H, with a reagent G-Z, wherein G-Z is an alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$alkyl sulfonate, or a di($C_1$-$C_8$alkyl)sulfate, or with a $C_3$-$C_8$alkenyl halide, or with a $C_3$-$C_8$alkynyl halide, or with an acylating agent such as a carboxylic acid, HO—$C(X^a)R^a$, wherein $X^a$ is oxygen, an acid chloride, Cl—$C(X^a)R^a$, wherein $X^a$ is oxygen, or acid anhydride, $[R^aC(X^a)]_2O$, wherein $X^a$ is oxygen, or an isocyanate, $R^cN$=C=O, or a carbamoyl chloride, Cl—$C(X^d)$—$N(R^c)$—$R^d$ (wherein $X^d$ is oxygen and with the proviso that neither $R^c$ or $R^d$ is hydrogen), or a thiocarbamoyl chloride Cl—$(X^d)$—$N(R^c)$—$R^d$ (wherein $X^d$ is sulfur and with the proviso that neither $R^c$ or $R^d$ is hydrogen) or a chloroformate, Cl—$C(X^b)$—$X^c$—$R^b$, (wherein $X^b$ and $X^c$ are oxygen), or a chlorothioformate Cl—$C(X^b)$—$X^c$—$R^b$ (wherein $X^b$ is oxygen and $X^c$ is sulfur), or a chlorodithioformate Cl—$C(X^b)$—$X^c$—$R^b$, (wherein $X^b$ and $X^c$ are sulfur), or an isothiocyanate, $R^cN$=C=S, or by sequential treatment with carbon disulfide and an alkylating agent, or with a phosphorylating agent such as a phosphoryl chloride, Cl—$P(X^e)(R^f)$—$R^g$ or with a sulfonylating agent such as a sulfonyl chloride Cl—$SO_2$—$R^e$, preferably in the presence of at least one equivalent of base.

Where substituents $R^4$ and $R^5$ are not equal to substituents $R^6$ and $R^7$, these reactions may produce, in addition to a compound of formula (I), a second compound of formula ($I_A$).

The O-acylation of cyclic 1,3-diones may be effected by procedures similar to those described, for example, by R. Haines, U.S. Pat. No. 4,175,135, and by T. Wheeler, U.S. Pat. No. 4,422,870, U.S. Pat. No. 4,659,372 and U.S. Pat. No. 4,436,666. Typically diones of formula (A) may be treated with an acylating agent preferably in the presence of at least one equivalent of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]-octane and 1,8-diazabicyclo [5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598; T. Isobe and T. Ishikawa, J. Org. Chem., (1999), 64 (19), 6984-6988 and K. Nicolaou, T. Montagnon, G. Vassilikogiannakis, C. Mathison, J. Am. Chem. Soc., (2005), 127 (24), 8872-8888.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A) may be achieved using an alkyl or aryl sulfonyl halide, preferably in

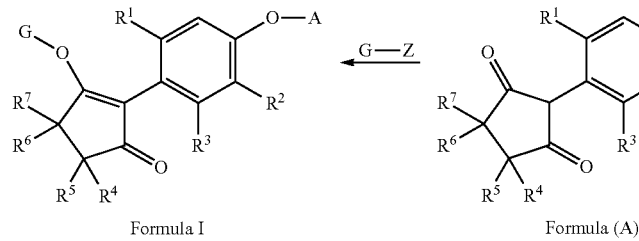

Formula I

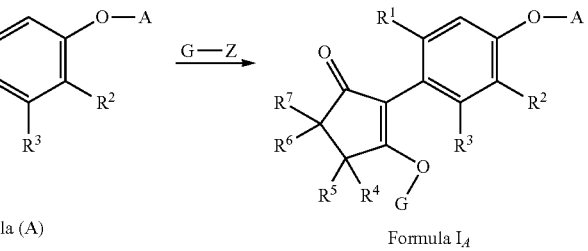

Formula (A)      Formula $I_A$

This invention covers both a compound of formula (I) and a compound of formula ($I_A$), together with mixtures of these compounds in any ratio.

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425-426; H. Born et al., J. Chem. Soc., (1953), 1779-1782; M. G. Constantino et al., Synth. Commun., (1992), 22 (19), 2859-2864; Y. Tian et al., Synth. Commun., (1997), 27 (9), 1577-1582; S. Chandra Roy et al., Chem. Letters, (2006), 35 (1), 16-17; P. K. Zubaidha et al., Tetrahedron Lett., (2004), 45, 7187-7188.

the presence of at least one equivalent of base, for example by the procedure of C. Kowalski and K. Fields, J. Org. Chem., (1981), 46, 197-201.

A compound of formula (A) may be prepared via the cyclisation of a compound of formula (B), preferably in the presence of an acid or base, and optionally in the presence of a suitable solvent, by analogous methods to those described by T. Wheeler, U.S. Pat. No. 4,283,348. The compounds of the formula (B) have been particularly designed as intermediates in the synthesis of the compounds of the formula I. Compounds of formula (B) wherein R is hydrogen or $C_1$-$C_4$alkyl, (especially methyl, ethyl and tert-butyl) may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

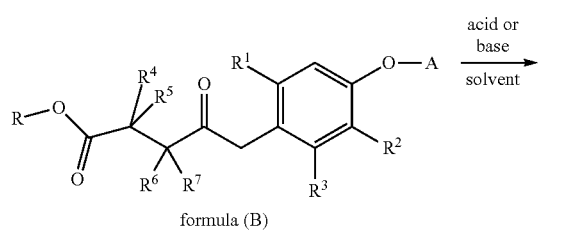

formula (B)

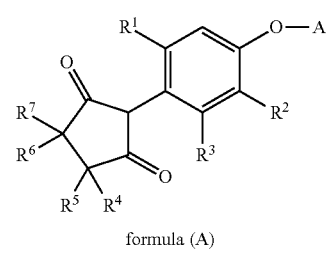

formula (A)

A compound of formula (B) wherein R is alkyl (preferably methyl or ethyl) may be cyclised under acidic or basic conditions, preferably under basic conditions in the presence of at least one equivalent of a strong base such as potassium tert-butoxide, lithium diisopropylamide, sodium bis(trimethylsilyl)amide or sodium hydride and in a solvent such as tetrahydrofuran, toluene, dimethylsulfoxide or N,N-dimethylformamide.

A compound of formula (B), wherein R is H may be esterified to a compound of formula (B), wherein R is alkyl, under known conditions (for example by treatment with an alcohol, R—OH, in the presence of an acid catalyst).

A compound of formula (B), wherein R is H may be prepared by hydrolysis of a compound of formula (C) wherein R is H or alkyl and R' is alkyl (preferably methyl or ethyl), followed by acidification of the reaction mixture to effect decarboxylation. Alternatively, a compound of formula (B), wherein R is alkyl may be prepared from a compound of formula (C), wherein R is alkyl and R' is methyl or ethyl (preferably methyl) through a Krapcho decarboxylation procedure under known conditions using known reagents (see for example G. Quallich, P. Morrissey, Synthesis, (1993), (1), 51-53).

A compound of formula (C), wherein R is H, may be prepared by treating a compound of formula (D) with a suitable base (such as potassium tert-butoxide, sodium bis(trimethylsilyl)amide and lithium diisopropylamide) in a suitable solvent (such as tetrahydrofuran or toluene) at a suitable temperature (between −80° C. and 30° C.) and reacting the resulting anion with a suitable anhydride of formula (E):

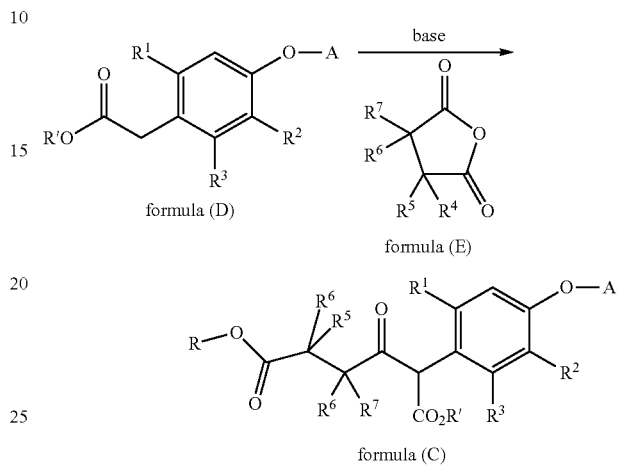

formula (D)

formula (E)

formula (C)

Compounds of formula (D) are known, or may be made by similar methods from known compounds (see, for example, P. Ple and F. Jung, WO06/040520; M. He et al., WO05/021554; Y. Kohno et al., WO03/029184; W. Marshall, U.S. Pat. No. 3,649,679; M. Ryozo et al., Chem. Pharm. Bull., (1983), 31 (10), 3424-3445; R. Trust et al., J. Med. Chem., (1979), 22 (9), 1068-1074). Compounds of formula (E) are known, or may be made by known methods from commercially available starting materials (see, for example, J. Rowley et al., J. Am. Chem. Soc., (2007), 129 (16), 4948-4960; J. Pohlmann et al., Bioorg. Med. Chem. Lett., (2005), 15(4), 1189-1192; L. Fieser and E. Martin., Org. Synth. Coll. Vol. II, (1943), 560-561).

In an alternative approach, a compound of formula (A) may be prepared by cross-coupling a dione of formula (F) with an aryl halide of formula (G). Similar couplings are known in the literature (see for example, S. Buchwald et al., J. Am. Chem. Soc. (2000), 122, 1360-1370; B. Hong et al. WO 2005/000233).

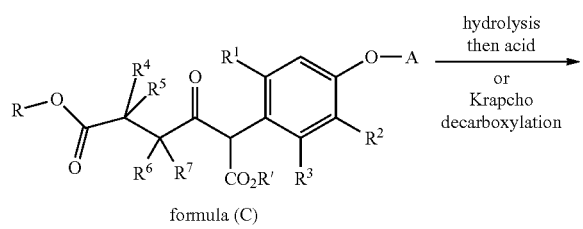

formula (C)

formula (B)

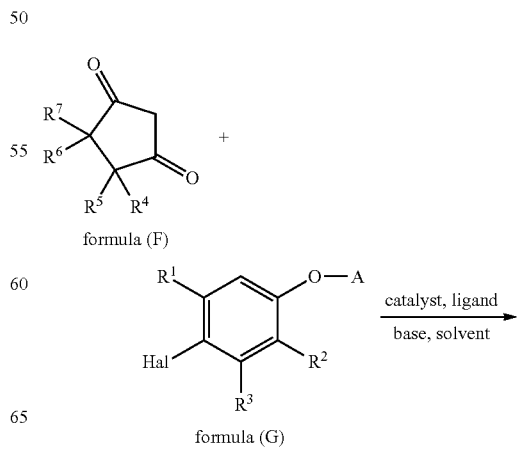

formula (F)

formula (G)

-continued

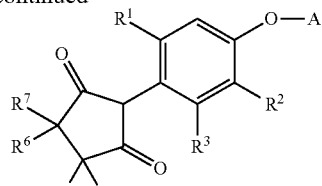

formula (A)

-continued

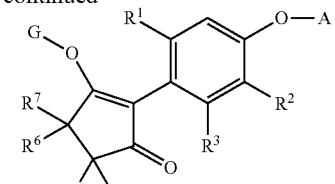

formula I, wherein
G is $C_1$-$G_4$alkyl

Compounds of formula (F) are known, or may be made by known methods from known compounds (see, for example M. Nishizawa et al., Synlett., (2006), 4, 642-644; J. Mascarenas et al., Org. Lett., (2003), 5 (11), 1975-1977; A. Demir and D. Enders, Journal fuer Praktische Chemie, (1997), 339 (6), 553-563; B. Zwanenburg et al., Tetrahedron (1989), 45 (22), 7109-7133; A. Demir and D. Enders, Tetrahedron Lett., (1989), 30 (13), 1705-1708; E. Guntrum et al., Synthesis, (1986), (11), 921-925, and by M. Oda et al., Chem. Lett., (1977), 6 (3), 307-310).

Aryl halides of formula (G) are known compounds or may be made by known methods from known compounds (see, for example, R. Trust et al., J. Med. Chem., (1979), 22 (9), 1068-1074).

In an alternative approach, a compound of formula I, wherein G is $C_1$-$C_4$alkyl may be prepared by reacting a compound of formula (H) (wherein G is $C_{1-4}$ alkyl, and Hal is a halogen, preferably bromine or iodine), with an arylboronic acid of formula (I) in the presence of a suitable palladium catalyst (for example 0.001-50% palladium(II) acetate with respect to compound (H)) and a base (for example 1 to 10 equivalents potassium phosphate with respect to compound (H)) and preferably in the presence of a suitable ligand (for example 0.001-50% (2-dicyclohexylphosphino)-2',6'-dimethoxybiphenyl with respect to compound (U)), and in a suitable solvent (for example toluene), preferably between 25° C. and 200° C. Similar couplings are known in the literature (see for example, Y. Song, B. Kim and J.-N. Heo, Tetrahedron Letters (2005), 46 (36), 5987-5990).

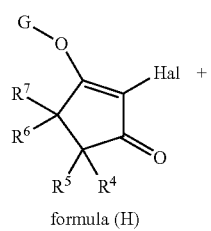

formula (H)

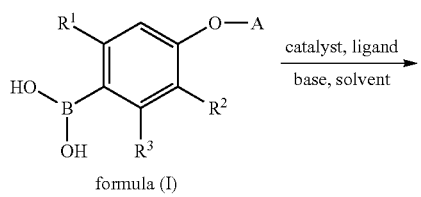

formula (I)

A compound of formula (H) may be prepared by halogenating a compound of formula (F), followed by reaction of the resulting halide of formula (J) with a $C_1$-$C_4$ alkyl halide or tri-$C_1$-$C_4$-alkylorthoformate under known conditions, for example by the procedures of R. Shepherd and A. White (J. Chem. Soc. Perkin Trans. 1 (1987), 2153-2155) and Y.-L. Lin et al. (Bioorg. Med. Chem. (2002), 10, 685-690). Alternatively, a compound of formula (H) may be prepared by reacting a compound of formula (F), with a $C_1$-$C_4$alkyl halide or a tri-$C_1$-$C_4$-alkylorthoformate, and halogenating the resulting enone of formula (K) under known conditions (see for example Y. Song, B. Kim and J.-N. Heo, Tetrahedron Letters (2005), 46 (36), 5987-5990).

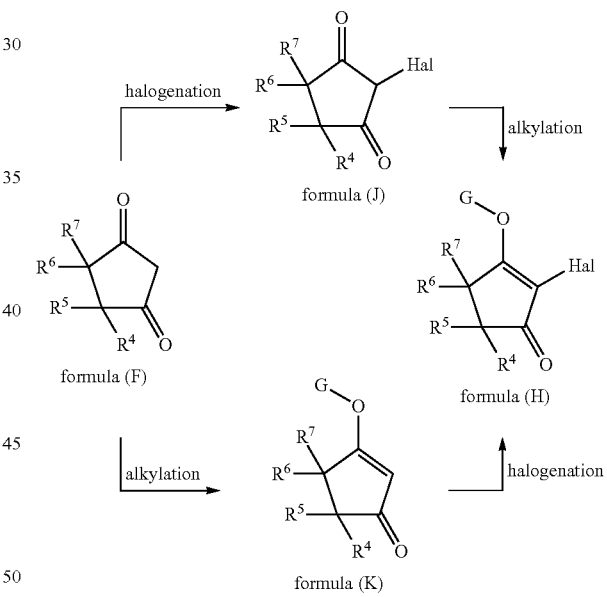

In a further approach, a compound of formula (A) may be prepared by reacting a compound of formula (F) with an aryllead tricarboxylate, in the presence of a suitable ligand and in a suitable solvent. Similar reactions are described in the literature (for example see, M. Muehlebach et al., WO08/071,405; J. Pinhey, B. Rowe, Aust. J. Chem., (1979), 32, 1561-6; J. Morgan, J. Pinhey, J. Chem. Soc. Perkin Trans. 1, (1990), 3, 715-20). Preferably the aryllead tricarboxylate is an aryllead triacetate of formula (L). Preferably the ligand is a nitrogen containing heterocycle such as N,N-dimethylamino-pyridine, 1,10-phenanthroline pyridine, bipyridine, or imidazole, and one to ten equivalents of ligand with respect to a compound of formula (F) is preferably used. Most preferably the ligand is N,N-dimethylaminopyridine. The solvent is preferably chloroform, dichloromethane or toluene, most preferably chloroform, or a mixture of chloroform and toluene. Preferably the reaction is conducted at a temperature of −10° C. to 100° C., most preferably at 40-90° C.).

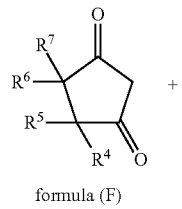

formula (F)

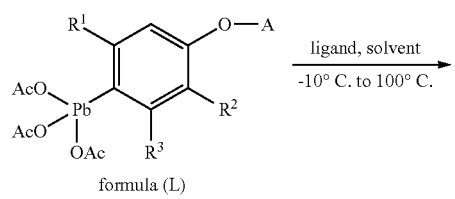

formula (L)

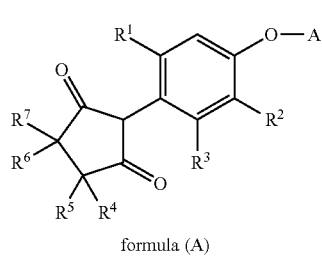

formula (A)

A compound of formula (L) may be prepared from a compound of formula (I) by treatment with lead tetraacetate in a suitable solvent (for example chloroform) at 25° C. to 100° C. (preferably 25-50° C.), and optionally in the presence of a catalyst such as mercury diacetate, according to procedures described in the literature (for example see, M. Muehlebach et al., WO08/071,405; K. Shimi, G. Boyer, J-P. Finet and J-P. Galy, Letters in Organic Chemistry, (2005), 2, 407-409; J. Morgan and J. Pinhey, J. Chem. Soc. Perkin Trans. 1; (1990), 3, 715-720).

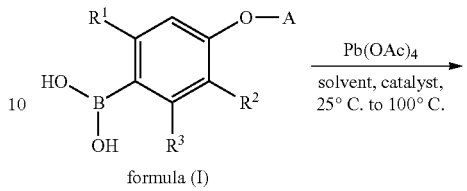

formula (I)

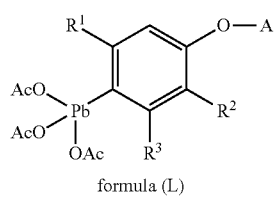

formula (L)

An aryl boronic acid of formula (I) may be prepared from an aryl halide of formula (G), wherein Hal is bromine or iodine by known methods (see, for example, W. Thompson and J. Gaudino, J. Org. Chem., (1984), 49, 5237-5243 and R. Hawkins et al., J. Am. Chem. Soc., (1960), 82, 3053-3059). Thus an aryl halide of formula (G) may be treated with an alkyl lithium or alkyl magnesium halide at low temperature, and the aryl magnesium or aryl lithium reagent obtained is allowed to react with a trialkyl borate, B(OR″)$_3$, preferably trimethylborate (R″ is methyl), to give an aryl dialkylboronate which may be hydrolysed to the desired boronic acid of formula (I) under acidic conditions. Alternatively the same overall transformation of compound (G) to compound (I) may be achieved through a palladium-catalysed borylation reaction under known conditions using known reagents (see for example T. Ishiyama, M. Murata, N. Miyaura, J. Org. Chem. (1995), 60, 7508-7501; and K. L. Billingsley, T. E. Barder, S. L. Buchwald, Angew. Chem. Int. Ed. (2007), 46, 5359-5363), followed by hydrolysis of the intermediate boronate ester.

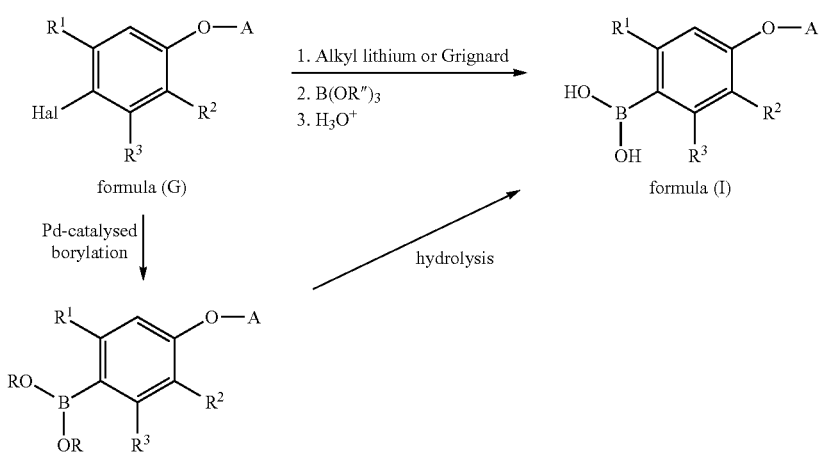

In a further approach, a compound of formula (A) may be prepared by derivatisation of a compound of formula (M), which is a compound of formula I wherein G is hydrogen and $R^5$ and $R^6$ together form a bond. Compounds of formula (M) are α,β-unsaturated cyclic diones and undergo reactions in the presence of reagents known to effect transformations of α,β-unsaturated ketones to give additional compounds of formula (A).

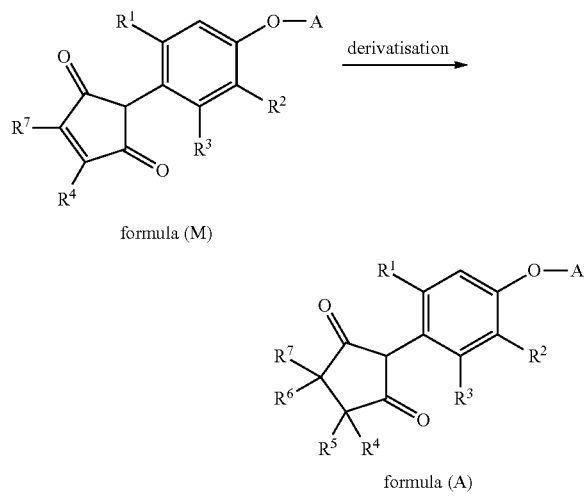

For example, a compound of formula (M) may be reacted with a suitable nucleophile, Nuc-H, optionally in the presence of a suitable base and a suitable solvent to give compounds of formula (A) wherein $R^5$ is the group Nuc resulting from nucleophilic attack and $R^6$ is hydrogen.

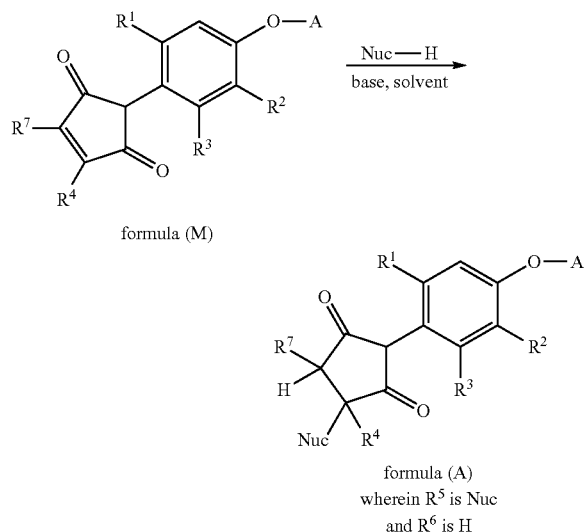

Suitable nucleophiles, Nuc-H, include, but are not limited to, optionally substituted $C_1$-$C_6$alkylthiols, optionally substituted arylthiols, optionally substituted heteroarylthiols optionally substituted $C_1$-$C_6$alkyl alcohols and optionally substituted $C_3$-$C_7$cyclic alcohols (including $C_3$-$C_6$ alicyclic alcohols, 4-6 membered heterocyclic alcohols, phenols and heteroaromatic alcohols).

A compound of formula (M) will also participate in cycloaddition reactions under suitable conditions to afford additional compounds of formula (A).

For example, a compound of formula (M) may be reacted with a suitable 1,3-diene of formula (N), wherein $R_a$ represents a suitable substituent (such as $C_1$-$C_4$alkyl, $C_1$-$C_4$alkoxy or tri-$C_1$-$C_4$alkylsilyloxy), and n is 0, 1 or 2, under suitable conditions to give a compound of formula (A) wherein $R^5$ and $R^6$ together with the atoms to which they are joined form an unsaturated six-membered ring.

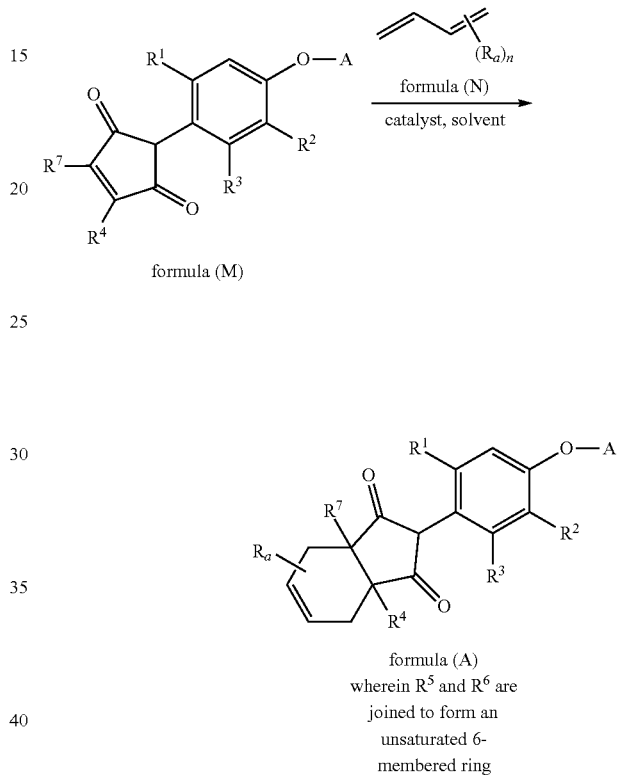

Suitable 1,3-dienes include 1,3-butadiene (or an equivalent, for instance 2,5-dihydrothiophene-1,1-dioxide), and substituted 1,3-butadienes. Similarly, a compound of formula (M) may also be reacted with cyclic dienes of formula (O) such as cyclopentadiene (W is —$CH_2$— and $R_b$ is hydrogen), substituted cyclopentadienes, cyclohexa-1,3-diene (W is —$CH_2$—$CH_2$— and $R_b$ is hydrogen), substituted cyclopentadienes, furan (W is oxygen and $R_b$ is hydrogen) and substituted furans.

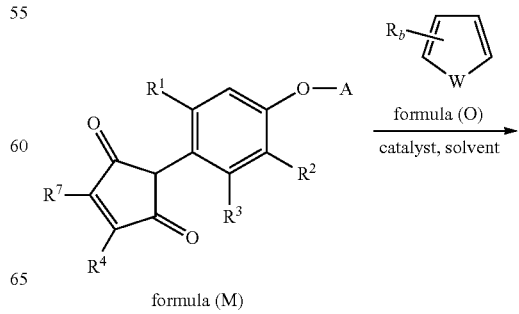

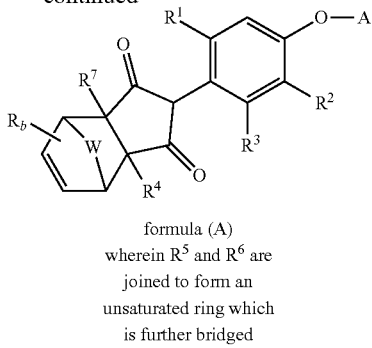

formula (A)
wherein $R^5$ and $R^6$ are
joined to form an
unsaturated ring which
is further bridged Those skilled in the art will appreciate that cyclic dienes of formula (O) bearing a wide variety of substituents $R_b$ will undergo cycloaddition reactions with a compound of formula (M) to give new compounds of formula (A), under appropriate conditions (for example, in the presence or absence of Lewis acid catalysts, such as aluminium chloride, bismuth (III) chloride, bismuth(III) trifluoromethanesulfonate, boron trifluoride, cerium(III) chloride, copper(I) trifluoromethanesulfonate, diethylaluminium chloride, hafnium(IV) chloride, iron(III) chloride, lithium perchlorate, lithium trifluoromethanesulfonate, magnesium bromide, magnesium iodide, scandium(III) trifluoromethanesulfonate, tin(IV) chloride, titanium(IV) chloride, titanium(IV) isopropoxide, trimethyl aluminium, N-trimethylsilyl-bis(trifluoromethanesulfonyl)imide, trimethylsilyl trifluoromethane-sulfonate, ytterbium(III) trifluoromethanesulfonate, zinc iodide and zirconium(IV) chloride, and in the presence or absence of solvents such as chloroform, dichloromethane, diethyl ether, ethanol, methanol, perfluorinated alkanes such as perfluorohexane, toluene, water, and ionic liquids such as 1-butyl-3-methylimidazolium tetrafluoroborate and 1-butyl-3-methylimidazolium hexafluorophosphate, and at normal atmospheric pressure or under high pressure conditions), as described, for example by G. Silvero et al., Tetrahedron (2005), 61, 7105-7111; I. Hemeon et al., Synlett, (2002), 11, 1815-1818; S. Otto and J. Engberts, Pure Appl. Chem. (2000), 72 (7), 1365-1372; R. Breslow, Acc. Chem. Res., (1991), 24 (6), 159-164; K. Hara et al., Org. Lett., (2005), 7 (25), 5621-5623; J, Augé et al., Synlett, (2000), 6, 877-879, B. Garrigues and A. Oussaid, J. Organometallic Chem., (1989), 585, 253-255; B. Mathieu and L. Ghosez, Tetrahedron Lett., (1997), 38 (31), 5497-5500; M. Ordoñez et al., Tetrahedron Asymmetry, (1996), 7 (9), 2675-2686; S. Kobayashi et al., Tetrahedron Lett., (1993), 34 (23), 3755-3758; C. Cativiela et al., U. Pindur et al., Chem. Rev., (1993), 93, 741-761; Tetrahedron, (1992), 48 (31), 6467-6476; J. Aubé et al., J. Am. Chem. Soc., (1992), 114, 5466-5467; S. Danishefsky and M. Bednarski, Tetrahedron Lett., (1985), 26 (21), 2507-2508 and references therein); Q. Chu, W. Zhang and D. Curran, Tetrahedron Lett., (2006), 47, 9287-9290; K. Ishihara and K. Nakano, J. Am. Chem. Soc., (2005), 127 (30), 10504-10505; and A. Northrup and D. MacMillan, (2002), J. Am. Chem. Soc., 124 (11), 2458-2460).

The reaction of compounds of formula (M) with compounds of formula (N) or with compounds of formula (O) provides compounds of formula (A) wherein $R^5$ and $R^6$ are joined to form an unsaturated ring. Such compounds are alkenes, which may undergo reactions typical of alkenes (for example reduction, halogenation or cross-coupling) to produce further compounds of formula (A).

A compound of formula (M) may also act as a dipolarophile and will therefore undergo a range of 3+2 cycloaddition reactions with suitable dipolar reagents under suitable conditions. For example, a compound of formula (M) may react with a nitrile oxide of formula (P), wherein $R_c$ is a suitable substituent (for example $C_1$-$C_4$alkyl or aryl), or with a nitrone of formula (Q), wherein $R_e$, $R_f$ and $R_g$ are suitable substituents (for example hydrogen or $C_1$-$C_4$alkyl), under appropriate conditions to give further compounds of formula (A), wherein $R^4$ and $R^7$ together with the atoms to which they are attached form an isoxazoline or isoxazolidine ring respectively.

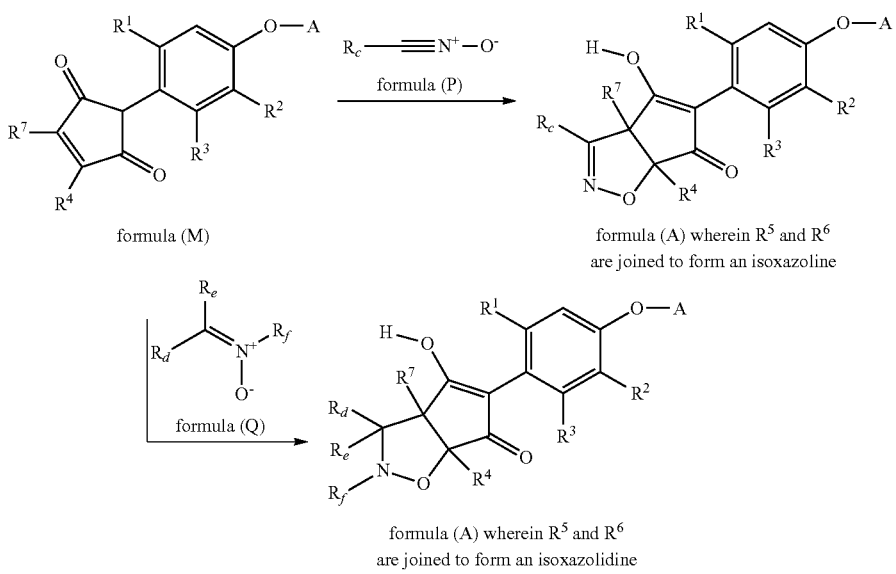

Suitable conditions for effecting 3+2 cycloadditions are described, for example, by L. Deng and Y. Hu, Synth. Commun. (2007), 37, 157-163; E. Kantorowski et al., J. Org. Chem., (1998), 63, 5272-5274; and by V. Jäger and I. Müller, Tetrahedron (1985), 41 (17), 3519-3528.

A compound of formula (M), may be prepared by oxidising a compound of formula (R) in a suitable solvent such as toluene, acetone, chloroform, dichloromethane or 1,4-dioxane. A wide range of oxidants is suitable for effecting this transformation, including inorganic oxidants such as chromium trioxide, pyridinium dichromate, manganese dioxide and aluminium alkoxides such as aluminium isopropoxide, as well as organic oxidants such as 2,3-dichloro-5,6-dicyano-p-benzoquinone and hypervalent iodine oxidants such as 1,1,1-tris(acetyloxy)-1,1-dihydro-1,2-benziodoxol-3-(1H)-one (Dess-Martin periodinane), Suitable procedures are described, for example, by K. Saito and H. Yamachika, U.S. Pat. No. 4,371,711. and by G. Piancatelli et al., Tetrahedron (1978), 34, 2775. The use of chromium trioxide in a mixture of sulfuric acid and acetone (Jones reagent) is preferred.

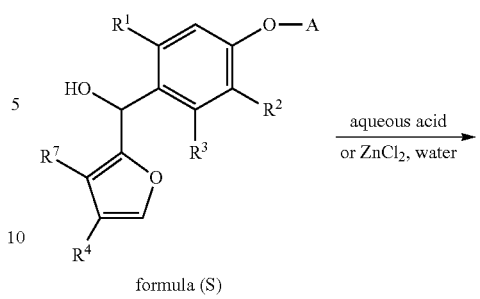

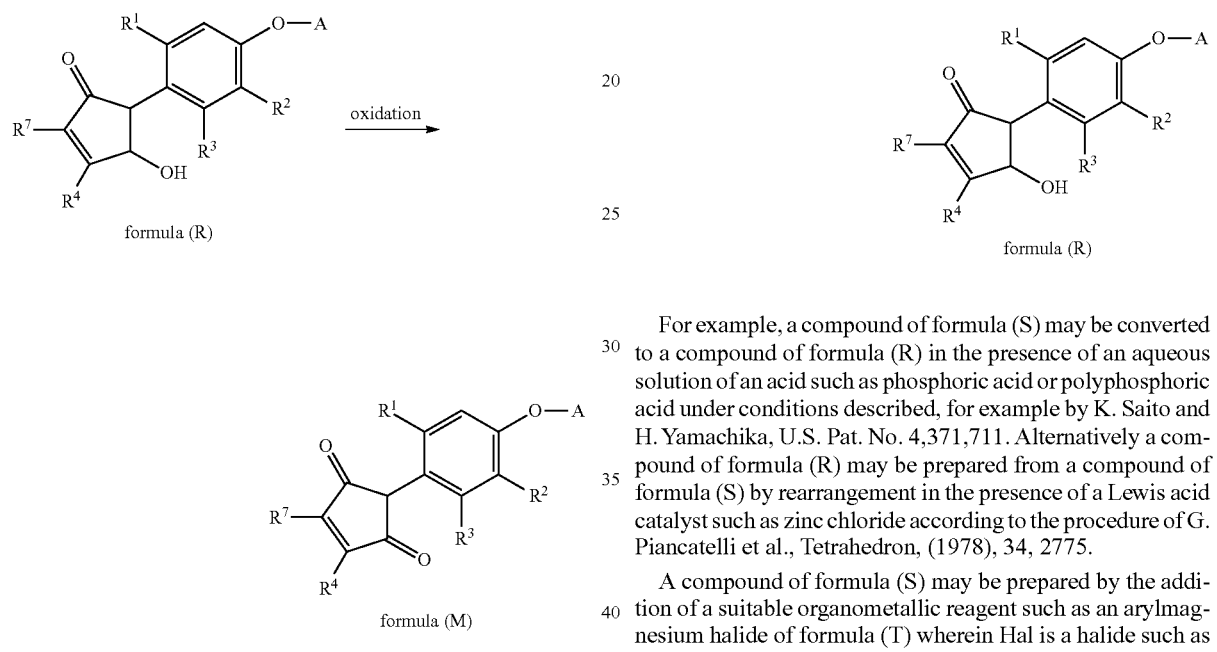

A compound of formula (R) may be prepared from a compound of formula (S) by treatment with a suitable acid catalyst in the presence of water and optionally in the presence of a suitable solvent.

For example, a compound of formula (S) may be converted to a compound of formula (R) in the presence of an aqueous solution of an acid such as phosphoric acid or polyphosphoric acid under conditions described, for example by K. Saito and H. Yamachika, U.S. Pat. No. 4,371,711. Alternatively a compound of formula (R) may be prepared from a compound of formula (S) by rearrangement in the presence of a Lewis acid catalyst such as zinc chloride according to the procedure of G. Piancatelli et al., Tetrahedron, (1978), 34, 2775.

A compound of formula (S) may be prepared by the addition of a suitable organometallic reagent such as an arylmagnesium halide of formula (T) wherein Hal is a halide such as chloride, bromide or iodide, or an aryllithium reagent of formula (U) or a diarylzinc reagent of formula (V) to a furan-2-carboxaldehyde of formula (W) according to known procedures (see, for example G. Panda et al., Tetrahedron Lett., (2005), 46, 3097).

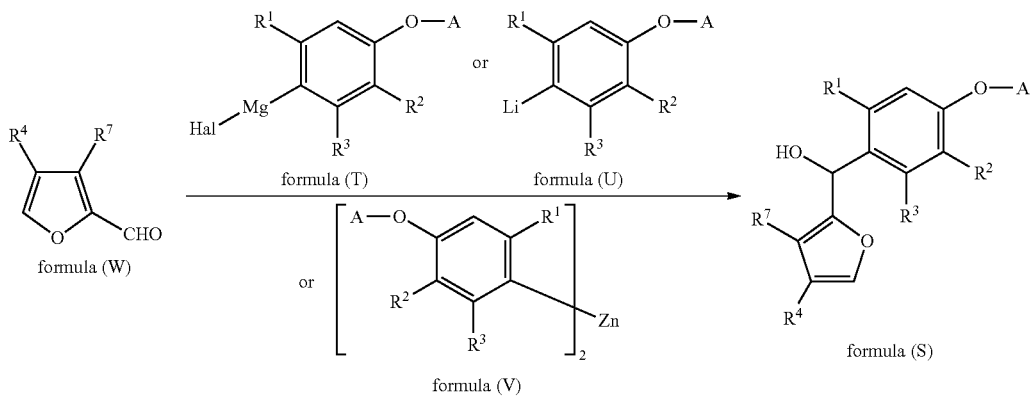

The organometallic reagents of formula (T), formula (U) and formula (V) may be made by known methods from a compound of formula (G).

In a further approach, a compound of formula (A), wherein $R^5$ is Nuc (and Nuc is as previously defined) may be prepared by the hydrolysis of a compound of formula (X), which is a compound of formula I wherein G is $C_1$-$C_4$alkyl, under acidic conditions.

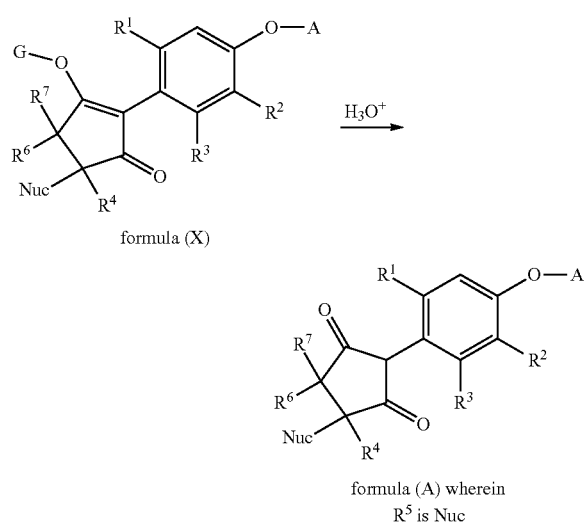

A compound of formula (X) may be prepared from a compound of formula (Y), which is a compound of formula I wherein $R^5$ is Hal and Hal is chlorine, bromine or iodine, by treatment with a nucleophile, Nuc-H, optionally in the presence of a suitable base and in a suitable solvent. Suitable conditions for effecting nucleophilic substitution reactions are described, for example, by J. March, Advanced Organic Chemistry Third Edition, ed J. Wiley and Sons, 1985.

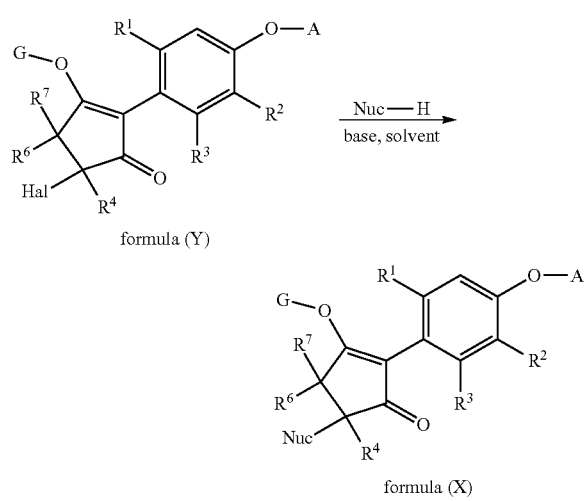

A compound of formula (Y) may be prepared from a compound of formula (Z), which is a compound of formula I wherein $R^5$ is H and G is $C_1$-$C_4$alkyl, by halogenation.

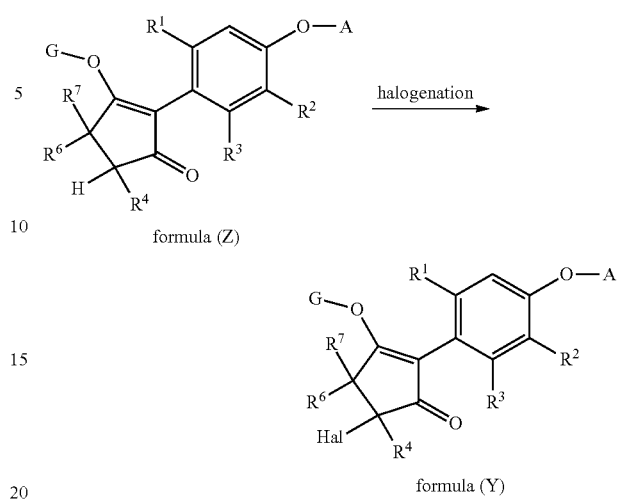

For example, a compound of formula (Y) wherein Hal is chlorine may be prepared by reacting a compound of formula (Z) with copper(II) chloride and lithium chloride according to the procedure of E. Kosower et al., J. Org. Chem., (1963), 28, 630. Alternatively a compound of formula (Y) wherein Hal is bromine may be prepared treating a compound of formula (Z) with dibutylboryl trifluoromethanesulfonate and N-bromosuccinimide, by methods similar to those described by P. Page et al., Tetrahedron (1995), 51 (4), 1285-1294).

A compound of formula (Z) may be prepared reaction of a compound of formula (AA) with a $C_1$-$C_4$alkyl halide in the presence of a base and a solvent, or by reaction with a tri-$C_1$-$C_4$-alkylorthoformate under conditions similar to those described for the preparation of a compound of formula (K).

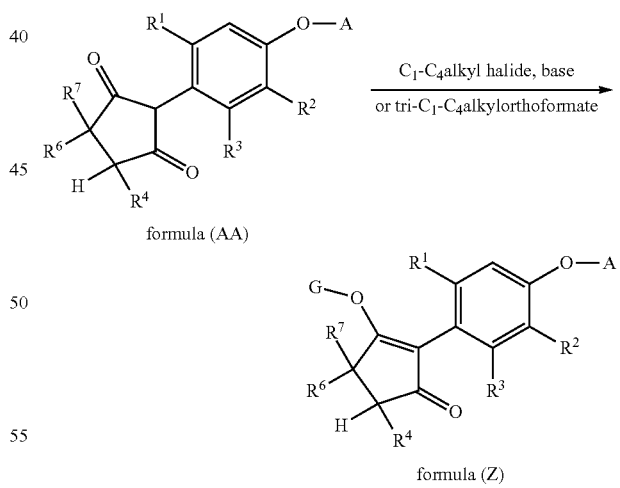

A compound of formula (AA) is a compound of formula I, wherein $R^5$ is hydrogen, and may be made methods described previously for the preparation of a compound of formula (A).

Alternatively, a compound of formula (AA) wherein $R^6$ is hydrogen may be prepared by reduction of a compound of formula (M), for example by catalytic hydrogenation, or by the use of a suitable metal (such as zinc) in a suitable solvent (such as acetic acid).

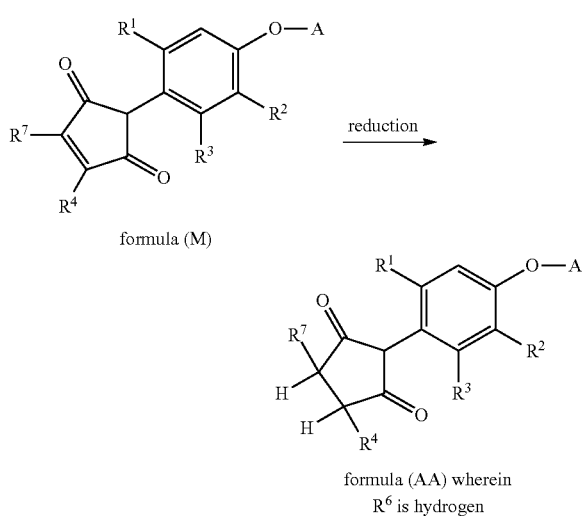

formula (M)

formula (AA) wherein R⁶ is hydrogen

In a further approach, a compound of formula I may be prepared by cross-coupling an aryl halide of formula (BB), wherein Hal represents bromine or iodine, with a phenol, A—OH, in the presence of a suitable catalyst, optionally a suitable ligand or additive, a suitable base and a suitable solvent.

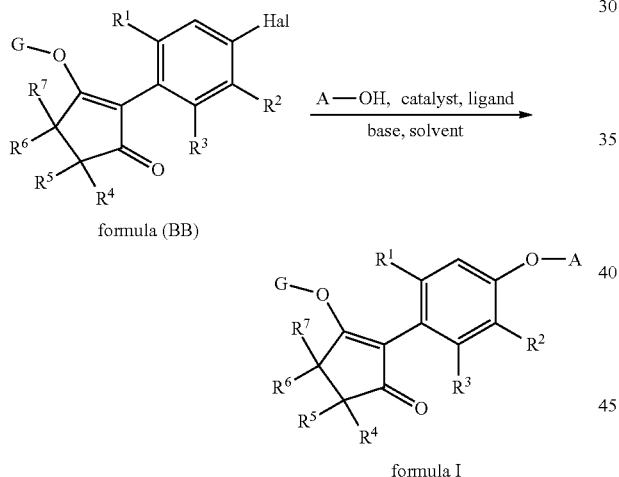

formula (BB)

formula I

Suitable conditions for effecting this cross-coupling are described, for example, by S. Hu et al., J. Org. Chem., (2008), 73, 7814-7817; P. Chan et al., Tetrahedron Lett., (2008), 49, 2018-2022); R. Hosseinzadeh et al., Synthetic Commun., (2008) 38, 3023-3031; S. Buchwald et al., J. Am. Chem. Soc., (2006), 128, 10694-10695; H. Rao et al., Chem. Eur. J., (2006), 12, 3636-3646; M. Taillefer et al., Adv. Synth. Catal. (2006), 348, 499-505; M. Beller et al., Tetrahedron Lett., (2005), 46 (18), 3237-3240; M. Taillefer et al., Org. Lett. (2004), 6 (6), 913; D. Ma and Q. Cai, Org. Lett. (2003), 5 (21), 3799-3802; J. Song et al., Org. Lett. (2002), 4 (9), 1623-1626; R. Venkataraman et al., Org. Lett. (2001), 3 (26), 4315-4317; S. Buchwald et al., J. Am. Chem. Soc. (1999), 121, 4369-4378; S. Buchwald et al., J. Am. Chem. Soc., (1997), 119, 10539-10540; G. Mann and J. Hartwig, Tetrahedron Lett., (1997), 38 (46), 8005-8008.

Suitable catalysts include palladium and copper catalysts such as palladium(II) acetate, bis(dibenzylideneacetone)palladium(II), copper powder, copper(II) acetate, copper(I) chloride, copper(I) bromide, copper(II) bromide, copper(I) iodide, copper(I) oxide, copper(II) sulfate, copper(I) trifluoromethanesulfonate and copper(II) trifluoromethanesulfonate. Optionally the catalysts are used in conjunction with appropriate ligands or additives, such as N-methylglycine N,N-dimethylglycine, 1-butylimidazole, ethyl acetate, ethylene glycol diacetate, 8-hydroxyquinoline, L-proline, 1-naphthoic acid, triphenylphosphine, 1,1'-bis(diphenylphosphino)ferrocene, salicylaldoxime, 2-(N,N-dimethylamino)-2'-di-tert-butylphosphinobiphenyl, neocuproine, pyrrolidine-2-phosphionic acid phenyl monoester, 2,2,6,6-tetramethylheptane-3,5-dione, tetrabutylammonium bromide, 2,2-bipyridine or 1,10-phenanthroline. Suitable bases are cesium carbonate, cesium fluoride, potassium fluoride, potassium phosphate and sodium hydroxide. Suitable solvents are acetonitrile, N,N-dimethylformamide, 1,4-dioxane or toluene, or mixed solvent systems such as toluene/tetrahydrofuran and 1,4-dioxane/water.

The use of copper(I) iodide and copper(II) trifluoromethanesulfonate catalysts is preferred.

A compound of formula (BB) may be prepared by one of the methods described previously for the synthesis of a compound of formula (A), using appropriate starting materials. For example, a compound of formula (BB), wherein G is hydrogen, may be prepared from a compound of formula (F) and an aryllead reagent of formula (CC) under conditions described previously.

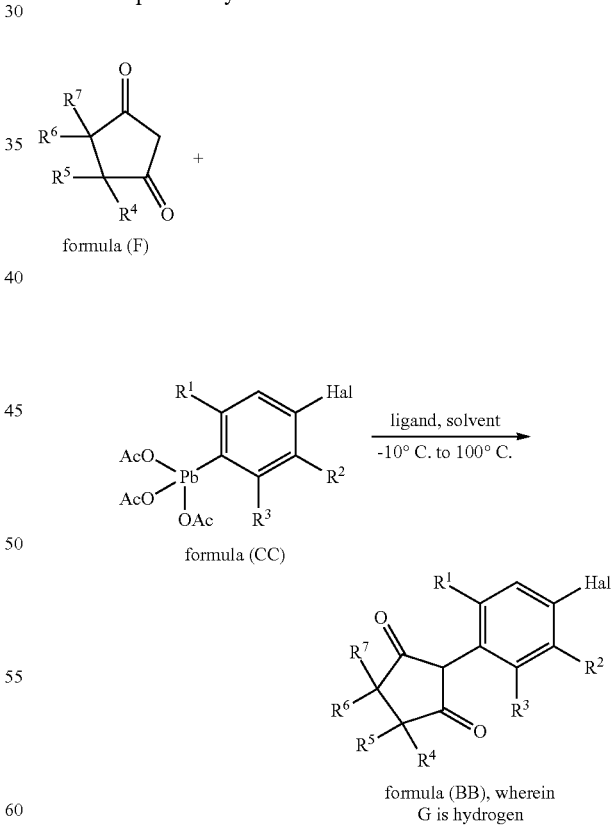

formula (F)

formula (CC)

formula (BB), wherein G is hydrogen

In a further approach, a compound of formula I may be prepared by reacting a compound of formula (DD) with an aryl- or heteroaryl halide of formula A-Hal, wherein Hal represents fluorine, chlorine, bromine or iodine under appropriate conditions.

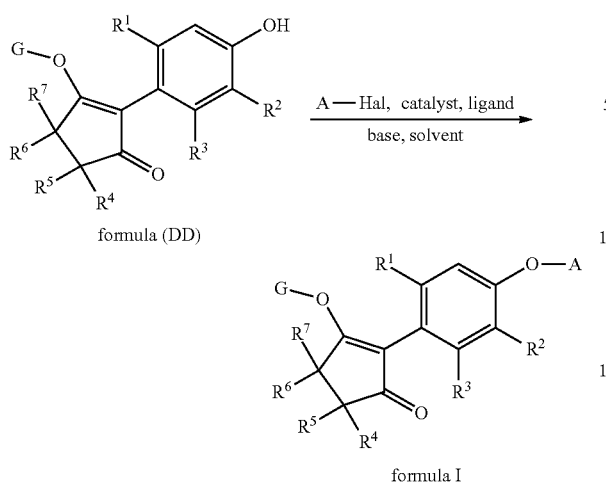

formula (DD)

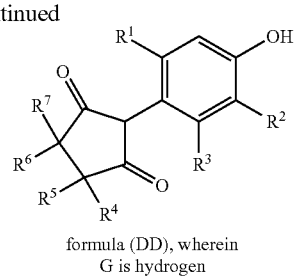

formula (DD), wherein G is hydrogen formula I

When A-Hal is an aryl bromide or aryl iodide, the reaction may be effected using suitable copper or palladium catalysts under conditions described previously for the preparation of a compound of formula (A) from a compound of formula (BB). Alternatively, when A-Hal is a suitable, electron-deficient, aryl halide (for example an aryl fluororide or aryl chloride additionally bearing one or more electron-withdrawing substituents such as trifluoromethyl, nitro or cyano), or a suitable heteroaryl halide (for example a halopyridine, or halopyrimidine, haloquinoline, haloquinazoline or haloquinoxaline) the reaction may be effected in the presence of a suitable base such as potassium carbonate or cesium carbonate, without the need for a catalyst and a ligand.

A compound of formula (DD), wherein G is hydrogen, may be prepared from a compound of formula (BB), wherein G is hydrogen.

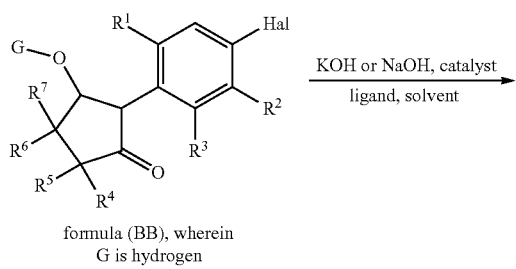

formula (BB), wherein G is hydrogen

In one approach, a compound of formula (BB), wherein G is hydrogen, is deprotonated with a base (such as a Grignard reagent or alkyllithium reagent), and then treated with an alkyllithium reagent to effect metal-halogen exchange. The resulting organometallic species may then be converted into a compound of formula (DD) by treatment with a trialkylborate such as trimethyl borate followed by oxidation (for example by hydrogen peroxide, N-methyl morpholine N-oxide or oxone) as described, for example by G. Prakash et al., J. Org. Chem., (2001), 66 (2), 633-634; J-P Gotteland and S Halazy, Synlett. (1995), 931-932; K. Webb and D. Levy, Tetrahedron Lett., (1995), 36 (29), 5117-5118. In an alternative approach, a compound of formula (DD), wherein G is hydrogen, may be prepared from a compound of formula (BB), wherein G is hydrogen, by treatment with an aqueous solution of an alkali metal hydroxide in the presence of a suitable catalyst and a suitable ligand, according to known procedures. For example, a compound of formula (DD), wherein G is hydrogen, may be prepared by treating a compound of formula (BB), wherein G is hydrogen, with potassium hydroxide in the presence of a palladium catalyst (for example bis(dibenzylidene-acetone) palladium(II), and in the presence of a suitable phosphine ligand such as 2-(di-tert-butylphosphino)-2',4',6'-triisopropylbiphenyl and 2-(di-tert-butylphosphino)-3,4,5,6-tetramethyl-2',4',6'-triisopropylbiphenyl, under conditions described, for example, by S. Buchwald et al., J. Am. Chem. Soc., (2006), 128, 10694-10695. Alternatively, a compound of formula (DD), wherein G is hydrogen, may be prepared by treating a compound of formula (BB), wherein G is hydrogen, by treatment with an aqueous solution of sodium hydroxide in the presence of a suitable copper catalyst (for example copper (I) iodide) and a suitable ligand (such as L-proline), under conditions described, for example, by C. Kormos and N. Leadbeater, Tetrahedron (2006), 62 (19), 4728-4732.

1. Grignard/Alkyllithium
2. B(OMe)$_3$
3. Oxidation

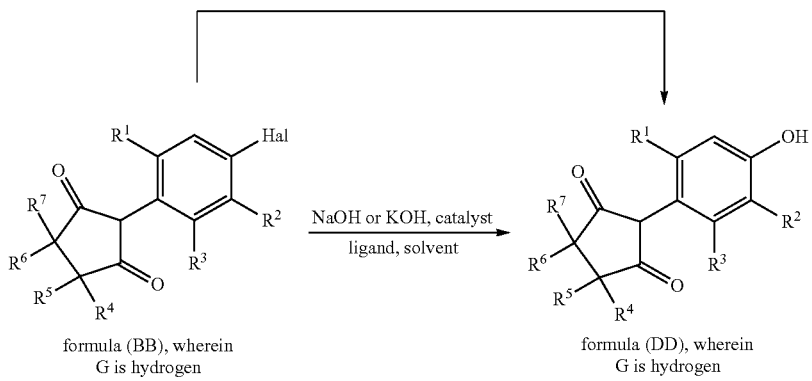

formula (BB), wherein G is hydrogen formula (DD), wherein G is hydrogen

In a further approach, a compound of formula (DD) may be prepared by the deprotection of a compound of formula (EE), wherein P is a suitable protecting group. Suitable protecting groups for phenols, and conditions for the removal of the protecting group are described, for example, by T. Green and P. Wuts, Protective Groups in Organic Synthesis, 3$^{rd}$ Edition, J. Wiley and Sons, (1999). Preferably the protecting group P is a benzyl group or is methyl.

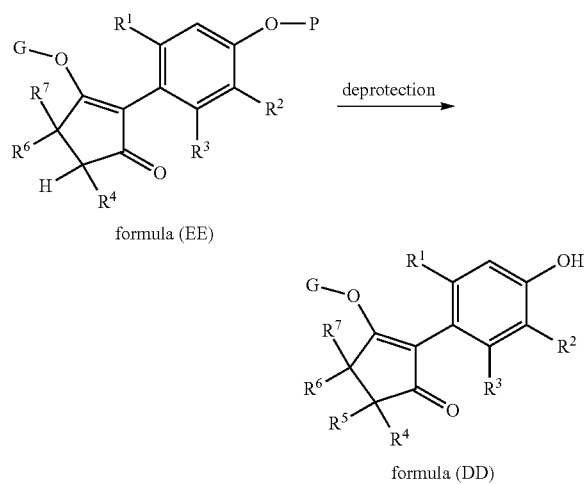

formula (EE)

formula (DD)

Compounds of formula (EE) may be prepared by one or more of the methods similar to those described above for the preparation of compounds of formula I, using appropriate starting materials and appropriate reagents.

The compounds of the formula (M) and (DD), have been particularly designed as intermediates in the synthesis of the compounds of formula I.

The compounds of formula I according to the invention can be used as crop protection agents in unmodified form, as obtained in the synthesis, but they are generally formulated into crop protection compositions in a variety of ways using formulation adjuvants, such as carriers, solvents and surface-active substances. The formulations can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or microrods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, chemically modified cellulose esters like carboxymethyl cellulose, methyl cellulose, hydroxyethyl cellulose, examples of suitable waxes are polyethylene wax, oxidized polyethylene wax, ester waxes like montan waxes, waxes of natural origin like carnauba wax, candelilla wax, bees wax etc.

Other suitable matrix materials for slow release formulations are starch, stearin, lignin.

The formulation adjuvants suitable for the preparation of the compositions according to the invention are known per se.

As liquid carriers there may be used: water, aromatic solvents such as toluene, m-xylene, o-xylene, p-xylene and mixtures thereof, cumene, aromatic hydrocarbon blends with boiling ranges between 140 and 320° C. known under various trademarks like Solvesso®, Shellsol A®, Caromax®, Hydrosol®, paraffinic and isoparaffinic carriers such as paraffin oils, mineral oils, de-aromatized hydrocarbon solvents with boiling ranges between 50 and 320° C. known for instance under the trademark Exxsol®, non-dearomatized hydrocarbon solvents with boiling ranges between 100 and 320° C. known under the tradename Varsol®, isoparaffinic solvents with boiling ranges between 100 and 320° C. known under tradenames like Isopar® or Shellsol T®, hydrocarbons such as cyclohexane, tetrahydronaphthalene (tetralin), decahydronaphthalene, alpha-pinene, d-limonene, hexadecane, isooctane, ester solvents such as ethyl acetate, n/1-butyl acetate, amyl acetate, i-bornyl acetate, 2-ethylhexyl acetate, $C_6$-$C_{18}$ alkyl esters of acetic acid known under the tradename Exxate®, lactic acid ethylester, lactic acid propylester, lactic acid butylester, benzyl benzoate, benzyl lactate, dipropyleneglycol dibenzoate, dialkyl esters of succinic, maleic and fumaric acid and polar solvents like N-methylpyrrolidone, N-ethyl pyrrolidone, $C_3$-$C_{18}$-alkyl pyrrolidones, gamma-butyrolactone, dimethylsulfoxide, N,N-dimethylformamide, N,N-dimethylacetamide, N,N-dimethyllactamide, $C_4$-$C_{18}$ fatty acid dimethylamides, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, butylene carbonate, alcoholic solvents and diluents such as methanol, ethanol, propanol, n/iso-butanol, n/isopentanol, 2-ethyl hexanol, n-octanol, tetrahydrofurfuryl alkohol, 2-methyl-2,4-pentanediol, 4-hydroxy-4-methyl-2-pentanon, cyclohexanol, benzyl alcohol, ethylene glycol, ethylene glycol butyl ether, ethylene glycol methyl ether, diethylene glycol, diethylene glycol butyl ether, diethylene glycol ethyl ether, diethylene glycol methyl ether, propylene glycol, dipropylene glycol, dipropylene glycol methyl ether and other similar glycol ether solvents based on ethylene glycol, propylene glycol and butylene glycol feedstocks, triethylene glycol, polyethylene glycol (PEG 400), polypropylenglycols with molecular masses of 400-4000, glycerol, glycerol acetate, glycerol diacetate, glycerol triacetate, 1,4-dioxane, diethylene glycol abietate, chlorobenzene, chlorotoluene, fatty acid esters such as methyl octanoate, isopropyl myristate, methyl laurate, methyl oleate, mixture of $C_8$-$C_{10}$ fatty acid methyl esters, rape seed oil methyl and ethyl esters, soy bean oil methyl and ethyl esters, vegetable oils, fatty acids such as oleic acid, linoleic acid, linolenic acid, esters of phosphoric and phosphonic acid such as triethyl phosphate, $C_3$-$C_{18}$-trisalkyl phosphates, alkylaryl phosphates, bis-octyl-octyl phosphonates.

Water is generally the carrier of choice for the dilution of the concentrates.

Suitable solid carriers are, for example, talc, titanium dioxide, pyrophyllite clay, silica (fumed or precipated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations, especially in those formulations which can be diluted with a carrier prior to use. Surface-active substances may be anionic, cationic, amphoteric, non-ionic or polymeric and they may be used as emulsifiying, wetting, dispersing or suspending agents or for other purposes. Typical surface-active substances include, for example, salts of alkyl sulfates, such as diethanolammonium lauryl sulfate; Sodium lauryl sulfate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, compatibility agents and solubilisers and also liquid and solid fertilisers.

The formulations may also comprise additional active substances, for example further herbicides, herbicide safeners, plant growth regulators, fungicides or insecticides.

The compositions according to the invention can additionally include an additive (commonly referred to as an adjuvant), comprising a mineral oil, an oil of vegetable or animal origin, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsifiable vegetable oil, such as AMIGO® (Loveland Products Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is AGNIQUE ME 18 RD-F® (Cognis). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic, cationic or amphoteric surfactants. Examples of suitable anionic, non-ionic, cationic or amphoteric surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total additive is generally from 1 to 50% by weight. Examples of oil additives that consist of mixtures of oils or mineral oils or derivatives thereof with surfactants are TURBOCHARGE®, ADIGOR® (both (Syngenta Crop Protection AG), ACTIPRON® (BP Oil UK Limited), AGRI-DEX® (Helena Chemical Company).

The said surface-active substances may also be used in the formulations alone, that is to say without oil additives.

Furthermore, the addition of an organic solvent to the oil additive/surfactant mixture can contribute to a further enhancement of action. Suitable solvents are, for example, SOLVESSO® and AROMATIC® solvents (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF). Further oil additives that are preferred according to the invention are SCORE® and ADIGOR® (both Syngenta Crop Protection AG).

In addition to the oil additives listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

Such adjuvant oils as described in the preceding paragraphs may be employed as the carrier liquid in which an active compound is dissolved, emulsified or dispersed as appropriate to the physical form of the active compound.

The pesticidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1-2000 g/ha, preferably 1-1000 g/ha and most preferably at 1-500 g/ha.

Preferred Formulations have Especially the Following Representative Compositions:
(%=percent by weight):
Emulsifiable Concentrates:
active ingredient: 1 to 95%, preferably 60 to 90%
surface-active agents: 1 to 30%, preferably 5 to 20%
solvents as liquid carrier: 1 to 80%, preferably 1 to 35%
Dusts:
active ingredient: 0.1 to 10%, preferably 0.1 to 5%
solid carriers: 99.9% to 90%, preferably 99.9 to 99%
Suspension Concentrates:
active ingredient: 5 to 75%, preferably 10 to 50%
water: 94 to 24%, preferably 88 to 30%
surface-active agents: 1 to 40%, preferably 2 to 30%
Wettable Powders:
active ingredient: 0.5 to 90%, preferably 1 to 80%
surface-active agents: 0.5 to 20%, preferably 1 to 15
solid carriers: 5 to 95%, preferably 15 to 90%
Granules:
active ingredient: 0.1 to 30%, preferably 0.1 to 15%
solid carriers: 99.5 to 70%, preferably 97 to 85%
Waterdispersible Granules:
active ingredient: 1 to 90%, preferably 10 to 80%
surface-active agents: 0.5 to 80%, preferably 5 to 30%
solid carriers: 90 to 10%, preferably 70 to 30%

The following Examples further illustrate, but do not limit, the invention.

| F1. Emulsifiable concentrates | a) | b) | c) | d) |
| --- | --- | --- | --- | --- |
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | 10% | — | 20% |
| arom. hydrocarbon mixture $C_9$-$C_{12}$ | 85% | 68% | 65% | 16% |

Emulsions of any desired concentration can be prepared from such concentrates by dilution with water.

| F2. Solutions | a) | b) | c) | d) |
| --- | --- | --- | --- | --- |
| active ingredient | 5% | 10% | 50% | 90% |
| 1-methoxy-3-(3-methoxy-propoxy)-propane | 40% | 50% | — | — |
| polyethylene glycol MW 400 | 20% | 10% | — | — |
| NMP | — | — | 50% | 10% |
| arom. hydrocarbon mixture $C_9$-$C_{12}$ | 35% | 30% | — | — |

The solutions are suitable for application undiluted or after dilution with water.

| F3. Wettable powders | a) | b) | c) | d) |
| --- | --- | --- | --- | --- |
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
| --- | --- | --- | --- |
| active ingredient | 0.1% | 5% | 15% |
| highly dispersed silica | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silica | 0.9% | 1% | 2% |
| inorg. carrier (diameter 0.1-1 mm) e.g. CaCO$_3$ or SiO$_2$ | 98.0% | 92% | 80% |

The finely ground active ingredient is applied uniformly, in a mixer, to the carrier moistened with polyethylene glycol. Non-dusty coated granules are obtained in this manner.

| F6. Extruded granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Water-dispersible granules | a) | b) | c) | d) |
|---|---|---|---|---|
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% | |
| Sodium sulfate | | | 4% | 5% |
| kaolin | 48% | 30% | 30% | |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysacharide (Xanthan) | 0.2% | 0.2% | 0.2% | 0.2% |
| 1,2-Benzisothiazolin-3-on | 0.1% | 0.1% | 0.1% | 0.1% |
| silicone oil emulsion | 0.7% | 0.7% | 0.7% | 0.7% |
| water | 87% | 79% | 62% | 38% |

The finely ground active ingredient is intimately mixed with the adjuvants, yielding a suspension concentrate from which suspensions of any desired concentration can be prepared by dilution with water.

Crops of useful plants in which the compositions according to the invention can be used include especially cereals, in particular wheat and barley, rice, corn, rape, sugarbeet, sugarcane, soybean, cotton, sunflower, peanut and plantation crops.

The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*. Control of monocotyledonous weeds, in particular *Agrostis, Avena, Setaria, Lolium, Echinochloa, Bromus, Alopecurus* and *Sorghum* is very extensive.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with further herbicides. Preferably, in these mixtures, the compound of the formula I is one of those compounds listed in Tables 1 to 52 below. The following mixtures of the compound of formula I are especially important:
compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula 1+fenoxasulfone (CAS RN 639826-16-7), compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+ipfencarbazone (CAS RN 212201-70-2), compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+metazosulfuron (NC-620, CAS RN 868680-84-6), compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyrisulfuron (TH-547, CAS RN 570415-88-2), compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS RN 335104-84-2), compound of formula I+topramezone (CAS RN 210631-68-8), compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), and compound of formula I+4-hydroxy-3-[[2-(3-methoxypropyl)-6-(difluoromethyl)-3-pyridinyl]carbonyl]-bicyclo[3.2.1]oct-3-en-2-one.

The mixing partners for the compound of formula I may also be in the form of esters or salts, as mentioned e.g. in The Pesticide Manual, 12th Edition (BCPC) 2000.

For applications in cereals, the following mixtures are preferred: compound of formula I+aclonifen, compound of formula I+amidosulfuron, compound of formula I+aminopyralid, compound of formula I+beflubutamid, compound of formula I+benfluralin, compound of formula I+bifenox, compound of formula I+bromoxynil, compound of formula I+butafenacil, compound of formula I+carbetamide, compound of formula I+carfentrazone, compound of formula I+carfentrazone-ethyl, compound of formula I+chlorotoluron, compound of formula I+chlorpropham, compound of formula I+chlorsulfuron, compound of formula I+cinidon-ethyl, compound of formula I+clodinafop, compound of formula I+clodinafop-propargyl, compound of formula I+clopyralid, compound of formula I+2,4-D, compound of formula I+dicamba, compound of formula I+dichlobenil, compound of formula I+dichlorprop, compound of formula I+diclofop, compound of formula I+diclofop-methyl, compound of formula I+difenzoquat, compound of formula I+difenzoquat metilsulfate, compound of formula I+diflufenican, compound of formula I+diquat, compound of formula I+diquat dibromide, compound of formula I+fenoxaprop-P, compound of formula I+fenoxaprop-P-ethyl, compound of formula I+flamprop-M, compound of formula I+florasulam, compound of formula I+fluazifop-P-butyl, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+fluorochloridone, compound of formula I+fluoroxypyr, compound of formula I+flurtamone, compound of formula I+imazamethabenz-methyl, compound of formula I+imazamox, compound of formula I+iodosulfuron, compound of formula I+iodosulfuron-methyl-sodium, compound of formula I+ioxynil, compound of formula I+isoproturon, compound of formula I+linuron, compound of formula I+MCPA, compound of formula I+mecoprop, compound of formula I+mecoprop-P, compound of formula I+mesosulfuron, compound of formula I+mesosulfuron-methyl, compound of formula I+mesotrione, compound of formula I+metribuzin, compound of formula I+metsulfuron, compound of formula I+metsulfuron-methyl, compound of formula I+pendimethalin, compound of formula I+picolinafen, compound of formula I+pinoxaden, compound of formula I+prodiamine, compound of formula I+propanil, compound of formula I+propoxycarbazone, compound of formula I+propoxycarbazone-sodium, compound of formula I+prosulfocarb, compound of formula I+pyrasulfotole, compound of formula I+pyridate, compound of formula I+pyroxasulfone (KIN-485), compound of formula I+pyroxsulam compound of formula I+sulfosulfuron, compound of formula 1+tembotrione, compound of formula I+terbutryn, compound of formula I+thifensulfuron, compound of formula I+thiencarbazone, compound of formula I+thifensulfuron-methyl, compound of formula I+topramezone, compound of formula I+tralkoxydim, compound of formula I+tri-allate, compound of formula I+triasulfuron, compound of formula I+tribenuron, compound of formula I+tribenuron-methyl, compound of formula I+trifluralin, compound of formula I+trinexapac-ethyl and compound of formula I+tritosulfuron, where the mixtures comprising a compound of formula (I)+ amidosulfuron, compound of formula (I)+aminopyralid, compound of formula (I)+beflubutamid, compound of formula (I)+bromoxynil, compound of formula (I)+carfentrazone, compound of formula (I)+carfentrazone-ethyl, compound of formula (I)+chlorotoluron, compound of formula (I)+chlorsulfuron, compound of formula (I)+clodinafop, compound of formula (I)+clodinafop-propargyl, compound of formula (I)+clopyralid, 2,4-D, compound of formula (I)+ dicamba, compound of formula (I)+difenzoquat, compound of formula (I)+difenzoquat metilsulfate, compound of formula (I)+diflufenican, compound of formula (I)+fenoxaprop-P, compound of formula (I)+fenoxaprop-P-ethyl, compound of formula (I)+florasulam, compound of formula (I)+flucarbazone, compound of formula (I)+flucarbazone-sodium, compound of formula (I)+flufenacet, compound of formula (I)+flupyrsulfuron, compound of formula (I)+flupyrsulfuron-methyl-sodium, compound of formula (I)+fluoroxypyr, compound of formula (I)+flurtamone, compound of formula (I)+ iodosulfuron, compound of formula (I)+iodosulfuron-methyl-sodium, compound of formula (I)+MCPA, compound of formula (I)+mesosulfuron, compound of formula (I)+mesosulfuron-methyl, compound of formula (I)+ metsulfuron, compound of formula (I)+metsulfuron-methyl, compound of formula (I)+pendimethalin, compound of formula (I)+picolinafen, compound of formula (I)+pinoxaden, compound of formula (I)+prosulfocarb, compound of formula (I)+pyrasulfotole, compound of formula (I)+pyroxasulfone (KIH-485), compound of formula (I)+pyroxsulam, compound of formula (I)+sulfosulfuron, compound of formula (I)+thifensulfuron, compound of formula (I)+thifensulfuron-methyl, compound of formula (I)+tralkoxydim, compound of formula (I)+triasulfuron, compound of formula (I)+tribenuron, compound of formula (I)+tribenuron-methyl, compound of formula (I)+trifluralin, compound of formula (I)+trinexapac-ethyl and compound of formula (I)+tritosulfuron are particularly preferred.

For applications in rice, the following mixtures are preferred: compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+butachlor, compound of formula (I)+cafenstrole, compound of formula (I)+cinosulfuron, compound of formula (I)+clomazone, compound of formula (I)+clomeprop, compound of formula (I)+cyclosulfamuron, compound of formula (I)+cyhalofop, compound of formula (I)+cyhalofop-butyl, compound of formula (I)+2,4-D, compound of formula (I)+daimuron, compound of formula (I)+ dicamba, compound of formula (I)+diquat, compound of formula (I)+diquat dibromide, compound of formula (I)+ esprocarb, compound of formula (I)+ethoxysulfuron, compound of formula (I)+fenoxaprop-P, compound of formula (I)+fenoxaprop-P-ethyl, compound of formula 1+fenoxasulfone (CAS RN 639826-16-7), compound of formula (I)+fentrazamide, compound of formula (I)+florasulam, compound of formula (I)+glufosinate-ammonium, compound of formula (I)+glyphosate, compound of formula (I)+ halosulfuron, compound of formula (I)+halosulfuron-methyl, compound of formula (I)+imazosulfuron, compound of formula I+ipfencarbazone (CAS RN 212201-70-2), compound of formula (I)+MCPA, compound of formula (I)+ mefenacet, compound of formula (I)+mesotrione, compound of formula (I)+metamifop, compound of formula I+metazosulfuron (NC-620, CAS RN 868680-84-6), compound of formula (I)+metsulfuron, compound of formula (I)+metsulfuron-methyl, compound of formula (I)+n-methyl glyphosate, compound of formula (I)+orthosulfamuron, compound of formula (I)+oryzalin, compound of formula (I)+oxadiargyl, compound of formula (I)+oxadiazon, compound of formula (I)+paraquat dichloride, compound of formula (I)+pendimethalin, compound of formula (I)+penoxsulam, compound of formula (I)+pretilachlor, compound of formula (I)+ profoxydim, compound of formula (I)+propanil, compound of formula I+propyrisulfuron (TH-547, CAS RN 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+ trinexapac-ethyl, where the mixtures comprising a compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+clomazone, compound of formula (I)+clomeprop, compound of formula (I)+cyhalofop, compound of formula (I)+cyhalofop-butyl, compound of formula (I)+2,4-D, compound of formula (I)+daimuron, compound of formula (I)+dicamba, compound of formula (I)+esprocarb, compound of formula (I)+ethoxysulfuron, compound of formula (I)+fenoxaprop-P, compound of formula (I)+fenoxaprop-P-ethyl, compound of formula 1+fenoxasulfone (CAS RN 639826-16-7), compound of formula (I)+fentrazamide, compound of formula (I)+florasulam, compound of formula (I)+halosulfuron, compound of formula (I)+halosulfuron-methyl, compound of formula (I)+imazosulfuron, compound of formula I+ipfencarbazone (CAS RN 212201-70-2), compound of formula (I)+MCPA, compound of formula (I)+mefenacet, compound of formula (I)+mesotrione, compound of formula I+metazosulfuron (NC-620, CAS RN 868680-84-6), compound of formula (I)+metsulfuron, compound of formula (I)+metsulfuron-methyl, compound of formula (I)+orthosulfamuron, compound of formula (I)+oxadiargyl, compound of formula (I)+oxadiazon, compound of formula (I)+pendimethalin, compound of formula (I)+penoxsulam, compound of formula (I)+pretilachlor, compound of formula I+propyrisulfuron (TH-547, CAS RN 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl are particularly preferred.

The compounds of formula I according to the invention can also be used in combination with safeners. Preferably, in these mixtures, the compound of the formula I is one of those compounds listed in Tables 1 to 52 below. The following mixtures with safeners, especially, come into consideration: compound of formula I+cloquintocet-mexyl, compound of formula I+cloquintocet acid and salts thereof, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecopropand compound of the formula I+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

Benoxacor, cloquintocet-mexyl, cyprosulfamide, mefenpyr-diethyl and N-(2-methoxybenzoyl)-4-[(methylaminocarbonyl)amino]benzenesulfonamide are especially preferred, where cloquintocet-mexyl is particularly valuable.

The rate of application of safener relative to the herbicide is largely dependent upon the mode of application. In the case of field treatment, generally from 0.001 to 5.0 kg of safener/ha, preferably from 0.001 to 0.5 kg of safener/ha, and generally from 0.001 to 2 kg of herbicide/ha, but preferably from 0.005 to 1 kg/ha, are applied.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

It is preferred to apply the other herbicide together with one of the safeners mentioned above.

The following Examples illustrate the invention further but do not limit the invention.

PREPARATION EXAMPLES

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds shown below, and in Table T1 are drawn as an arbitrary single enol tautomer, but it should be inferred that this description covers both the diketone form and any possible enols which could arise through tautomerism. Where more than one tautomer is observed in proton NMR, the data shown are for the mixture of tautomers. Furthermore, some of the compounds shown below are drawn as single enantiomers for the purposes of simplicity, but unless specified as single enantiomers, these structures should be construed as representing a mixture of enantiomers in any ratio. Additionally, some of the compounds can exist as diastereoisomers, and it should be inferred that these can be present as a single diastereoisomer or as a mixture of diastereoisomers in any ratio.

Within the detailed experimental section the diketone tautomer is chosen for naming purposes, even if the predominant tautomer is the enol form.

Example 1

Preparation of meso-(1R,2S,6R,7S)-4-(4-[4-bromo-2-fluorophenoxy]-2,6-dimethylphenyl)-10-oxatricyclo[5.2.1.0$^{2,6}$]decane-3,5-dione

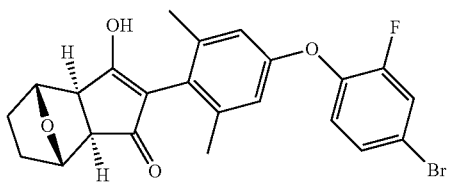 [SMILES: Cc1cc(Oc2ccc(Br)cc2F)cc(C)c1C1=C(O)[C@H]2[C@@H](C1=O)[C@@H]1CC[C@H]2O1]

Step 1: Preparation of ([4-bromo-2,6-dimethylphenyl]furan-2-yl)methanol

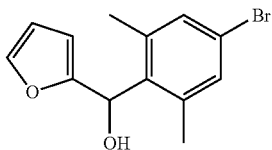 [SMILES: Cc1cc(Br)cc(C)c1C(O)c1ccco1]

4-Bromo-2,6-dimethyl-1-iodobenzene (5 g, 16 mmol) is dissolved in dry tetrahydrofuran (20 ml) and cooled to −78° C. under an atmosphere of dry nitrogen. Isopropylmagnesium chloride (2M solution in tetrahydrofuran, 10 ml, 20 mmol) is added dropwise with vigorous stirring over 30 minutes. When the addition is complete, the reaction is allowed to warm to room temperature and is stirred for 30 minutes at room temperature. The reaction mixture is cooled to −78° C. and a solution of 2-furaldehyde (2.4 g, 25 mmol) in dry tetrahydrofuran (10 ml) is added dropwise over 30 minutes. Once the addition is complete, the mixture is allowed to warm to room temperature and stirring continued for 2 hours. A solution of saturated aqueous ammonium chloride (30 ml). is added, and the mixture is extracted with dichloromethane (3×25 ml). The organic extracts are combined, washed with brine, dried over anhydrous magnesium sulfate, filtered and the filtrate is evaporated under reduced pressure. The residue is purified by column chromatography on silica gel to give ([4-bromo-2,6-dimethylphenyl]furan-2-yl)methanol (3.71 g).

Step 2: Preparation of 5-(4-bromo-2,6-dimethylphenyl)-4-hydroxycyclopent-2-enone

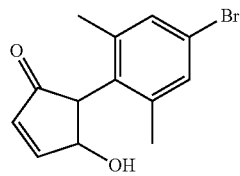 [SMILES: Cc1cc(Br)cc(C)c1C1C(=O)C=CC1O]

Polyphosphoric acid (500 mg) is added to a warm (55° C.) solution of ([4-bromo-2,6-dimethylphenyl]furan-2-yl)methanol (843 mg, 3 mmol) in acetone (8 ml) and water (2 ml) and the mixture is heated at 55° C. for 24 hours. The mixture is cooled to room temperature and the acetone is removed under reduced pressure. The remaining mixture is partitioned between diethyl ether (20 ml) and water (20 ml). The aqueous phase is extracted with ether (2×50 ml), and then the organic phases are combined, washed with saturated aqueous sodium bicarbonate solution (20 ml), and brine (20 ml), dried over anhydrous magnesium sulfate, filtered and the filtrate is evaporated under reduced pressure. The residue is purified by column chromatography on silica gel to give 5-(4-bromo-2,6-dimethylphenyl)-4-hydroxycyclopent-2-enone (596 mg).

Step 3: Preparation of 2-(4-bromo-2,6-dimethylphenyl)cyclopent-4-ene-1,3-dione

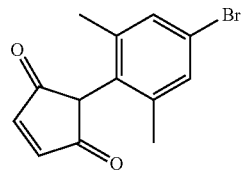 [SMILES: Cc1cc(Br)cc(C)c1C1C(=O)C=CC1=O]

To a solution of 5-(4-bromo-2,6-dimethylphenyl)-4-hydroxycyclopent-2-enone (18.33 g. 65 mmol) in acetone (200 ml) at 0° C. is added, dropwise, a solution of Jones reagent (1.67 M, 39 ml, 65 mmol) and the resulting yellow solution is stirred at 0° C. for 90 minutes. The reaction is quenched by the addition of propan-2-ol (1 ml) and stirred for a further 2 hours. Brine (300 ml) is added and the reaction is extracted with ethyl acetate (3×250 ml). The organic extracts are combined, washed with brine, dried over anhydrous magnesium sulfate, filtered and the filtrate is concentrated under reduced pressure. The residue is purified by column chromatography on silica gel to give 2-(4-bromo-2,6-dimethylphenyl)cyclopent-4-ene-1,3-dione (17.2 g).

Step 4: Preparation of meso-(1R,2S,6R,7S)-4-(4-bromo-2,6-dimethylphenyl)-10-oxatricyclo[5.2.1.0$^{2,6}$]dec-8-ene-3,5-dione

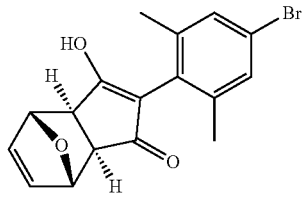 [SMILES: Cc1cc(Br)cc(C)c1C1=C(O)[C@H]2[C@@H](C1=O)[C@@H]1C=C[C@H]2O1]

A suspension of 2-(4-bromo-2,6-dimethylphenyl)cyclopent-4-ene-1,3-dione (30 g, 107 mmol) in furan (250 ml) is stirred at room temperature for 13 days. The reaction mixture is diluted with methanol (200 ml) and silica gel is added. The solvent is evaporated under reduced pressure, and the residue is purified by column chromatography on silica gel to give meso-(1R,2S,6R,7S)-4-(4-bromo-2,6-dimethylphenyl)-10-oxatricyclo[5.2.1.0$^{2,6}$]dec-8-ene-3,5-dione (18.4 g).

Step 5: Preparation of meso-(1R,2S,6R,7S)-4-(4-bromo-2,6-dimethylphenyl)-10-oxatricyclo[5.2.1.0$^{2,6}$]decane-3,5-dione

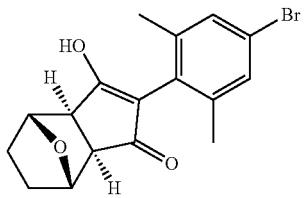 [SMILES: Cc1cc(Br)cc(C)c1C1=C(O)[C@H]2[C@@H](C1=O)[C@@H]1CC[C@H]2O1]

To a suspension of nickel(II) acetate tetrahydrate (4.98 g, 20 mmol) in ethanol (100 ml) is added, under vigorous stirring, sodium borohydride (760 mg, 20 mmol). The reaction mixture is stirred under nitrogen for 5 minutes, then under hydrogen for 10 min. Under vigorous stirring a suspension of (1RS,2SR,6RS,7SR)-4-(4-bromo-2,6-dimethylphenyl)-10-oxatricyclo[5.2.1.0$^{2,6}$]-dec-8-ene-3,5-dione (6.94 g, 20 mmol) in ethanol (100 ml) is added. The mixture is stirred under hydrogen for 2 hours, then filtered through a plug of diatomaceous earth. The filtrate is evaporated. The residue is partitioned between ethyl acetate (300 ml) and 0.5 N aqueous hydrochloric acid (400 ml), and the aqueous phase is extracted with ethyl acetate (2×200 ml). The organic phases are combined, dried over anhydrous magnesium sulfate, filtered and the filtrate is evaporated under reduced pressure to give 6.8 g of meso-(1R,2S,6R,7S)-4-(4-bromo-2,6-dimethylphenyl)-10-oxa-tricyclo[5.2.1.0$^{2,6}$]decane-3,5-dione (6.8 g).

Step 6: Preparation of meso-(1R,2S,6R,7S)-4-(4-[4-bromo-2-fluorophenoxy]-2,6-dimethylphenyl)-10-oxatricyclo[5.2.1.0$^{2,6}$]decane-3,5-dione

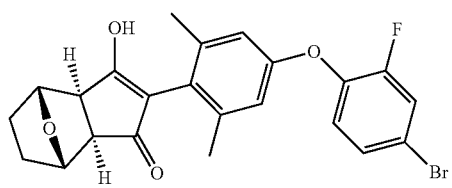 [SMILES: Cc1cc(Oc2ccc(Br)cc2F)cc(C)c1C1=C(O)[C@H]2[C@@H](C1=O)[C@@H]1CC[C@H]2O1]

A mixture of meso-(1R,2S,6R,7S)-4-(4-bromo-2,6-dimethylphenyl)-10-oxatricyclo[5.2.1.0$^{2,6}$]decane-3,5-dione (400 mg, 1.15 mmol), 4-bromo-2-fluorophenol (262 mg, 137 mmol), cesium carbonate (750 mg, 2.30 mmol), copper(II) trifluoromethanesulfonate (22 mg, 0.06 mmol) and ethyl acetate (4 mg, 0.06 mmol) are stirred together in dry toluene (10 ml) under an atmosphere of nitrogen, and then heated to reflux for 18 hours. The mixture is cooled to room temperature, N,N-dimethylformamide (2 ml) and 2M aqueous hydrochloric acid (10 ml) are added and the mixture is stirred vigorously for 45 minutes. The mixture is extracted with ethyl acetate (3×10 ml), and the organic extracts are combined, dried over anhydrous magnesium sulfate, filtered and the filtrate is evaporated under reduced pressure. The residue is purified by preparative reverse phase HPLC to give meso-(1R,2S,6R,7S)-4-(4-[4-bromo-2-fluorophenoxy]-2,6-dimethylphenyl)-10-oxatricyclo[5.2.1.0$^{2,6}$]decane-3,5-dione.

Example 2

Preparation of rac-(1R,2S,6R,7S)-4-(2,6-dimethyl-4-[2-fluoro-4-nitro-phenoxy]phenyl-5-oxo-10-oxatricyclo[5.2.1.0$^{2,6}$]dec-3-en-3-yl 2,2-dimethylpropionate

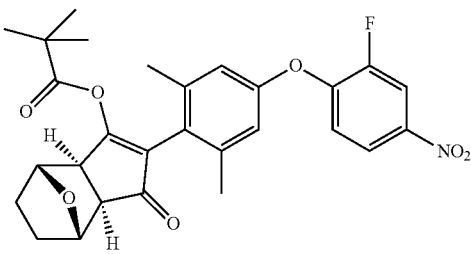 [SMILES: Cc1cc(Oc2ccc([N+](=O)[O-])cc2F)cc(C)c1C1=C(OC(=O)C(C)(C)C)[C@H]2[C@@H](C1=O)[C@@H]1CC[C@H]2O1]

Step 1: Preparation of 4-benzyloxy-2,6-dimethylbenzaldehyde

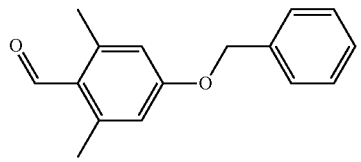 [SMILES: Cc1cc(OCc2ccccc2)cc(C)c1C=O]

To a solution of 2,6-dimethyl-4-hydroxybenzaldehyde (15 g, 100 mmol) in dimethylformamide (200 ml) is added potassium carbonate (27.6 g, 200 mmol) and benzyl bromide (14.3 ml, 120 mmol). The reaction mixture is stirred at room temperature for 17 hours. The reaction mixture is filtered and the filtrate is evaporated under reduced pressure. The residue is purified by column chromatography on silica gel to give 4-benzyoxy-2,6-dimethylbenzaldehyde (23.0 g).

Step 2: Synthesis of ([4-benzyloxy-2,6-dimethylphenyl]furan-2-yl)methanol

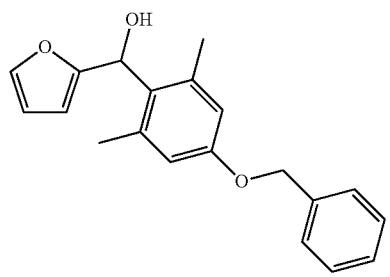 [SMILES: Cc1cc(OCc2ccccc2)cc(C)c1C(O)c1ccco1]

To a solution of furan (10.9 ml, 150 mmol) in dry tetrahydrofuran (200 ml) is added dropwise, under nitrogen, n-butyllithium (2.5 M solution in hexane, 50 ml, 125 mmol) at −78° C. When the addition is complete, the reaction is stirred for 30 minutes at −78° C. A solution of 4-benzyloxy-2,6-dimethylbenzaldehyde (23.0 g, 96 mmol) in dry tetrahydrofuran (100 ml) is added dropwise over 30 minutes. On completion of the addition, the reaction is allowed to warm to room temperature and stirring is continued for 2 hours. A solution of saturated aqueous ammonium chloride solution (300 ml) is added and the reaction mixture is extracted with dichloromethane (3×250 ml). The organic extract are combined, washed with brine, dried over anhydrous magnesium sulfate, filtered and the filtrate is evaporated under reduced pressure. The product, ([4-benzyloxy-2,6-dimethylphenyl]furan-2-yl)methanol (32 g) is used without further purification in the next step.

Step 3: Synthesis of 5-(4-benzyloxy-2,6-dimethylphenyl)-4-hydroxycyclopent-2-enone

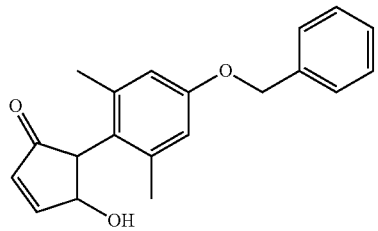 [SMILES: Cc1cc(OCc2ccccc2)cc(C)c1C1C(=O)C=CC1O]

Polyphosphoric acid (5 g) is added to a warm (55° C.) solution of ([4-benzyloxy-2,6-dimethylphenyl]furan-2-yl) methanol (32 g) in a mixture of acetone (400 ml) and water (100 ml) and the mixture is heated at 55° C. for 20 hours. The reaction mixture is cooled to room temperature and most of the acetone is removed under reduced pressure. The mixture is extracted with diethyl ether (3×250 ml), and the organic fractions are washed with saturated aqueous sodium bicarbonate solution (2×200 ml), dried over anhydrous magnesium sulfate, filtered and the filtrate is evaporated under reduced pressure. The crude product (30.9 g) is used for the next step without further purification.

Step 4: Synthesis of 2-(4-benzyloxy-2,6-dimethylphenyl)cyclopent-4-ene-1,3-dione

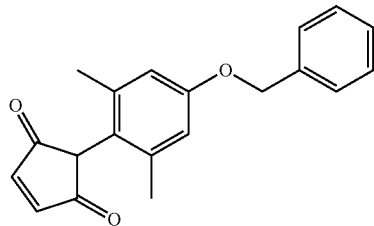 [SMILES: Cc1cc(OCc2ccccc2)cc(C)c1C1C(=O)C=CC1=O]

A solution of Jones reagent (1.67 M, 60 ml, 100 mmol) is added, dropwise, to a solution of 5-(4-benzyloxy-2,6-dimethylphenyl)-4-hydroxycyclopent-2-enone (30.9 g) in acetone (500 ml) at 0° C., and the resulting solution is stirred at 0° C. for 2 hours. Propan-2-ol (50 ml) is added and the mixture is stirred for a further 2 hours, then brine (200 ml) is added and the reaction mixture is extracted with ethyl acetate (2×250 ml). The organic extracts are combined, washed with brine, dried over anhydrous magnesium sulfate, filtered and the filtrate is concentrated under reduced pressure. The residue is purified by column chromatography on silica gel to give 2-(4-benzyloxy-2,6-dimethylphenyl)cyclopent-4-ene-1,3-dione (18.1 g).

Step 5: Synthesis of meso-(1R,2S,6R,7S)-4-(4-benzyloxy-2,6-dimethylphenyl)-10-oxatricyclo[5.2.1.0$^{2,6}$]dec-8-ene-3,5-dione

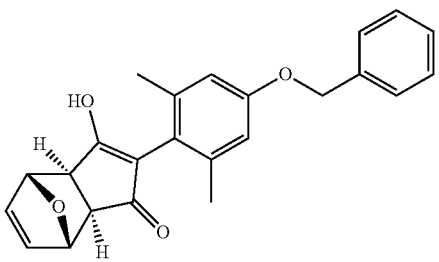 [SMILES: Cc1cc(OCc2ccccc2)cc(C)c1C1=C(O)[C@H]2[C@@H](C1=O)[C@@H]1C=C[C@H]2O1]

A suspension of 2-(4-benzyloxy-2,6-dimethylphenyl)cyclopent-4-ene-1,3-dione (1 g, 3.3 mmol), furan (20 ml) and magnesium iodide (50 mg) is stirred at room temperature for 5 days. The reaction mixture is diluted with methanol and silica gel is added. After evaporation of the solvent, the residue is purified by column chromatography on silica gel to give 4-(4-benzyloxy-2,6-dimethylphenyl)-10-oxatricyclo [5.2.1.0$^{2,6}$]dec-8-ene-3,5-dione (0.531 g).

Step 6: Synthesis of rac-(1R,2S,6R,7S)-4-(4-benzyloxy-2,6-dimethylphenyl)-5-oxo-10-oxatricyclo [5.2.1.0$^{2,6}$]deca-3,8-dien-3-yl-2,2-dimethylpropionate

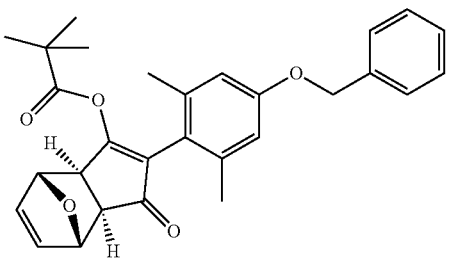 [SMILES: Cc1cc(OCc2ccccc2)cc(C)c1C1=C(OC(=O)C(C)(C)C)[C@H]2[C@@H](C1=O)[C@@H]1C=C[C@H]2O1]

Triethylamine (5 ml, 35.9 mmol) is added, dropwise, to a solution of 4-(4-benzyloxy-2,6-dimethylphenyl)-10-oxatricyclo[5.2.1.0$^{2,6}$]dec-8-ene-3,5-dione (5.0 g, 13.4 mmol) and trimethylacetyl chloride (5 ml, 40.6 mmol) in dry dichloromethane (75 ml). The mixture is stirred for 2 hours at room temperature, then silica gel is added and the solvent is evaporated under reduced pressure. The residue is purified by column chromatography on silica gel to give rac-(1R,2S,6R,7S)-

4-(4-benzyloxy-2,6-dimethylphenyl)-5-oxo-10-oxatricyclo[5.2.1.0²,⁶]deca-3,8-dien-3-yl 2,2-dimethylpropionate.

Step 7: Synthesis of rac-(1R,2S,6R,7S)-4-(4-benzyloxy-2,6-dimethylphenyl-4-hydroxy)-5-oxo-10-oxatricyclo[5.2.1.0²,⁶]dec-3-en-3-yl 2,2-dimethylpropionate

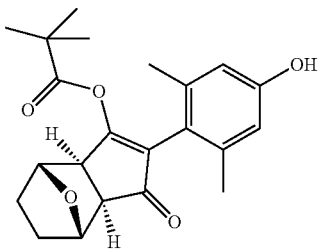 [SMILES: Cc1cc(O)cc(C)c1C1=C(OC(=O)C(C)(C)C)[C@H]2[C@@H](C1=O)[C@@H]1CC[C@H]2O1]

10% Palladium on carbon (~0.2 g) is added to a solution of rac-(1R,2S,6R,7S)-4-(4-benzyloxy-2,6-dimethylphenyl)-5-oxo-10-oxatricyclo[5.2.1.0²,⁶]deca-3,8-dien-3-yl 2,2-dimethylpropionate in a mixture of ethanol (20 ml) and ethyl acetate (70 ml) and the mixture is hydrogenated at 2 bar for 3 hours. The mixture is filtered through diatomaceous earth, and the filtrate is evaporated under reduced pressure to give rac-(1R,2S,6R,7S)-4-(4-benzyloxy-2,6-dimethylphenyl-4-hydroxy)-5-oxo-10-oxatricyclo[5.2.1.0²,⁶]dec-3-en-3-yl 2,2-dimethylpropionate.

Step 8: Synthesis of rac-(1R,2S,6R,7S)-4-(2,6-dimethyl-4-[2-fluoro-4-nitrophenoxy]phenyl-5-oxo-10-oxatricyclo[5.2.1.0²,⁶]dec-3-en-3-yl 2,2-dimethylpropionate

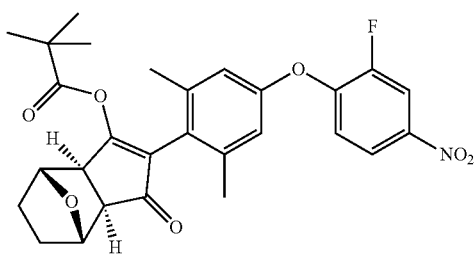 [SMILES: Cc1cc(Oc2ccc([N+](=O)[O-])cc2F)cc(C)c1C1=C(OC(=O)C(C)(C)C)[C@H]2[C@@H](C1=O)[C@@H]1CC[C@H]2O1]

A mixture of rac-(1R,2S,6R,7S)-4-(4-benzyloxy-2,6-dimethylphenyl-4-hydroxy)-5-oxo-10-oxatricyclo[5.2.1.0²,⁶]dec-3-en-3-yl 2,2-dimethylpropionate (300 mg, 0.81 mmol), 3,4-difluoronitrobenzene (154 mg, 0.97 mmol) and potassium carbonate (224 mg, 1.62 mmol) in N,N-dimethylformamide (5 ml) is heated at 80° C. for 23 hours. The mixture is cooled to room temperature, a further quantity of 3,4-difluoronitrobenzene (258 mg, 1.62 mmol) is added and the mixture is heated at 100° C. for 7 hours. The mixture is cooled to room temperature, and partitioned between 2 M aqueous hydrochloric acid (20 ml) and ethyl acetate (2×10 ml). The organic extracts are combined, dried over anhydrous magnesium sulfate, filtered and the filtrate is evaporated under reduced pressure. The residue is purified by column chromatography on silica gel to give rac-(1R,2S,6R,7S)-4-(2,6-dimethyl-4-[2-fluoro-4-nitrophenoxy]phenyl-5-oxo-10-oxatricyclo[5.2.1.0²,⁶]dec-3-en-3-yl 2,2-dimethylpropionate.

Example 3

Preparation of meso-(3aS,4S,7R,7aR)-2-[2,6-dimethyl-4-(5-trifluoromethylpyridin-2-yloxy)phenyl]-hexahydro-4,7-methanoindene-1,3-dione

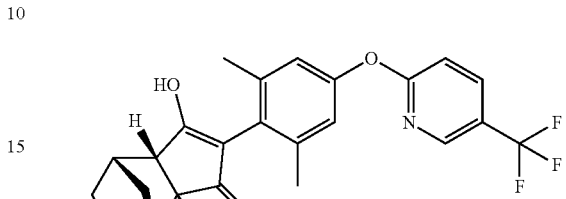

Step 1: Preparation of meso-(3aS,4R,7S,7aR)-2-(4-benzyloxy-2,6-dimethylphenyl)-3a,4,7,7a-tetrahydro-4,7-methanoindene-1,3-dione

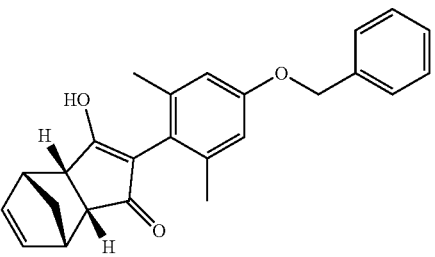 [SMILES: Cc1cc(OCc2ccccc2)cc(C)c1C1=C(O)[C@@H]2[C@H](C1=O)[C@@H]1C=C[C@H]2C1]

To stirred 2-(4-benzyloxy-2,6-dimethylphenyl)cyclopent-4-ene-1,3-dione (5.00 g, 0.0163 mol) at 0° C. is added freshly distilled/cracked cyclopentadiene (approx 40 ml), followed by additional stirring at this temperature for 2 hours, then at room temperature for 2 days. The resulting suspension is filtered, and the solid is washed with hexane and diethyl ether then dried under vacuum to afford meso-(3aS,4R,7S,7aR)-2-(4-benzyloxy-2,6-dimethylphenyl)-3a,4,7,7a-tetrahydro-4,7-methanoindene-1,3-dione.

Step 2: Preparation of meso-(3aS,4S,7R,7aR)-2-(4-hydroxy-2,6-dimethylphenyl)hexahydro-4,7-methanoindene-1,3-dione

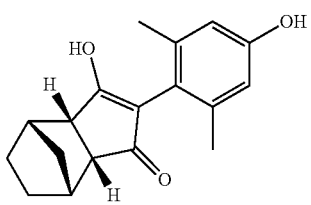 [SMILES: Cc1cc(O)cc(C)c1C1=C(O)[C@H]2[C@H]3CC[C@H](C3)[C@H]2C1=O]

To a solution of meso-(3aS,4R,7S,7aR)-2-(4-benzyloxy-2,6-dimethylphenyl)-3a,4,7,7a-tetrahydro-4,7-methanoindene-1,3-dione (approximately 1.70 g) in anhydrous methanol (250 ml) is added 5% palladium on carbon (0.20 g), and the suspension is stirred under 4 bar hydrogen pressure for 3.5 hours. The reaction mixture is then filtered through celite and the filtrate is evaporated under reduced pressure. The crude product is triturated with diethyl ether to afford meso-(3aS, 4S,7R,7aR)-2-(4-hydroxy-2,6-dimethylphenyl)hexahydro-4,7-methanoindene-1,3-dione as a pink solid.

Step 3: Preparation of meso-(3aS,4S,7R,7aR)-2-[2,6-dimethyl-4-(5-trifluoromethylpyridin-2-yloxy)phenyl]-hexahydro-4,7-methanoindene-1,3-dione

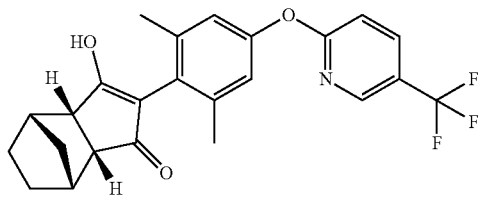 [SMILES: Cc1cc(Oc2ccc(C(F)(F)F)cn2)cc(C)c1C1=C(O)[C@H]2[C@H]3CC[C@H](C3)[C@H]2C1=O]

To a mixture of meso-(3aS,4S,7R,7aR)-2-(4-hydroxy-2,6-dimethylphenyl)hexahydro-4,7-methanoindene-1,3-dione (0.20 g, 0.0007 mol), 2-fluoro-5-trifluoromethylpyridine (0.116 g, 0.0007 mol) and potassium carbonate (0.20 g, 0.00087 mol) is added N,N-dimethylaminopyridine (7 ml), and the reaction mixture is then heated at 140° C. for 40 minutes under microwave irradiation. After cooling to room temperature 2M aqueous hydrochloric acid is added, and the crude product is extracted with dichloromethane. The organic phase is separated, washed with distilled water, then dried over magnesium sulfate and concentrated in vacuo. The residue is then dissolved again in diethyl ether, washed with distilled water, dried over anhydrous magnesium sulfate and concentrated in vacuo. The crude product is finally loaded onto silica and purified by flash column chromatography (methanol/dichloromethane eluant) to afford meso-(3aS,4S, 7R,7aR)-2-[2,6-dimethyl-4-(5-trifluoromethylpyridin-2-yloxy)phenyl]-hexahydro-4,7-methanoindene-1,3-dione as a white solid.

Example 4

Preparation of 2-[4-(5-chloro-3-fluoropyridin-2-yloxy)-2,6-dimethylphenyl]hexahydro-4,7-ethanoindene-1,3-dione

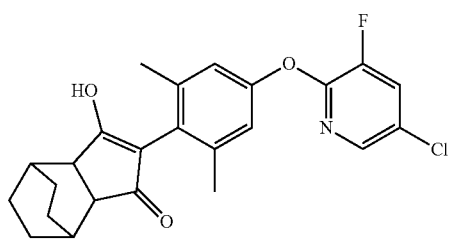 [SMILES: Cc1cc(Oc2ncc(Cl)cc2F)cc(C)c1C1=C(O)C2C3CCC(CC3)C2C1=O]

Step 1: Preparation of meso-(3aR,4R,7S,7aS)-2-(4-benzyloxy-2,6-dimethylphenyl)-3a,4,7,7a-tetrahydro-4,7-ethanoindene-1,3-dione

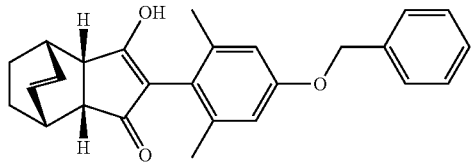 [SMILES: Cc1cc(OCc2ccccc2)cc(C)c1C1=C(O)[C@@H]2[C@H](C1=O)[C@H]1C=C[C@@H]2CC1]

A mixture of 2-(4-benzyloxy-2,6-dimethylphenyl)cyclopent-4-ene-1,3-dione (5.00 g, 0.0163 mol), cyclohexa-1,3-diene (15 mls, 0.16 mol) and magnesium iodide (1.4 g, 0.005 mol) is heated at 80° C. for 20 hours, then allowed to cool to room temperature. After dilution with methanol (100 ml) the suspension is filtered and the filtrate is evaporated to dryness. The crude solid is dissolved in methanol, absorbed onto silica and purified by flash column chromatography (3:97 methanol/dichloromethane eluant ratio) to afford meso-(3aR,4R, 7S,7aS)-2-(4-benzyloxy-2,6-dimethylphenyl)-3a,4,7,7a-tetrahydro-4,7-ethanoindene-1,3-dione.

Step 2: Preparation of 2-(4-benzyloxy-2,6-dimethylphenyl)-hexahydro-4,7-ethanoindene-1,3-dione

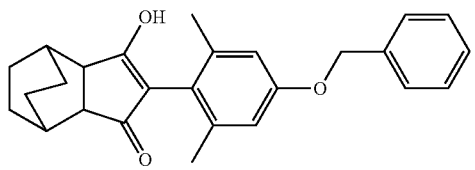 [SMILES: Cc1cc(OCc2ccccc2)cc(C)c1C1=C(O)C2C3CCC(CC3)C2C1=O]

A suspension of meso-(3aR,4R,7S,7aS)-2-(4-benzyloxy-2,6-dimethylphenyl)-3a,4,7,7a-tetrahydro-4,7-ethanoindene-1,3-dione (3.0 g, 0.008 mol) and 10% palladium on carbon (0.50 g) in methanol (230 ml) is stirred under a 4 bar hydrogen atmosphere for 3.5 hours. The mixture is then filtered through a pad of diatomaceous earth and the filtrate is evaporated under reduced pressure to afford 2-(4-benzyloxy-2,6-dimethylphenyl)hexahydro-4,7-ethanoindene-1,3-dione.

Step 3: Preparation of 2,2-dimethylpropionic acid 2-(4-benzyloxy-2,6-dimethylphenyl)-3-oxo-3a,4,5,6, 7,7a-hexahydro-3H-4,7-ethanoinden-1-yl ester

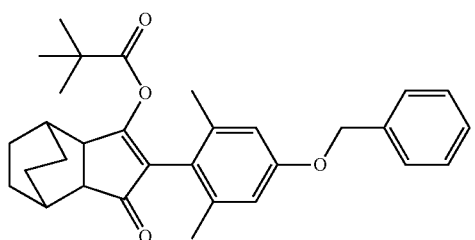

A mixture of 2-(4-benzyloxy-2,6-dimethylphenyl)hexahydro-4,7-ethanoindene-1,3-dione (2.9 g, 0.008 mol), pivaloyl chloride (1.5 ml, 0.012 mol), triethylamine (2 ml, 0.0014 mol) and dichloromethane (100 ml) is stirred at room temperature for 3 hours. The reaction mixture is next evaporated and the crude product is dissolved in dichloromethane, absorbed on to silica then purified by flash column chromatography (20% ethyl acetate in hexanes as eluant) to afford 2,2-dimethylpropionic acid 2-(4-benzyloxy-2,6-dimethylphenyl)-3-oxo-3a,4,5,6,7,7a-hexahydro-3H-4,7-ethanoinden-1-yl ester.

Step 4: Preparation of 2,2-dimethylpropionic acid 2-(4-hydroxy-2,6-dimethylphenyl)-3-oxo-3a,4,5,6,7,7a-hexahydro-3H-4,7-ethanoinden-1-yl ester

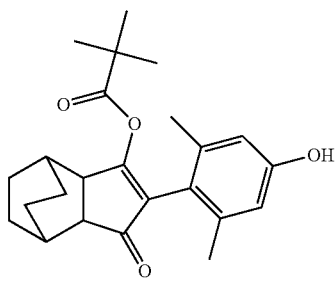 [SMILES: Cc1cc(O)cc(C)c1C1=C(OC(=O)C(C)(C)C)C2C3CCC(CC3)C2C1=O]

To a solution of 2,2-dimethylpropionic acid 2-(4-benzyloxy-2,6-dimethylphenyl)-3-oxo-3a,4,5,6,7,7a-hexahydro-3H-4,7-ethanoinden-1-yl ester (2.8 g, 0.006 mol) in methanol (250 ml) is added 10% palladium on carbon (0.50 g), and the suspension is stirred under a 4 bar hydrogen pressure for 5 hours. The reaction mixture is then filtered through a pad of diatomaceous earth and the filtrate is evaporated under reduced pressure. The crude product is triturated with diethyl ether to afford 2,2-dimethylpropionic acid 2-(4-hydroxy-2,6-dimethylphenyl)-3-oxo-3a,4,5,6,7,7a-hexahydro-3H-4,7-ethanoinden-1-yl ester.

Step 5 Preparation of 2-(4-hydroxy-2,6-dimethylphenyl)hexahydro-4,7-ethanoindene-1,3-dione

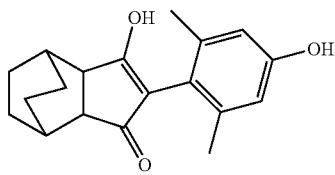 [SMILES: Cc1cc(O)cc(C)c1C1=C(O)C2C3CCC(CC3)C2C1=O]

To a solution of 2,2-dimethylpropionic acid 2-(4-hydroxy-2,6-dimethylphenyl)-3-oxo-3a,4,5,6,7,7a-hexahydro-3H-4,7-ethanoinden-1-yl ester (1.3 g, 0.0034 mol) in methanol (50 ml) is added potassium carbonate (2.35 g, 0.017 mol), and the suspension is stirred at room temperature for 2 hours. The reaction mixture is carefully acidified with 2M hydrochloric acid and extracted with ethyl acetate. The organics are separated, dried over anhydrous magnesium sulfate, filtered and the filtrate is evaporated to afford 2-(4-hydroxy-2,6-dimethylphenyl)hexahydro-4,7-ethanoindene-1,3-dione as a white solid.

Step 6: Preparation of 2-[4-(5-chloro-3-fluoropyridin-2-yloxy)-2,6-dimethylphenyl]hexahydro-4,7-ethanoindene-1,3-dione

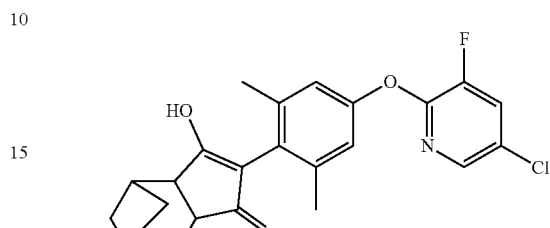

To a mixture of 2-(4-hydroxy-2,6-dimethylphenyl)hexahydro-4,7-ethanoindene-1,3-dione (0.40 g, 0.0013 mol), 5-chloro-2,3-difluoropyridine (0.20 g, 0.0013 mol) and potassium carbonate (0.40 g, 0.0029 mol) is added N,N-dimethylaminopyridine (10 ml), and the reaction mixture is then heated at 140° C. for 40 minutes under microwave irradiation. After cooling to room temperature 2M aqueous hydrochloric acid is added, and the crude product is extracted with ethyl acetate. The organic phase is separated, washed with distilled water, then dried over anhydrous magnesium sulfate and concentrated in vacuo. The residue is then purified by preparative reverse phase HPLC to afford 2-[4-(5-chloro-3-fluoropyridin-2-yloxy)-2,6-dimethylphenyl]hexahydro-4,7-ethanoindene-1,3-dione as a cream solid.

Example 5

Preparation of 2-[4-(6-chloroquinolin-2-yloxy)-2,6-dimethylphenyl]-4-(tetrahydropyran-4-ylmethyl)cyclopentane-1,3-dione

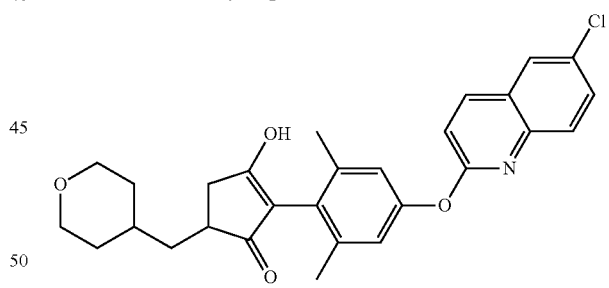

Step 1: Preparation of 2-(4-benzyloxy-2,6-dimethylphenyl)-3-methoxycyclopent-2-enone

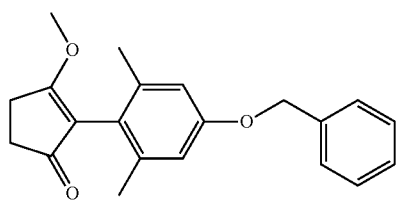 [SMILES: COC1=C(c2c(C)cc(OCc3ccccc3)cc2C)C(=O)CC1]

To a suspension of 2-bromo-3-methoxycyclopent-2-enone (5.00 g, 26.0 mmol), 4-benzyloxy-2,6-dimethylphenyl boronic acid (7.20 g, 28 mmol) (described in EP1726580) and potassium phosphate (9.55 g, 45 mmol) in degassed toluene (125 ml) is added palladium (II) acetate (0.135 g, 0.6 mmol) and 2-dicyclohexylphosphino-2',6'-dimethoxybiphenyl (0.492 g, 1.2 mmol). The reaction mixture is then heated at 90° C. under a nitrogen atmosphere for 4 hours, then allowed to cool to room temperature. After partitioning between ethyl acetate (500 ml) and distilled water (500 ml), the organic phase is separated and concentrated in vacuo. The crude product is purified by flash column chromatography (ethyl acetate/hexane eluant) to afford 2-(4-benzyloxy-2,6-dimethylphenyl)-3-methoxycyclopent-2-enone as a white solid.

Step 2: Preparation of 2-(4-benzyloxy-2,6-dimethylphenyl)-3-methoxy-5-[1-(tetrahydropyran-4-yl)-methylidene]cyclopent-2-enone

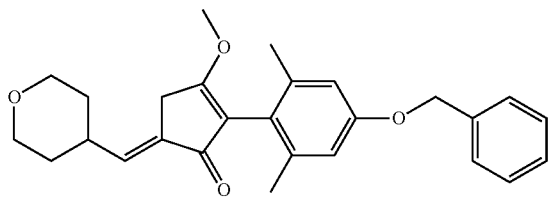 [SMILES: COC1=C(c2c(C)cc(OCc3ccccc3)cc2C)C(=O)/C(=C/C2CCOCC2)C1]

To a solution of 2-(4-benzyloxy-2,6-dimethylphenyl)-3-methoxycyclopent-2-enone (1.93 g, 6.0 mmol) in THF (25 ml) under a nitrogen atmosphere at −78° C. is added a solution of lithium diisopropylamide (3.33 ml, 6.0 mmol, 1.8M in tetrahydrofuran) dropwise over 1 minute. The reaction is then stirred at −78° C. for 30 minutes followed by the addition of 4-tetrahydropyran carbaldehyde (0.684 g, 6.0 mmol) in one portion. After a further 5 minutes at −78° C. the reaction is allowed to warm to ambient temperature and stir for an additional 1 hour. Potassium tert-butoxide (1.10 g, 9.82 mmol) is then added in one portion and the reaction mixture is allowed to stir for a further 1 hour at room temperature. After quenching with saturated ammonium chloride solution (50 ml) the crude product is extracted into ethyl acetate (50 ml), and the organic phase is dried over anhydrous magnesium sulfate and concentrated in vacuo. Purification by flash column chromatography affords 2-(4-benzyloxy-2,6-dimethylphenyl)-3-methoxy-5-[1-(tetrahydropyran-4-yl)-methylidene]cyclopent-2-enone as a white solid.

Step 3: Preparation of 2-(4-hydroxy-2,6-dimethylphenyl)-3-methoxy-5-(tetrahydropyran-4-ylmethyl)cyclopent-2-enone

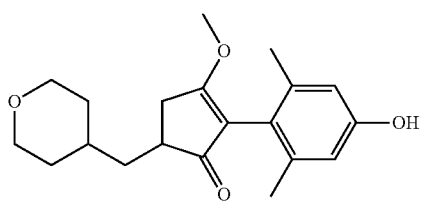 [SMILES: COC1=C(c2c(C)cc(O)cc2C)C(=O)C(CC2CCOCC2)C1]

To a solution of 2-(4-benzyloxy-2,6-dimethylphenyl)-3-methoxycyclopent-2-enone (1.50 g, 3.59 mmol) in ethanol (10 ml) is added 5% palladium on carbon (0.150 g), and the suspension is stirred for 4 hours under a 4 bar hydrogen atmosphere. The reaction mixture is then filtered through diatomaceous earth, and the filtrate is concentrated in vacuo then purified by flash column chromatography to afford 2-(4-hydroxy-2,6-dimethylphenyl)-3-methoxy-5-(tetrahydropyran-4-ylmethyl)cyclopent-2-enone.

Step 4: Preparation of 2-(4-hydroxy-2,6-dimethylphenyl)-4-(tetrahydropyran-4-ylmethyl)-cyclopentane-1,3-dione

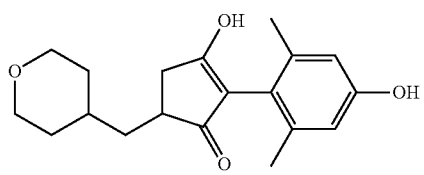 [SMILES: Cc1cc(O)cc(C)c1C1=C(O)CC(CC2CCOCC2)C1=O]

A solution of 2-(4-hydroxy-2,6-dimethylphenyl)-3-methoxy-5-(tetrahydropyran-4-ylmethyl)cyclopent-2-enone (0.375 g, 0.0014 mol) in a mixture of 2M hydrochloric acid (3 ml) and acetone (5 ml) is heated at 120° C. for 30 minutes under microwave irradiation. The reaction mixture is concentrated in vacuo then azeotroped with toluene to afford 2-(4-hydroxy-2,6-dimethylphenyl)-4-(tetrahydropyran-4-ylmethyl)cyclopentane-1,3-dione as a cream solid.

Step 5: Preparation of 2-[4-(6-chloroquinolin-2-yloxy)-2,6-dimethylphenyl]-4-(tetrahydropyran-4-ylmethyl)cyclopentane-1,3-dione

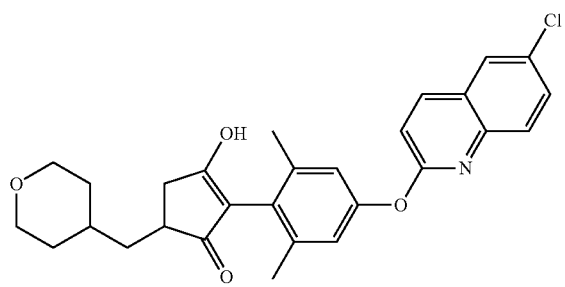 [SMILES: Cc1cc(Oc2ccc3cc(Cl)ccc3n2)cc(C)c1C1=C(O)CC(CC2CCOCC2)C1=O]

A suspension of 2-(4-hydroxy-2,6-dimethylphenyl)-4-(tetrahydropyran-4-ylmethyl)cyclopentane-1,3-dione (0.104 g, 0.00033 mol), 2,6-dichloroquinoline (0.065 g, 0.00033 mol) and potassium carbonate (0.140 g, 0.00101 mol) in anhydrous N,N-dimethylformamide (3 ml) is heated at 140° C. for 40 minutes under microwave irradiation. After cooling to room temperature the reaction mixture was quenched with 2M hydrochloric acid and extracted with ethyl acetate. The organic phase is separated, washed with distilled water then dried over anhydrous magnesium sulfate. The mixture is filtered, the filtrate is evaporated in vacuo and the residue is purified by preparative reverse phase HPLC to afford 2-[4-

(6-chloroquinolin-2-yloxy)-2,6-dimethylphenyl]-4-(tetrahydropyran-4-ylmethyl)cyclopentane-1,3-dione.

Example 6

Preparation of 2-[4-(4-chlorophenoxy)-2-ethylphenyl]cyclopentane-1,3-dione

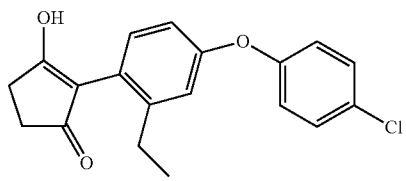 [SMILES: CCc1cc(Oc2ccc(Cl)cc2)ccc1C1=C(O)CCC1=O]

Step 1: Preparation of (4-bromo-2-ethylphenyl)furan-2-yl methanol

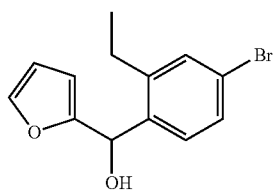 [SMILES: CCc1cc(Br)ccc1C(O)c1ccco1]

Magnesium turnings (1.16 g, 0.048 mol) are stirred under a nitrogen atmosphere for 30 minutes, followed by dropwise addition of 4-bromo-2-ethyl-1-iodobenzene (15.0 g, 0.048 mol) as a solution in anhydrous tetrahydrofuran (40 ml), until the magnesium is just covered. A crystal of iodine is added and the reaction heated to reflux. After initiation begins external heating is stopped and the remaining aryl halide solution is added at such a rate as to maintain a controlled reflux. Once addition is complete the reaction is heated at reflux for 1 hour and the mixture is then cooled to room temperature. A solution of furan-2-carbaldehyde (4.0 ml, 0.048 mol) in anhydrous tetrahydrofuran (10 ml) is then added dropwise, and the suspension is then stirred at room temperature for 20 hours. The reaction is quenched with saturated ammonium chloride (200 ml) and extracted with ethyl acetate (200 ml). The organic phase is separated, dried over anhydrous magnesium sulfate then evaporated under reduced pressure. The crude product is purified by flash column chromatography (1:4 ethyl acetate/hexane eluant) to afford (4-bromo-2-ethyl-phenyl)furan-2-yl methanol as a brown oil.

Step 2: Preparation of rac-5-(4-bromo-2-ethylphenyl)-4-hydroxycyclopent-2-enone

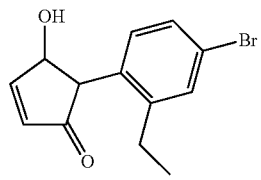 [SMILES: CCc1cc(Br)ccc1C1C(=O)C=CC1O]

To a solution of (4-bromo-2-ethylphenyl)furan-2-yl-methanol (13.6 g, 0.039 mol) in acetone (300 ml) and water (30 ml) at 55° C. is added polyphosphoric acid (5.0 g, 0.05 mol). After stirring at this temperature for 20 hours the reaction mixture is cooled to room temperature then concentrated in vacuo. The crude product is then partitioned between ethyl acetate (200 ml) and water (200 ml), and the organic phase is separated. After drying over anhydrous magnesium sulfate, all solvents are removed and the crude product is purified by flash column chromatography (1:1 ethyl acetate/hexane) to afford 5-(4-bromo-2-ethylphenyl)-4-hydroxycyclopent-2-enone as a brown gum.

Step 3: Preparation of 2-(4-bromo-2-ethylphenyl)cyclopent-4-ene-1,3-dione

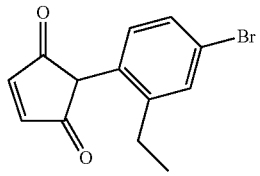 [SMILES: CCc1cc(Br)ccc1C1C(=O)C=CC1=O]

To a solution of 5-(4-bromo-2-ethylphenyl)-4-hydroxycyclopent-2-enone (10.14 g, 0.036 mol) in acetone (150 ml) at 5° C. is added chromium trioxide in concentrated sulfuric acid (24 ml, 0.039 mol, 1.64M solution), at such a rate as to maintain a temperature between 10° C. to 15° C. The reaction mixture is further stirred at room temperature for 30 minutes, followed by the addition of isopropanol (150 ml) and additional stirring at room temperature for 2 hours. The green suspension is partitioned between ethyl acetate (200 ml) and water (300 ml), and the organic layer is separated. After drying over anhydrous magnesium sulfate, solvents are removed in vacuo to afford 2-(4-bromo-2-ethylphenyl)cyclopent-4-ene-1,3-dione as an orange gum.

Step 4: Preparation of 2-(4-bromo-2-ethylphenyl)cyclopentane-1,3-dione

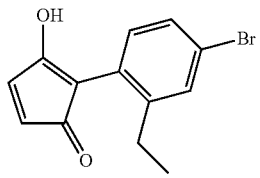 [SMILES: CCc1cc(Br)ccc1C1=C(O)C=CC1=O]

To a suspension of zinc dust (2.0 g, 0.03 mol) in glacial acetic acid (30 ml) is added a solution of 2-(4-bromo-2-ethylphenyl)cyclopent-4-ene-1,3-dione (1.20 g, 0.0043 mol) in glacial acetic acid (20 ml) dropwise over 10 minutes. After stirring of the resultant suspension for 20 hours at room temperature the reaction mixture is filtered through diatomaceous earth and the filtrate is evaporated under reduced pressure to afford 2-(4-bromo-2-ethylphenyl)cyclopentane-1,3-dione as a pink solid.

Step 5: Preparation of 2-[4-(4-chlorophenoxy)-2-ethylphenyl]-cyclopentane-1,3-dione

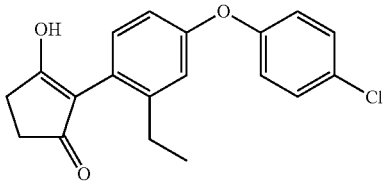 [SMILES: CCc1cc(Oc2ccc(Cl)cc2)ccc1C1=C(O)CCC1=O]

To a mixture of 2-(4-bromo-2-ethylphenyl)cyclopentane-1,3-dione (0.20 g, 0.0007 mol), 4-chlorophenol (0.180 g, 0.0014 mol), cesium carbonate (0.460 g, 0.0014 mol), copper triflate (10 mg, 0.00003 mol) and activated 4 Å molecular sieves (0.30 g) is added anhydrous toluene (7 ml). The mixture is then heated at 16° C. for 1 hour under microwave irradiation, followed by dilution with ethyl acetate (50 ml) and 2M hydrochloric acid (50 ml). The organic phase is separated, dried over anhydrous magnesium sulfate and concentrated under reduced pressure. The crude product is purified by preparative reverse phase HPLC to afford 2-[4-(4-chlorophenoxy)-2-ethylphenyl]-3-hydroxycyclopent-2-enone as a cream solid.

Additional compounds in Table T1 and Table P1 below were prepared by similar methods using appropriate starting materials.

| Compound Number | Structure | $^1$H NMR (CDCl$_3$ unless stated) or other physical data |
|---|---|---|
| A-1 | 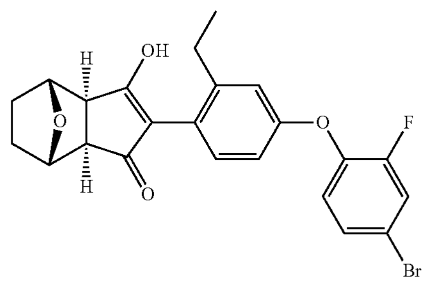 [SMILES: CCc1cc(Oc2ccc(Br)cc2F)ccc1C1=C(O)[C@H]2[C@@H](C1=O)[C@@H]1CC[C@H]2O1] | d$_4$-MeOH: δ 7.49 (m, 1H), 7.34 (m, 1H), 7.05 (d, 1H), 7.01 (d, 1H), 6.92 (dd, 1H), 6.80 (m, 1H), 4.62 (br. t, 2H), 2.86 (s, 2H), 2.47 (q, 2H), 1.88-1.79 (m, 2H), 1.65-1.71 (m, 2H), 1.08 (t, 3H) |
| A-2 | 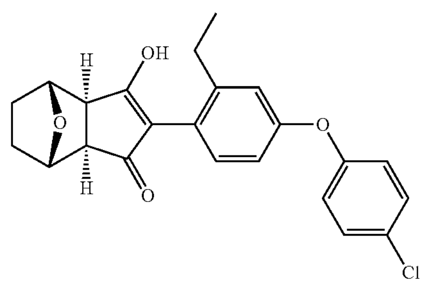 [SMILES: CCc1cc(Oc2ccc(Cl)cc2)ccc1C1=C(O)[C@H]2[C@@H](C1=O)[C@@H]1CC[C@H]2O1] | d$_4$-MeOH: δ 7.35 (m, 2H), 7.01 (m, 3H), 6.94 (m, 1H), 6.83 (dd, 1H), 4.62 (m, 2H), 2.86 (s, 2H), 2.47 (q, 2H), 1.89-1.79 (m, 2H), 1.68 (m, 2H), 1.08 (t, 3H) |
| A-3 | 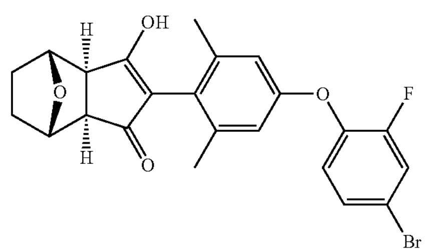 [SMILES: Cc1cc(Oc2ccc(Br)cc2F)cc(C)c1C1=C(O)[C@H]2[C@@H](C1=O)[C@@H]1CC[C@H]2O1] | d$_4$-MeOH: δ 7.45 (dd, 1H), 7.29 (m, 1H), 6.99 (t, 1H), 6.66 (s, 2H), 4.59 (t, 2H), 2.85 (s, 2H), 2.05 (s, 6H), 1.84-1.76 (m, 2H), 1.69-1.62 (m, 2H). |
| A-4 | 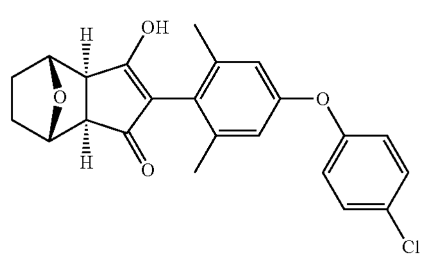 [SMILES: Cc1cc(Oc2ccc(Cl)cc2)cc(C)c1C1=C(O)[C@H]2[C@@H](C1=O)[C@@H]1CC[C@H]2O1] | d$_4$-MeOH: δ 7.33 (m, 2H), 6.99 (m, 2H), 6.72 (s, 2H), 4.62 (m, 2H), 2.89 (s, 2H), 2.08 (s, 6H), 1.89-1.80 (m, 2H), 1 69 (m, 2H). |

| Compound Number | Structure | ¹H NMR (CDCl₃ unless stated) or other physical data |
|---|---|---|
| A-5 | 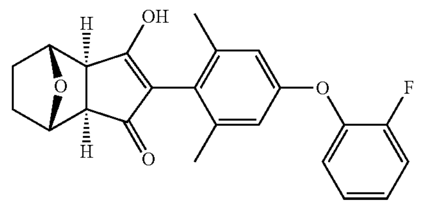 [SMILES: Cc1cc(Oc2ccccc2F)cc(C)c1C1=C(O)[C@H]2[C@@H](C1=O)[C@@H]1CC[C@H]2O1] | d₄-MeOH: δ 7.29-7.05 (m, 4H), 6.66 (s, 2H), 4.64-4.57 (m, 2H), 2.88 (s, 2H), 2.07 (s, 6H), 1.87-1.78 (m, 2H), 1.72-1.63 (m, 2H). |
| A-6 | 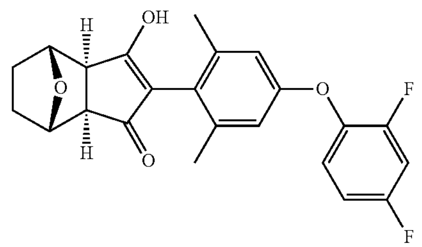 [SMILES: Cc1cc(Oc2ccc(F)cc2F)cc(C)c1C1=C(O)[C@H]2[C@@H](C1=O)[C@@H]1CC[C@H]2O1] | d₄-MeOH: δ 7.20-7.08 (m, 2H), 6.97 (m, 1H), 6.65 (s, 2H), 4.64-4.58 (m, 2H), 2.87 (s, 2H), 2.07 (s, 6H), 1.88-1.79 (m, 2H), 1.72-1.64 (m, 2H). |
| A-7 | 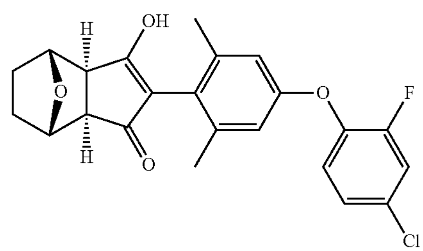 | d₄-MeOH: δ 7.35 (dd, 1H), 7.19 (m, 1H), 7.08 (t, 1H), 6.69 (s, 2H), 4.66-4.57 (m, 2H), 2.87 (s, 2H), 2.08 (s, 6H), 1.88-1.78 (m, 2H), 1.72-1.65 (m, 2H). |
| A-8 | 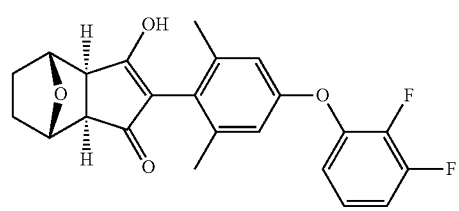 [SMILES: Cc1cc(Oc2cccc(F)c2F)cc(C)c1C1=C(O)[C@H]2[C@@H](C1=O)[C@@H]1CC[C@H]2O1] | d₄-MeOH: δ 7.16-7.01 (m, 2H), 6.88 (t, 1H), 6.72 (s, 2H), 4.64-4.59 (m, 2H), 2.88 (s, 2H), 2.09 (s, 6H), 1.88-1.79 (m, 2H), 1.73-1.65 (m, 2H). |
| A-9 | 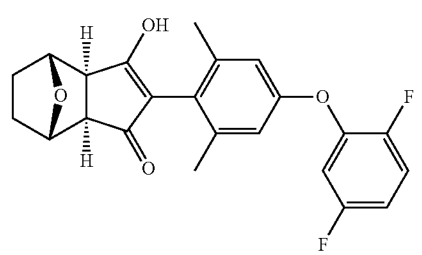 [SMILES: Cc1cc(Oc2cc(F)ccc2F)cc(C)c1C1=C(O)[C@H]2[C@@H](C1=O)[C@@H]1CC[C@H]2O1] | d₄-MeOH: δ 7.21 (m, 1H), 6.88-6.75 (m, 2H), 6.70 (s, 2H), 4.62-4.56 (m, 2H), 2.85 (s, 2H), 2.07 (s, 6H), 1.84-1.76 (m, 2H), 1.70-1.61 (m, 2H). |
| A-10 | 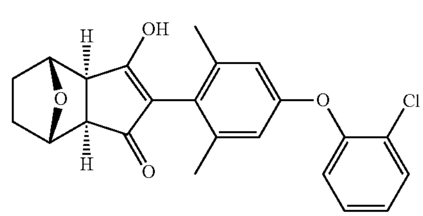 [SMILES: Cc1cc(Oc2ccccc2Cl)cc(C)c1C1=C(O)[C@H]2[C@@H](C1=O)[C@@H]1CC[C@H]2O1] | d₄-MeOH: δ 7.49 (dd, 1H), 7.28 (m, 1H), 7.13 (m, 1H), 7.03 (dd, 1H), 6.62 (s, 2H), 4.62-4.55 (m, 2H), 2.84 (s, 2H), 2.05 (s, 6H), 1.85-1.76 (m, 2H), 1.70-1.61 (m, 2H). |

| Compound Number | Structure | ¹H NMR (CDCl₃ unless stated) or other physical data |
|---|---|---|
| A-11 | 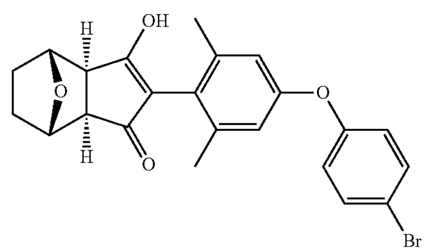 [SMILES: Cc1cc(Oc2ccc(Br)cc2)cc(C)c1C1=C(O)[C@H]2[C@@H](C1=O)[C@@H]1CC[C@H]2O1] | d₄-MeOH: δ 7.44 (m, 2H), 6.90 (m, 2H), 6.69 (s, 2H), 4.594 (m, 2H), 2.85 (s, 2H), 2.05 (s, 6H), 1.84-1.77 (m, 2H), 1.66 (m, 2H). |
| A-12 | 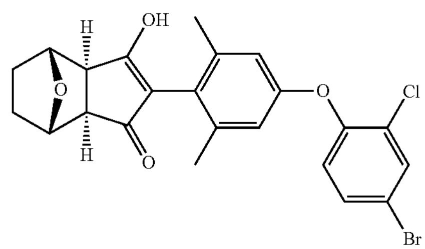 | d₄-MeOH: δ 7.66 (d, 1H), 7.40 (dd, 1H), 6.91 (d, 1H), 6.65 (s, 2H), 4.59 (m, 2H), 2.85 (s, 2H), 2.05 (s, 6H), 1.84-1.76 (m, 2H), 1.69-1.62 (m, 2H). |
| A-13 | 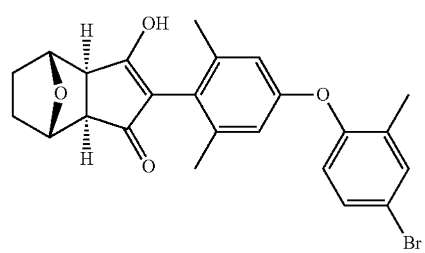 | d₄-MeOH + 2 drops d₆-DMSO: δ 7.46 (d, 1H), 7.33 (dd, 1H), 6.82 (d, 1H), 6.62 (s, 2H), 4.62 (m, 2H), 2.88 (s, 2H), 2.25 (s, 3H), 2.07 (s, 6H), 1.87-1.79 (m, 2H), 1.73-1.65 (m, 2H). |
| A-14 | 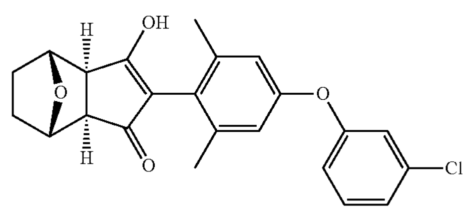 [SMILES: Cc1cc(Oc2cccc(Cl)c2)cc(C)c1C1=C(O)[C@H]2[C@@H](C1=O)[C@@H]1CC[C@H]2O1] | d₄-MeOH: δ 7.28 (t, 1H), 7.06 (m, 1H), 6.96 (t,1H), 6.91 (dd, 1H), 6.72 (s, 2H), 4.60 (t, 2H), 2.86 (s, 2H), 2.07 (s, 6H), 1.85-1.77 (m, 2H), 1.70-1.62 (m, 2H). |
| A-15 | 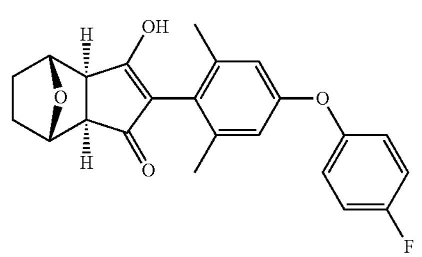 | d₄-MeOH: δ 7.13-6.96 (m, 4H), 6.68 (s, 2H), 4.62 (m, 2H), 2.88 (s, 2H), 2.07 (s, 6H), 1.88-1.77 (m, 2H), 1.72-1.63 (m, 2H). |
| A-16 | 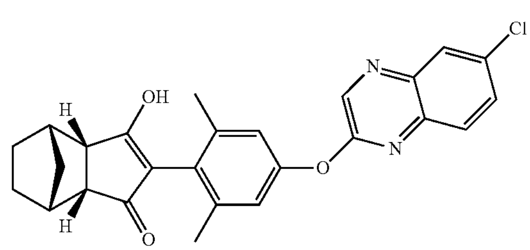 [SMILES: Cc1cc(Oc2cnc3cc(Cl)ccc3n2)cc(C)c1C1=C(O)[C@H]2[C@H]3CC[C@H](C3)[C@H]2C1=O] | δ 8.30 (s, 1H), 8.02 (d, 1H), 7.68 (d, 1H), 7.68 (dd, 1H), 6.92 (s, 2H), 3.27 (m, 1H), 3.01 (m, 1H), 2.73 (m, 2H), 2.22 (s, 3H), 2.11 (s, 3H), 1.80-1.49 (m, 6H). |

| Compound Number | Structure | ¹H NMR (CDCl₃ unless stated) or other physical data |
|---|---|---|
| A-17 | 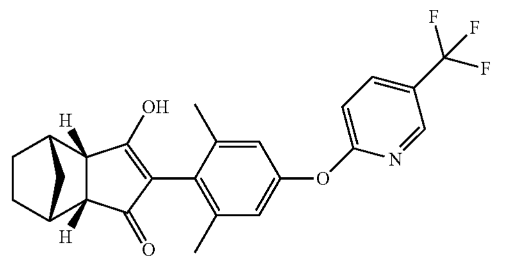 [SMILES: Cc1cc(Oc2ccc(C(F)(F)F)cn2)cc(C)c1C1=C(O)[C@H]2[C@H]3CC[C@H](C3)[C@H]2C1=O] | δ 8.47 (s, 1H), 8.34 (dd, 1H), 7.45 (d, 1H), 6.88 (s, 2H), 3.30 (m, 2H), 2.76 (m, 2H), 2.23 (s, 3H), 2.10 (s, 3H), 1.83 (d, 1H), 1.75 (d 1H), 1.64 (d, 2H), 1.43 (d 2H). |
| A-18 | 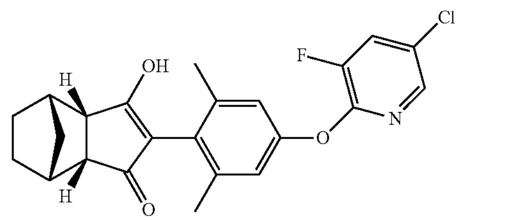 [SMILES: Cc1cc(Oc2ncc(Cl)cc2F)cc(C)c1C1=C(O)[C@H]2[C@H]3CC[C@H](C3)[C@H]2C1=O] | δ 7.86 (s, 1H), 7.71 (d, 1H), 6.84 (s, 2H), 3.28 (m, 2H), 2.74 (m, 2H), 2.20 (s, 3H), 2.07 (s, 3H), 1.81 (d, 1H), 1.75 (d 1H), 1.63 (d, 2H), 1.41 (d 2H). |
| A-19 | 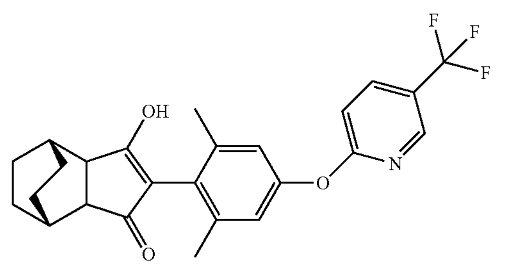 [SMILES: Cc1cc(Oc2ccc(C(F)(F)F)cn2)cc(C)c1C1=C(O)C2C(C1=O)[C@H]1CC[C@@H]2CC1] | δ 8.37 (s, 1H), 7.91 (dd, 1H), 7.08 (d, 1H), 6.87 (s, 2H), 3.00 (m, 1H), 2.69 (m, 1H), 2.23 (s, 3H), 2.14 (s, 3H), 2.14 (m, 1H), 1.83-1.40 (m, 9H). |
| A-20 | 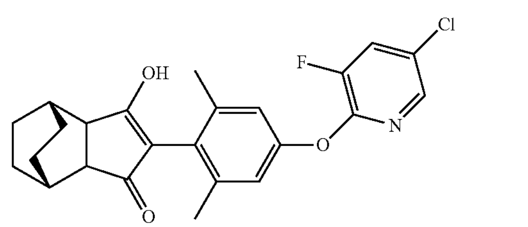 [SMILES: Cc1cc(Oc2ncc(Cl)cc2F)cc(C)c1C1=C(O)C2C(C1=O)[C@H]1CC[C@@H]2CC1] | δ 7.82 (s, 1H), 7.52 (d, 1H), 6.86 (s, 2H), 3.38 (s, 1H), , 2.77 (m, 2H), 2.19 (s, 3H), 2.15 (m, 2H), 2.11 (s, 3H), 1.81-1.55 (m, 6H), 1.45 (m 2H). |
| A-21 | 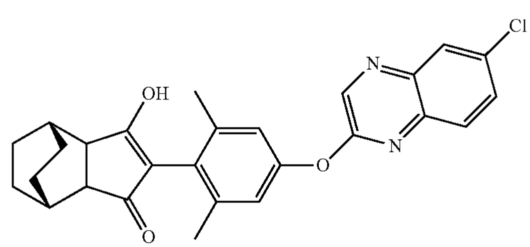 [SMILES: Cc1cc(Oc2cnc3cc(Cl)ccc3n2)cc(C)c1C1=C(O)C2C(C1=O)[C@H]1CC[C@@H]2CC1] | δ 8.67 (s, 1H), 8.04 (d, 1H), 7.75 (d, 1H), 7.62 (dd, 1H), 6.96 (s, 2H), 2.94 (m, 1H), 2.62 (m, 1H), 2.26 (s, 3H), 2.20 (m, 2H), 2.18 (s, 3H), 1.80-1.6 (m, 6H), 1.45 (m, 2H). |
| A-22 | 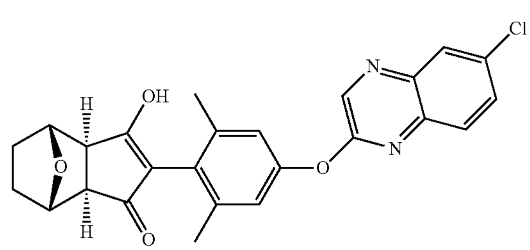 [SMILES: Cc1cc(Oc2cnc3cc(Cl)ccc3n2)cc(C)c1C1=C(O)[C@H]2[C@@H](C1=O)[C@@H]1CC[C@H]2O1] | δ 8.26 (s, 1H), 8.01 (d, 1H), 7.70-7.58 (m, 2H), 6.93 (s, 1H), 6.88 (s, 1H), 4.77 (m, 2H), 3.01 (m, 1H), 2.75 (m, 1H), 2.15 (s, 3H), 2.11 (s, 3H), 2.00-1.50 (m, 4H). |

| Compound Number | Structure | ¹H NMR (CDCl₃ unless stated) or other physical data |
|---|---|---|
| A-23 | 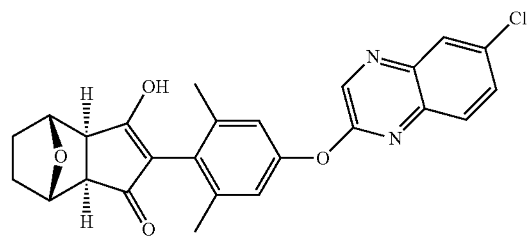 [SMILES: Cc1cc(Oc2cnc3cc(Cl)ccc3n2)cc(C)c1C1=C(O)[C@H]2[C@@H](C1=O)[C@@H]1CC[C@H]2O1] | δ 8.31 (s, 1H), 7.91 (dd, 1H), 7.06 (d, 1H), 6.83 (s, 2H), 4.69 (m, 2H), 2.82 (m, 2H), 2.14 (s, 3H), 2.13 (s, 3H), 1.85 (m, 2H), 1.60 (m, 2H). |
| A-24 | 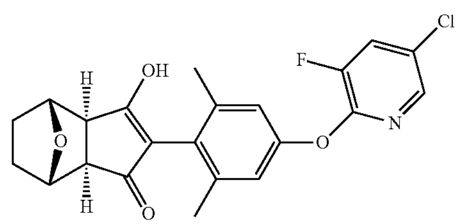 | δ 7.76 (s, 1H), 7.51 (d, 1H), 6.81 (s, 2H), 4.63 (m, 2H), 2.76 (m, 2H), , 2.11 (s, 3H), 2.09 (s, 3H), 1.81 (m, 2H), 1.55 (m, 2H). |
| A-25 | 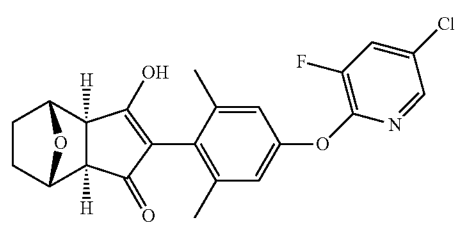 [SMILES: Cc1cc(Oc2ncc(Cl)cc2F)cc(C)c1C1=C(O)[C@H]2[C@@H](C1=O)[C@@H]1CC[C@H]2O1] | δ 7.93 (d, 1H), 7.62 (s, 1H), 7.56 (d, 1H), 7.40 (dd, 1H), 6.95 (d, 1H), 6.73 (s, 2H), 4.5 (m, 2H), 2.63 (m, 2H), 1.98 (s, 3H), 1.97 (s, 3H), 1.66 (m, 2H), 1.43 (m, 2H). |
| A-26 | 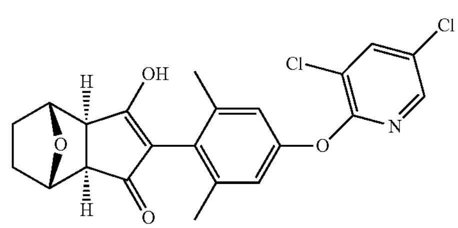 [SMILES: Cc1cc(Oc2ncc(Cl)cc2Cl)cc(C)c1C1=C(O)[C@H]2[C@@H](C1=O)[C@@H]1CC[C@H]2O1] | δ 7.81 (s, 1H), 7.65 (s, 1H), 6.86 (s, 2H), 4.52 (m, 2H), 2.64 (m, 2H), , 1.98 (s, 3H), 1.97 (s, 3H), 1.69 (m, 2H), 1.45 (m, 2H). |
| A-27 | 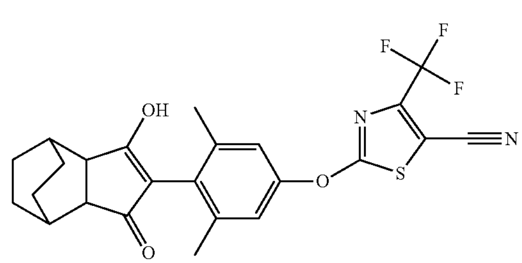 [SMILES: Cc1cc(Oc2nc(C(F)(F)F)c(C#N)s2)cc(C)c1C1=C(O)C2C3CCC(CC3)C2C1=O] | δ 6.90 (s, 2H), 2.50 (m, 2H), 2.17 (s, 3H), 2.09 (s, 5H), 1.56 (m, 6H), 1.34 (m, 2H). |
| A-28 | 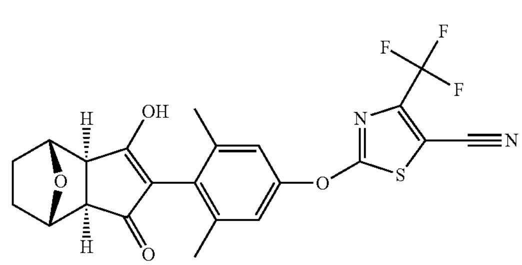 [SMILES: Cc1cc(Oc2nc(C(F)(F)F)c(C#N)s2)cc(C)c1C1=C(O)[C@H]2[C@@H](C1=O)[C@@H]1CC[C@H]2O1] | δ 6.97 (s, 2H), 4.70 (m, 2H), 2.62 (s, 2H), 2.19 (s, 3H), 2.17 (s, 3H), 1.85 (m, 2H), 1.60 (m, 2H). |

-continued

| Compound Number | Structure | ¹H NMR (CDCl₃ unless stated) or other physical data |
|---|---|---|
| A-29 | 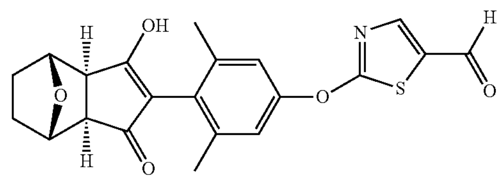 [SMILES: Cc1cc(Oc2ncc(C=O)s2)cc(C)c1C1=C(O)[C@H]2[C@@H](C1=O)[C@@H]1CC[C@H]2O1] | δ 9.83 (s,1H), 7.98 (s,1H), 6.98 (s, 2H), 4.77 (s, 2H), 2.99 (s, 2H), 2.14 (s, 6H), 1.91 (m, 2H), 1.65 (m, 2H). |
| A-30 | 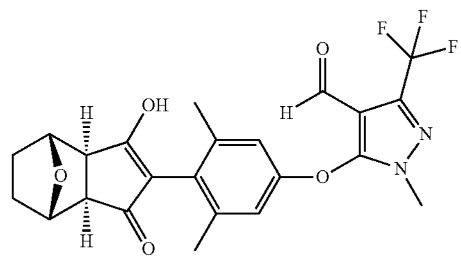 [SMILES: Cc1cc(Oc2c(C=O)c(C(F)(F)F)nn2C)cc(C)c1C1=C(O)[C@H]2[C@@H](C1=O)[C@@H]1CC[C@H]2O1] | δ 9.69 (s,1H), 6.63 (s, 2H), 4.68 (m, 2H), 3.77 (s, 3H), 2.78 (s, 2H), 2.13 (s, 3H), 2.11 (s, 3H), 1.84 (m, 2H), 1.58 (m, 2H). |
| A-31 | 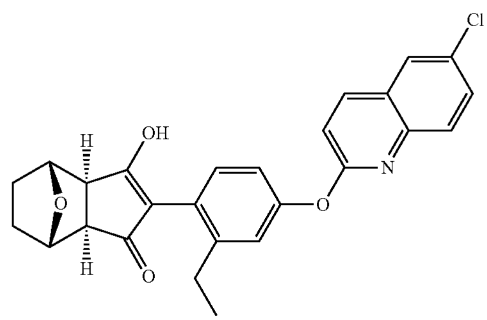 [SMILES: CCc1cc(Oc2ccc3cc(Cl)ccc3n2)ccc1C1=C(O)[C@H]2[C@@H](C1=O)[C@@H]1CC[C@H]2O1] | δ 8.05 (d, 1H), 7.75 (m, 1H), 7.64 (d, 1H), 7.52 (m, 1H), 7.20-7.00 (m, 4H), 4.72 (m, 2H), 2.88 (m, 2H), 2.52 (m, 2H), 1.87 (m, 2H), 1.60 (m, 2H), 1.13 (t, 3H). |
| A-32 | 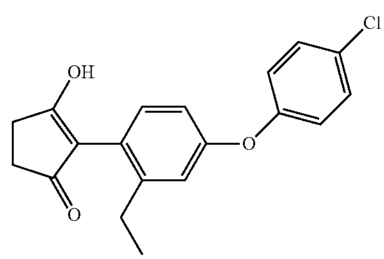 [SMILES: CCc1cc(Oc2ccc(Cl)cc2)ccc1C1=C(O)CCC1=O] | δ 7.29 (m, 2H), 7.04 (d, 1H), 6.96 (m, 2H), 6.92 (m, 1H), 6.80 (m, 1H), 2.67 (s, 4H), 2.48 (q, 2H), 1.10 (t, 3H) |
| A-33 | 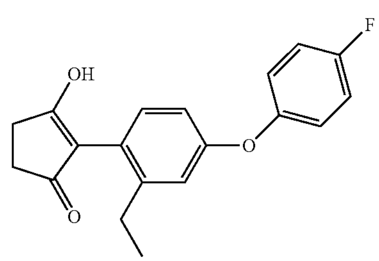 [SMILES: CCc1cc(Oc2ccc(F)cc2)ccc1C1=C(O)CCC1=O] | δ 7.10-6.95 (m, 5H), 6.90 (m, 1H), 6.77 (m, 1H), 2.66 (s, 4H), 2.48 (q, 2H), 1.10 (t, 3H) |
| A-34 | 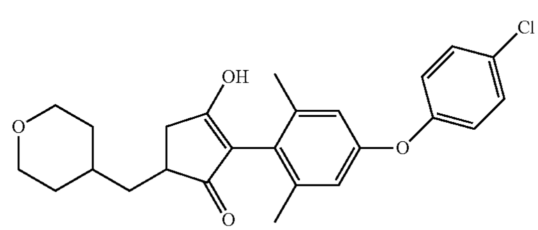 [SMILES: Cc1cc(Oc2ccc(Cl)cc2)cc(C)c1C1=C(O)CC(CC2CCOCC2)C1=O] | δ 7.28 (m, 2H), 6.96 (m, 2H), 6.68 (s, 2H), 3.98 (m, 2H), 3.42 (m, 2H), 2.83 (m, 2H), 2.38 (d,1H), 2.09 (s, 3H), 2.08 (s, 3H), 1.93 m, 1H), 1.80-1.60 (m, 3H), 1.50-1.25 (m, 3H). |

-continued
| Compound Number | Structure | ¹H NMR (CDCl₃ unless stated) or other physical data |
|---|---|---|
| A35 | 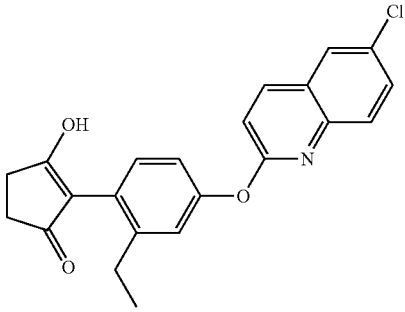 [SMILES: CCc1cc(Oc2ccc3cc(Cl)ccc3n2)ccc1C1=C(O)CCC1=O] | δ 8.12 (d, 1H), 7.78 (m, 1H), 7.73 (d, 1H), 7.58 (m, 1H), 7.19 (d, 1H), 7.13 (m, 2H), 7.04 (m, 1H), 2.71 (s, 4H), 2.52 (q, 2H), 1.13 (t, 3H) |
| A-36 | 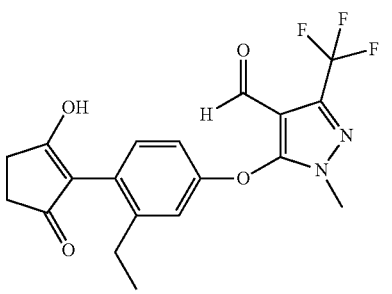 [SMILES: CCc1cc(Oc2c(C=O)c(C(F)(F)F)nn2C)ccc1C1=C(O)CCC1=O] | δ 9.67 (s, 1H), 7.04 (d, 1H), 6.95 (m, 1H), 6.75 (m, 1H), 3.84 (s, 3H), 2.70 (s, 4H), 2.49 (q, 2H), 1.11 (t, 3H) |
| A-37 | 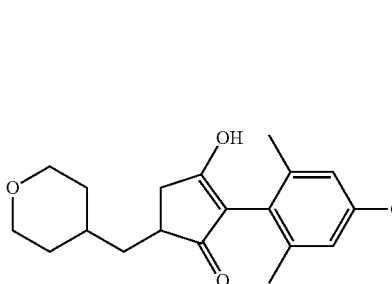 | δ 8.68 (d, 1H), 8.10 (d, 1H), 8.04 (m, 1H), 7.93 (m, 1H), 7.54 (d, 1H), 6.95 (s, 2H), 4.20 (m, 2H), 3.60 (m, 2H), 3.06 (m, 2H), 2.55 (m,1H), 2.15 (s, 3H), 2.14 (s, 3H), 2.00 (m, 1H) 1.78 (m, 3H), 1.48 (m, 3H). |
| A-38 | 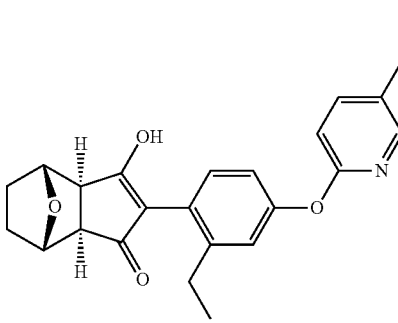 | δ 8.05 (d, 1H), 7.75 (m, 1H), 7.64 (d, 1H), 7.52 (m, 1H), 7.20-7.00 (m, 4H), 4.72 (m, 2H), 2.88 (m, 2H), 2.52 (m, 2H), 1.87 (m, 2H), 1.60 (m, 2H), 1.13 (t, 3H). |
| A-39 | 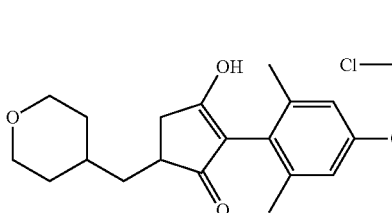 | δ 7.90 (m, 1H), 7.78 (m, 1H), 6.96 (m, 1H), 6.84 (s, 2H), 3.95 (m, 2H), 3.39 (m, 2H), 2.83 (m, 2H), 2.32 (m,1H), 2.11 (s, 3H), 2.10 (s, 3H), 1.90 (m, 1H) 1.64 (m, 3H), 1.34 (m, 3H). |

| Compound Number | Structure | ¹H NMR (CDCl₃ unless stated) or other physical data |
|---|---|---|
| P-1 | 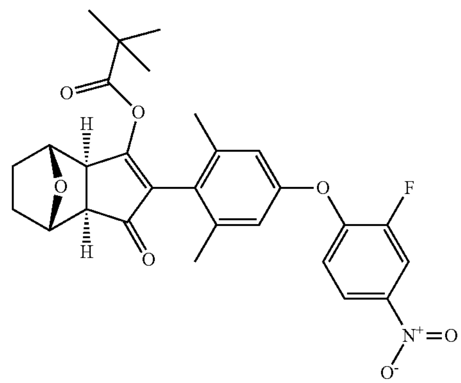 [SMILES: Cc1cc(Oc2ccc([N+](=O)[O-])cc2F)cc(C)c1C1=C(OC(=O)C(C)(C)C)[C@H]2[C@@H](C1=O)[C@@H]1CC[C@H]2O1] | δ 7.82-7.74 (m, 2H) 7.08 (m, 1H), 6.48 (m, 2H), 4.79 (d, 2H), 3.20 (d, 1H), 2.82 (d, 1H), 2.08 (s, 3H), 2.04 (s, 3H), 1.99-1.82 (m, 2H), 1.68-1.55 (m, 2H), 1.27 (s, 9H). |
| P-2 | 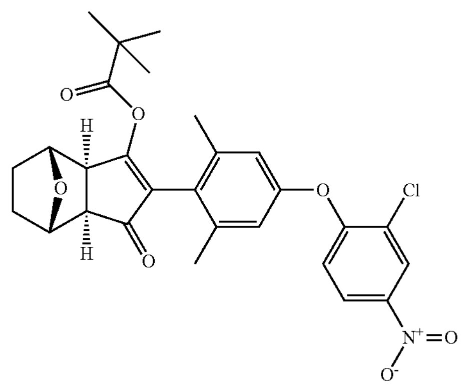 [SMILES: Cc1cc(Oc2ccc([N+](=O)[O-])cc2Cl)cc(C)c1C1=C(OC(=O)C(C)(C)C)[C@H]2[C@@H](C1=O)[C@@H]1CC[C@H]2O1] | δ 8.16 (d, 1H), 7.82 (dd, 1H), 6.96 (d, 1H), 6.52 (dd, 2H), 4.79 (t, 2H), 3.22 (d, 1H), 2.83 (d, 1H), 2.13 (s, 3H), 2.06 (s, 3H), 1.99-1.81 (m, 2H), 1.67-1.59 (m, 2H), 1.28 (s, 9H). |
| P-3 | 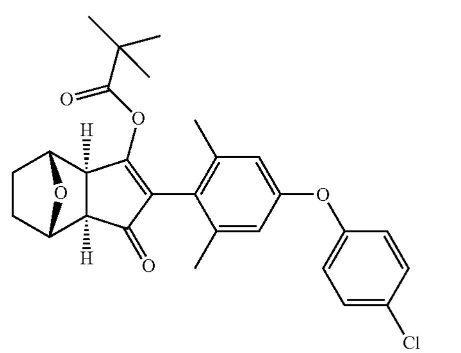 [SMILES: Cc1cc(Oc2ccc(Cl)cc2)cc(C)c1C1=C(OC(=O)C(C)(C)C)[C@H]2[C@@H](C1=O)[C@@H]1CC[C@H]2O1] | δ 7.27 (d, 2H), 6.91 (d, 2H), 6.67 (d, 2H), 4.76 (d, 1H), 4.56 (d, 1H), 3.45 (d, 1H), 2.80 (d, 1H), 2.11 (s, 3H), 2.04 (s, 3H), 1.96-1.79 (m, 2H), 1.69-1.54 (m, 2H), 1.13 (s, 9H). |
| P-4 | 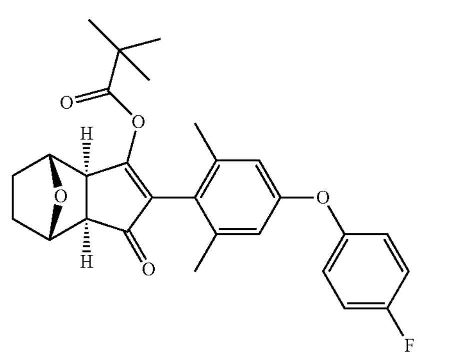 [SMILES: Cc1cc(Oc2ccc(F)cc2)cc(C)c1C1=C(OC(=O)C(C)(C)C)[C@H]2[C@@H](C1=O)[C@@H]1CC[C@H]2O1] | δ 7.04-6.91 (m, 4H), 6.63 (d, 2H), 4.75 (d, 1H), 4.56 (d, 1H), 3.45 (d, 1H), 2.80 (d, 1H), 2.10 (s, 3H), 2.03 (s, 3H), 1.95-1.78 (m, 2H), 1.68-1.53 (m, 2H), 1.13 (s, 9H). |

-continued

| Compound Number | Structure | ¹H NMR (CDCl₃ unless stated) or other physical data |
|---|---|---|
| P-5 | 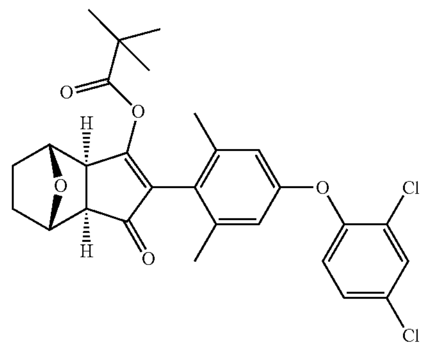 [SMILES: Cc1cc(Oc2ccc(Cl)cc2Cl)cc(C)c1C1=C(OC(=O)C(C)(C)C)[C@H]2[C@@H](C1=O)[C@@H]1CC[C@H]2O1] | δ 7.33 (d, 1H), 7.05 (dd, 1H), 6.88 (d, 1H), 6.64 (m, 2H), 4.77 (m, 1H), 4.65 (m, 1H), 3.08 (d, 1H), 2.77 (d, 1H), 2.15 (s, 3H), 2.08 (s, 3H), 1.89-1.76 (m, 2H), 1.64-1.53 (m, 2H), 1.32 (s, 9H). |
| P-6 | 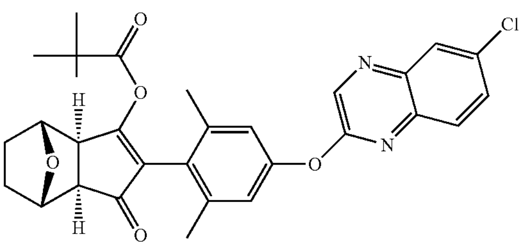 [SMILES: Cc1cc(Oc2cnc3cc(Cl)ccc3n2)cc(C)c1C1=C(OC(=O)C(C)(C)C)[C@H]2[C@@H](C1=O)[C@@H]1CC[C@H]2O1] | δ 8.56 (s, 1H), 8.04 (d, 1H), 7.75 (d, 1H), 7.72 (dd, 1H), 6.59 (d, 1H), 6.52 (d, 1H) 4.80 (d, 1H), 4.69 (d, 1H) 3.69 (d, 1H), 2.89 (d 1H), 2.18 (s, 3H), 2.09 (s, 3H), 1.88 (m, 2H), 1.64 (m, 2H), 1.28 (s, 9H). |
| P-7 | 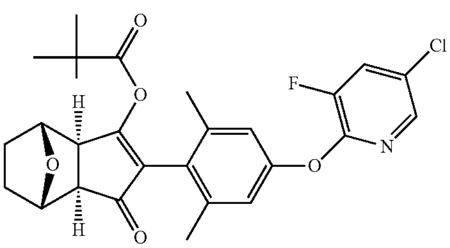 [SMILES: Cc1cc(Oc2ncc(Cl)cc2F)cc(C)c1C1=C(OC(=O)C(C)(C)C)[C@H]2[C@@H](C1=O)[C@@H]1CC[C@H]2O1] | δ 7.80 (s, 1H), 7.35 (d, 1H), 6.57 (d, 1H), 6.54 (d, 1H) 4.76 (d, 1H), 4.73 (d, 1H) 3.34 (d, 1H), 2.82 (d 1H), 2.11 (s, 3H), 2.06 (s, 3H), 1.86 (m, 2H), 1.60 (m, 2H), 1.31 (s, 9H). |

It should be noted that certain compounds of the invention exist as a mixture in any ratio of isomers, including atropisomers, noted above, under the conditions used to obtain the ¹H NMR data. Where this has occurred, the characterising data are reported for all isomers present at ambient temperature in the specified solvent. Unless otherwise stated, proton NMR spectra were recorded at ambient temperature.

The compounds of the following Tables 1 to 39 can be obtained in an analogous manner.

Table 1 covers compounds of the following type

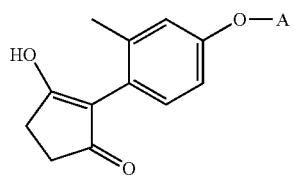

wherein A is as defined in Table 1.

TABLE 1

| Compound Number | A | Compound Number | A |
|---|---|---|---|
| 1.001 | phenyl | 1.002 | 2-bromophenyl |
| 1.003 | 2-chlorophenyl | 1.004 | 2-cyanophenyl |
| 1.005 | 2-difluoromethoxyphenyl | 1.006 | 2-fluorophenyl |
| 1.007 | 2-methoxyphenyl | 1.008 | 2-methylphenyl |
| 1.009 | 2-nitrophenyl | 1.010 | 2-trifluoromethoxyphenyl |
| 1.011 | 2-trifluoromethylphenyl | 1.012 | 3-bromophenyl |
| 1.013 | 3-chlorophenyl | 1.014 | 3-cyanophenyl |
| 1.015 | 3-difluoromethoxyphenyl | 1.016 | 3-fluorophenyl |
| 1.017 | 3-methoxyphenyl | 1.018 | 3-methylphenyl |
| 1.019 | 3-nitrophenyl | 1.020 | 3-trifluoromethoxyphenyl |
| 1.021 | 3-trifluoromethylphenyl | 1.022 | 4-bromophenyl |
| 1.023 | 4-chlorophenyl | 1.024 | 4-cyanophenyl |

TABLE 1-continued

| Compound Number | A | Compound Number | A |
|---|---|---|---|
| 1.025 | 4-difluoromethoxyphenyl | 1.026 | 4-fluorophenyl |
| 1.027 | 4-methanesulfonyl | 1.028 | 4-methoxyphenyl |
| 1.029 | 4-methylphenyl | 1.030 | 4-nitrophenyl |
| 1.031 | 4-trifluoromethoxyphenyl | 1.032 | 4-trifluoromethylphenyl |
| 1.033 | 4-bromo-2-chlorophenyl | 1.034 | 2,4-dichlorophenyl |
| 1.035 | 2-chloro-4-cyanophenyl | 1.036 | 2-chloro-4-difluoromethoxyphenyl |
| 1.037 | 2-chloro-4-fluorophenyl | 1.038 | 2-chloro-4-methoxyphenyl |
| 1.039 | 2-chloro-4-methylphenyl | 1.040 | 2-chloro-4-nitrophenyl |
| 1.041 | 2-chloro-4-trifluoromethoxyphenyl | 1.042 | 2-chloro-4-trifluoromethylphenyl |
| 1.043 | 4-bromo-3-chlorophenyl | 1.044 | 3,4-dichlorophenyl |
| 1.045 | 3-chloro-4-cyanophenyl | 1.046 | 3-chloro-4-difluoromethoxyphenyl |
| 1.047 | 3-chloro-4-fluorophenyl | 1.048 | 3-chloro-4-methoxyphenyl |
| 1.049 | 3-chloro-4-methylphenyl | 1.050 | 3-chloro-4-nitrophenyl |
| 1.051 | 3-chloro-4-trifluoromethoxyphenyl | 1.052 | 3-chloro-4-trifluoromethylphenyl |
| 1.053 | 2-bromo-4-chlorophenyl | 1.054 | 4-chloro-2-difluoromethoxyphenyl |
| 1.055 | 4-chloro-2-cyanophenyl | 1.056 | 4-chloro-2-methoxyphenyl |
| 1.057 | 4-chloro-2-fluorophenyl | 1.058 | 4-chloro-2-nitrophenyl |
| 1.059 | 4-chloro-2-methylphenyl | 1.060 | 4-chloro-2-trifluoromethylphenyl |
| 1.061 | 4-chloro-2-trifluoromethoxyphenyl | 1.062 | 4-chloro-3-trifluoromethoxyphenyl |
| 1.063 | 3-bromo-4-chlorophenyl | 1.064 | 4-chloro-3-difluoromethoxyphenyl |
| 1.065 | 4-chloro-3-cyanophenyl | 1.066 | 4-chloro-3-methoxyphenyl |
| 1.067 | 4-chloro-3-fluorophenyl | 1.068 | 4-chloro-3-nitrophenyl |
| 1.069 | 4-chloro-3-methylphenyl | 1.070 | 4-chloro-3-trifluoromethylphenyl |
| 1.071 | 4-bromo-2-fluorophenyl | 1.072 | 2-difluoro-4-difluoromethoxyphenyl |
| 1.073 | 4-cyano-2-fluorophenyl | 1.074 | 2-fluoro-4-methoxyphenyl |
| 1.075 | 2,4-fluorophenyl | 1.076 | 2-fluoro-4-nitrophenyl |
| 1.077 | 2-fluoro-4-methylphenyl | 1.078 | 2-fluoro-4-trifluoromethylphenyl |
| 1.079 | 2-fluoro-4-trifluoromethoxyphenyl | 1.080 | 4-bromo-3-fluorophenyl |
| 1.081 | 4-cyano-3-fluorophenyl | 1.082 | 3-difluoro-4-difluoromethoxyphenyl |
| 1.083 | 3,4-fluorophenyl | 1.084 | 3-fluoro-4-methoxyphenyl |
| 1.085 | 3-fluoro-4-methylphenyl | 1.086 | 3-fluoro-4-nitrophenyl |
| 1.087 | 3-fluoro-4-trifluoromethoxyphenyl | 1.088 | 3-fluoro-4-trifluoromethylphenyl |
| 1.089 | 4-chloro-2,3-difluorophenyl | 1.090 | 4-chloro-2,5-difluorophenyl |
| 1.091 | 4-chloro-2,6-difluorophenyl | 1.092 | 4-chloro-3,5-difluorophenyl |
| 1.093 | 2,4-dichloro-3-fluorophenyl | 1.094 | 2,4-dichloro-5-fluorophenyl |
| 1.095 | 2,4-dichloro-6-fluorophenyl | 1.096 | 2,3,4-trifluorophenyl |
| 1.097 | 2,4,6-trifluorophenyl | 1.098 | 2,4,5-trifluorophenyl |
| 1.099 | 3,4,5-trifluorophenyl | 1.100 | pentafluorophenyl |
| 1.101 | 2-bromo-4-cyanophenyl | 1.102 | 3-bromo-4-cyanophenyl |
| 1.103 | 4-bromo-2-cyanophenyl | 1.104 | 4-bromo-3-cyanophenyl |
| 1.105 | 2-cyano-4-nitrophenyl | 1.106 | 3-cyano-4-nitrophenyl |
| 1.107 | 2-cyano-4-trifluoromethylphenyl | 1.108 | 3-cyano-4-trifluoromethylphenyl |
| 1.109 | 2,4-dicyanophenyl | 1.110 | 3,4-dicyanophenyl |
| 1.111 | 3-chloropyridin-2-yl | 1.112 | 4-chloropyridin-2-yl |
| 1.113 | 5-chloropyridin-2-yl | 1.114 | 6-chloropyridin-2-yl |
| 1.115 | 2-chloropyridin-3-yl | 1.116 | 4-chloropyridin-3-yl |
| 1.117 | 5-chloropyridin-3-yl | 1.118 | 6-chloropyridin-3-yl |
| 1.119 | 2-chloropyridin-4-yl | 1.120 | 3-chloropyridin-4-yl |
| 1.121 | 3,4-dichloropyridin-2-yl | 1.122 | 3,5-dichloropyridin-2-yl |
| 1.123 | 3,6-dichloropyridin-2-yl | 1.124 | 2,5-dichloropyridin-3-yl |
| 1.125 | 2,6-dichloropyridin-3-yl | 1.126 | 2,3-dichloropyridin-4-yl |
| 1.127 | 2,5-dichloropyridin-4-yl | 1.128 | 3,5,6-trichloropyridin-2-yl |
| 1.129 | 3-fluoropyridin-2-yl | 1.130 | 4-fluoropyridin-2-yl |
| 1.131 | 5-fluoropyridin-2-yl | 1.132 | 6-fluoropyridin-2-yl |
| 1.133 | 2-fluoropyridin-3-yl | 1.134 | 4-fluoropyridin-3-yl |
| 1.135 | 5-fluoropyridin-3-yl | 1.136 | 6-fluoropyridin-3-yl |
| 1.137 | 2-fluoropyridin-4-yl | 1.138 | 3-fluoropyridin-4-yl |
| 1.139 | 3,4-difluoropyridin-2-yl | 1.140 | 3,5-difluoropyridin-2-yl |
| 1.141 | 3,6-difluoropyridin-2-yl | 1.142 | 2,5-difluoropyridin-3-yl |
| 1.143 | 2,6-difluoropyridin-3-yl | 1.144 | 2,3-difluoropyridin-4-yl |
| 1.145 | 2,5-difluoropyridin-4-yl | 1.146 | 3,5,6-trifluoropyridin-2-yl |
| 1.147 | 3-trifluoromethylpyridin-2-yl | 1.148 | 4-trifluoromethylpyridin-2-yl |
| 1.149 | 5-trifluoromethylpyridin-2-yl | 1.150 | 6-trifluoromethylpyridin-2-yl |
| 1.151 | 2-trifluoromethylpyridin-3-yl | 1.152 | 4-trifluoromethylpyridin-3-yl |
| 1.153 | 5-trifluoromethylpyridin-3-yl | 1.154 | 6-trifluoromethylpyridin-3-yl |
| 1.155 | 2-trifluoromethylpyridin-4-yl | 1.156 | 3-trifluoromethylpyridin-4-yl |
| 1.157 | 4-chloro-3-fluoropyridin-2-yl | 1.158 | 5-chloro-3-fluoropyridin-2-yl |
| 1.159 | 6-chloro-3-fluoropyridin-2-yl | 1.160 | 3-chloro-4-fluoropyridin-2-yl |
| 1.161 | 3-chloro-5-fluoropyridin-2-yl | 1.162 | 3-chloro-6-fluoropyridin-2-yl |
| 1.163 | 3-chloro-5-trifluoromethylpyridin-2-yl | 1.164 | 3-fluoro-5-trifluoromethylpyridin-2-yl |
| 1.165 | 6-fluoro-3,4,5-trichloropyridin-2-yl | 1.166 | 4-methyl-3,5,6-trifluoropyridin-2-yl |
| 1.167 | pyrimidin-2-yl | 1.168 | 5-fluoropyrimidin-2-yl |
| 1.169 | 5-chloropyrimidin-2-yl | 1.170 | 5-bromopyrimidin-2-yl |
| 1.171 | 6-chloropyridazin-3-yl | 1.172 | 6-bromopyridazin-3-yl |
| 1.173 | quinoline-2-yl | 1.174 | 6-fluoroquinolin-2-yl |
| 1.175 | 7-fluoroquinolin-2-yl | 1.176 | 6-chloroquinolin-2-yl |
| 1.177 | 7-chloroquinolin-2-yl | 1.178 | 6-bromoquinolin-2-yl |

TABLE 1-continued

| Compound Number | A | Compound Number | A |
|---|---|---|---|
| 1.179 | 7-bromoquinolin-2-yl | 1.180 | 6-trifluoromethylquinolin-2-yl |
| 1.181 | 7-trifluoromethylquinolin-2-yl | 1.182 | quinoxalin-2-yl |
| 1.183 | 6-fluoroquinoxazin-2-yl | 1.184 | 7-fluoroquinoxalin-2-yl |
| 1.185 | 6-chloroquinoxalin-2-yl | 1.186 | 7-chloroquinoxalin-2-yl |
| 1.187 | 6-bromoquinoxalin-2-yl | 1.188 | 7-bromoquinoxalin-2-yl |
| 1.189 | 6-trifluoromethylquinoxalin-2-yl | 1.190 | 7-trifluoromethylquinoxalin-2-yl |
| 1.191 | quinazolin-2-yl | 1.192 | 6-fluoroquinazolin-2-yl |
| 1.193 | 7-fluoroquinazolin-2-yl | 1.194 | 6-chloroquinazolin-2-yl |
| 1.195 | 7-chloroquinazolin-2-yl | 1.196 | 6-bromoquinazolin-2-y |
| 1.197 | 7-bromoquinazolin-2-yl | 1.198 | 6-trifluoromethylquinazolin-2-yl |
| 1.199 | 7-trifluoromethylquinazolin-2-yl | 1.200 | benzoxazol-2-yl |
| 1.201 | 5-fluorobenzoxazol-2-yl | 1.202 | 6-fluorobenzoxazol-2-yl |
| 1.203 | 5-chlorobenzoxazol-2-yl | 1.204 | 6-chlorobenzoxazol-2-yl |
| 1.205 | 5-bromobenzoxazol-2-yl | 1.206 | 6-bromobenzoxazol-2-yl |
| 1.207 | 5-trifluoromethylbenzoxazol-2-yl | 1.208 | 6-trifluoromethylbenzoxazol-2-yl |
| 1.209 | benzothiazol-2-yl | 1.210 | 5-fluorobenzothiazol-2-yl |
| 1.211 | 6-fluorobenzothiazol-2-yl | 1.212 | 5-chlorobenzothiazol-2-yl |
| 1.213 | 6-chlorobenzothiazol-2-yl | 1.214 | 5-bromobenzothiazol-2-yl |
| 1.215 | 6-bromobenzothiazol-2-yl | 1.216 | 5-trifluoromethylbenzothiazol-2-yl |
| 1.217 | 6-trifluoromethylbenzothiazol-2-yl | 1.218 | benzo[1,2,4]triazin-3-yl |
| 1.219 | 6-fluorobenzo[1,2,4]triazin-3-yl | 1.220 | 7-fluorobenzo[1,2,4]triazin-3-yl |
| 1.221 | 6-chlorobenzo[1,2,4]triazin-3-yl | 1.222 | 7-chlorobenzo[1,2,4]triazin-3-yl |
| 1.223 | 6-bromobenzo[1,2,4]triazin-3-yl | 1.224 | 7-bromo benzo[1,2,4]triazin-3-yl |
| 1.225 | 6-trifluoromethylbenzo[1,2,4]-triazin-3-yl | 1.226 | 7-trifluoromethylbenzo-[1,2,4]triazin-3-yl |

Table 2 covers compounds of the following type

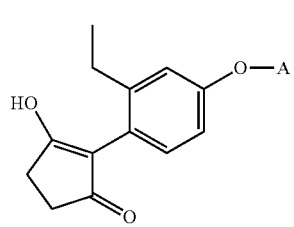

wherein A is as defined in Table 1.

Table 3 covers compounds of the following type

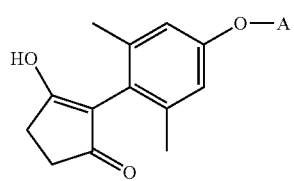

wherein A is as defined in Table 1.

Table 4 covers compounds of the following type

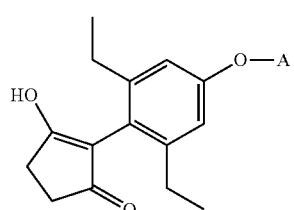

wherein A is as defined in Table 1.

Table 5 covers compounds of the following type

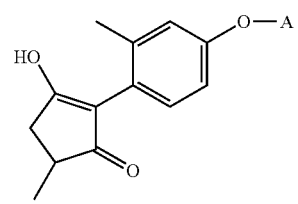

wherein A is as defined in Table 1.

Table 6 covers compounds of the following type

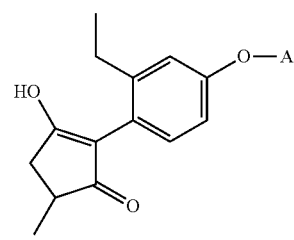

wherein A is as defined in Table 1.

Table 7 covers compounds of the following type

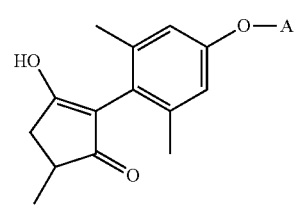

wherein A is as defined in Table 1.

Table 8 covers compounds of the following type

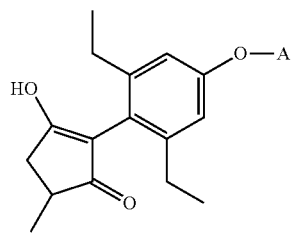

wherein A is as defined in Table 1.

Table 9 covers compounds of the following type

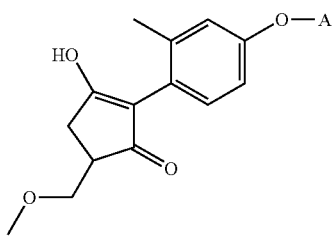

wherein A is as defined in Table 1.

Table 10 covers compounds of the following type

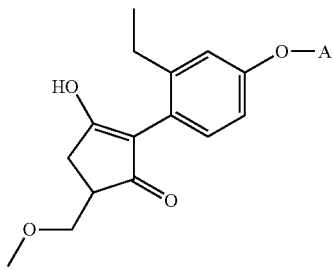

wherein A is as defined in Table 1.

Table 11 covers compounds of the following type

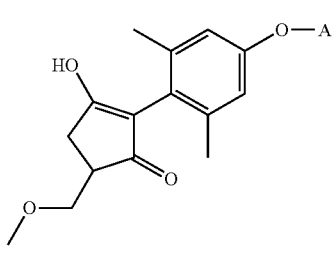

wherein A is as defined in Table 1.

Table 12 covers compounds of the following type

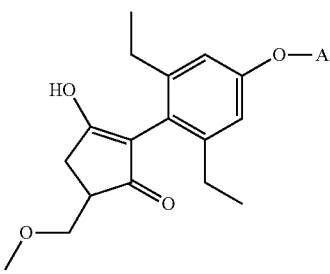

wherein A is as defined in Table 1.

Table 13 covers compounds of the following type

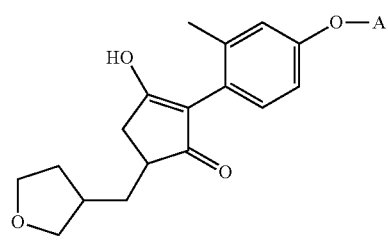

wherein A is as defined in Table 1.

Table 14 covers compounds of the following type

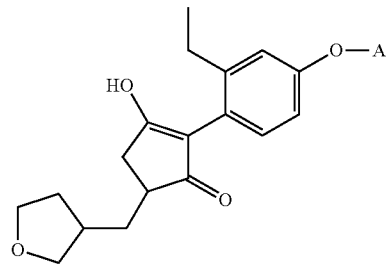

wherein A is as defined in Table 1.

Table 15 covers compounds of the following type

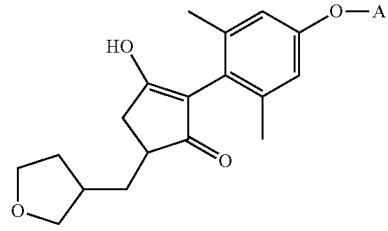

wherein A is as defined in Table 1.

Table 16 covers compounds of the following type

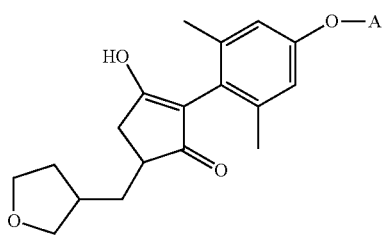

wherein A is as defined in Table 1.

Table 17 covers compounds of the following type

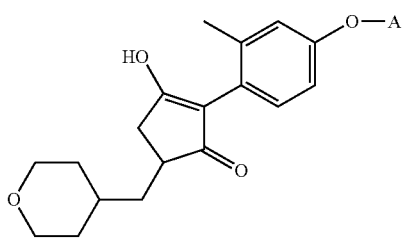

wherein A is as defined in Table 1.

Table 18 covers compounds of the following type

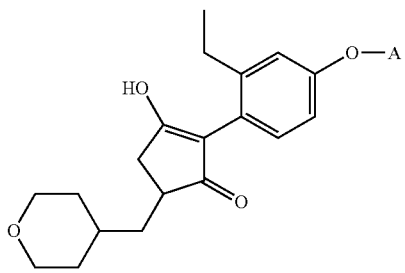

wherein A is as defined in Table 1.

Table 19 covers compounds of the following type

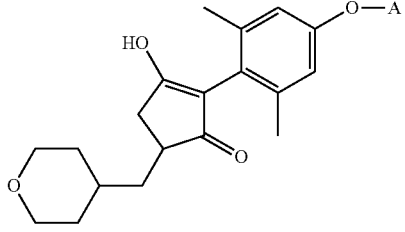

wherein A is as defined in Table 1.

Table 20 covers compounds of the following type

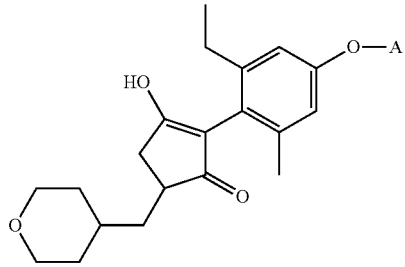

wherein A is as defined in Table 1.

Table 21 covers compounds of the following type

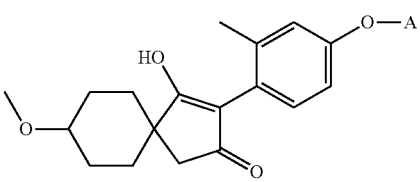

wherein A is as defined in Table 1.

Table 22 covers compounds of the following type

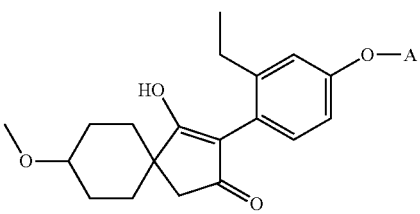

wherein A is as defined in Table 1.

Table 23 covers compounds of the following type

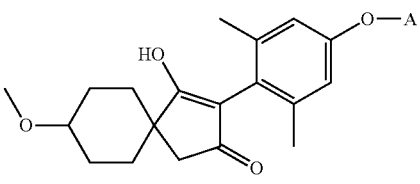

wherein A is as defined in Table 1.

Table 24 covers compounds of the following type

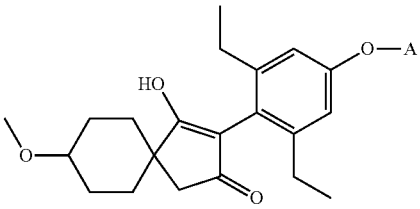

wherein A is as defined in Table 1.

Table 25 covers compounds of the following type

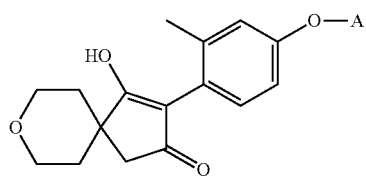

wherein A is as defined in Table 1.

Table 26 covers compounds of the following type

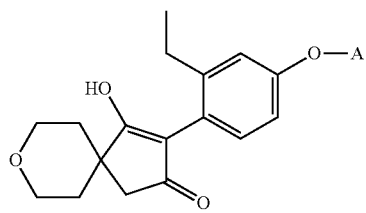

wherein A is as defined in Table 1.

Table 27 covers compounds of the following type

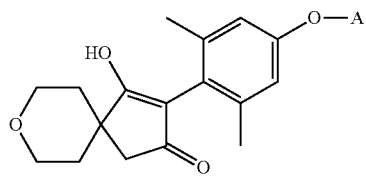

wherein A is as defined in Table 1.

Table 28 covers compounds of the following type

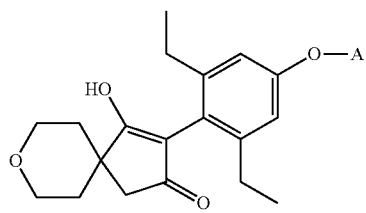

wherein A is as defined in Table 1.

Table 29 covers compounds of the following type

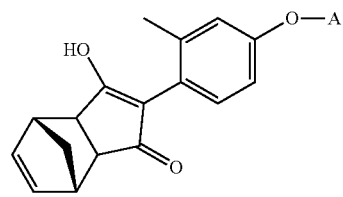

wherein A is as defined in Table 1.

Table 30 covers compounds of the following type

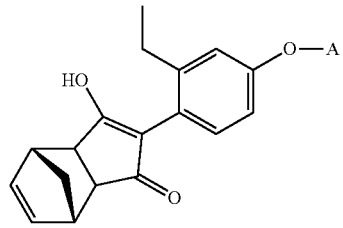

wherein A is as defined in Table 1.

Table 31 covers compounds of the following type

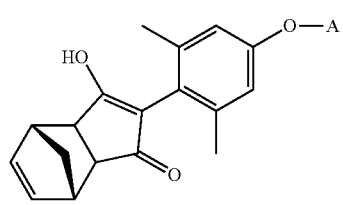

wherein A is as defined in Table 1.

Table 32 covers compounds of the following type

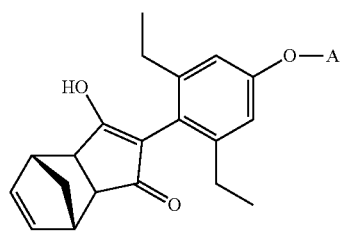

wherein A is as defined in Table 1.

Table 33 covers compounds of the following type

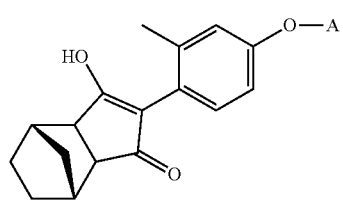

wherein A is as defined in Table 1.

Table 34 covers compounds of the following type

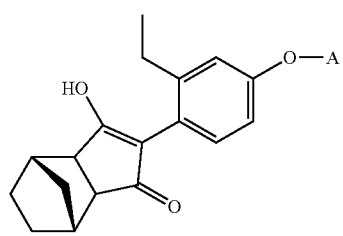

wherein A is as defined in Table 1.

Table 35 covers compounds of the following type

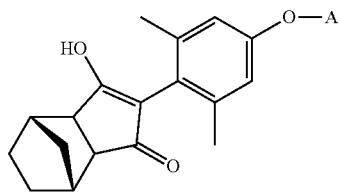

wherein A is as defined in Table 1.

Table 36 covers compounds of the following type

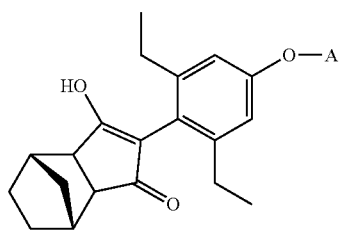

wherein A is as defined in Table 1.

Table 37 covers compounds of the following type

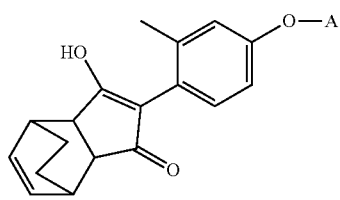

wherein A is as defined in Table 1.

Table 38 covers compounds of the following type

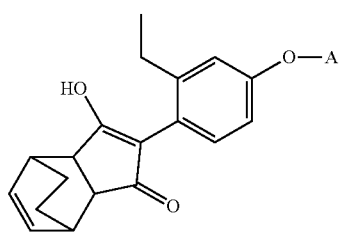

wherein A is as defined in Table 1.

Table 39 covers compounds of the following type

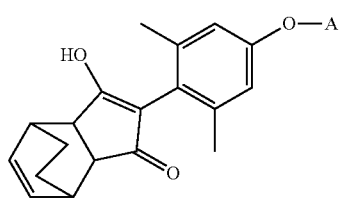

wherein A is as defined in Table 1.

Table 40 covers compounds of the following type

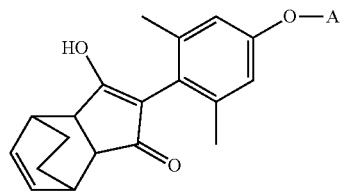

wherein A is as defined in Table 1.

Table 41 covers compounds of the following type

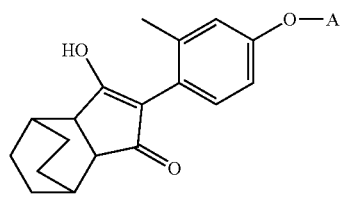

wherein A is as defined in Table 1.

Table 42 covers compounds of the following type

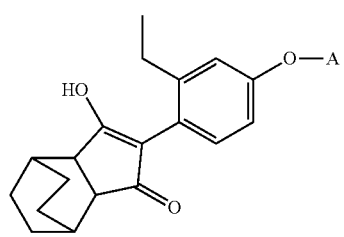

wherein A is as defined in Table 1.

Table 43 covers compounds of the following type

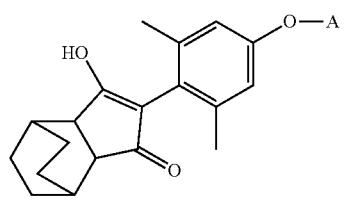

wherein A is as defined in Table 1.

Table 44 covers compounds of the following type

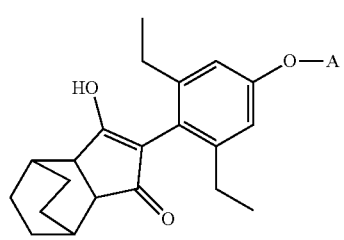

wherein A is as defined in Table 1.

93

Table 45 covers compounds of the following type

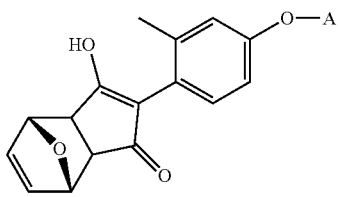

wherein A is as defined in Table 1.

Table 46 covers compounds of the following type

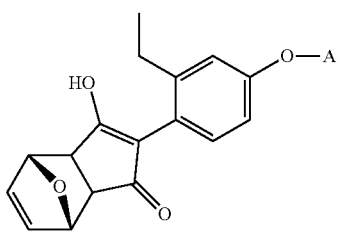

wherein A is as defined in Table 1.

Table 47 covers compounds of the following type

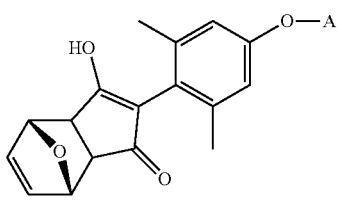

wherein A is as defined in Table 1.

Table 48 covers compounds of the following type

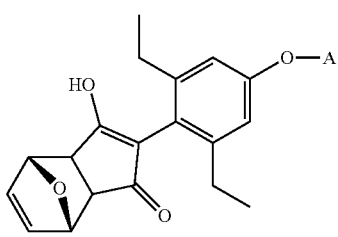

wherein A is as defined in Table 1.

Table 49 covers compounds of the following type

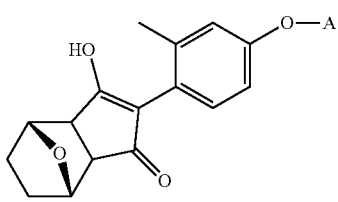

wherein A is as defined in Table 1.

94

Table 50 covers compounds of the following type

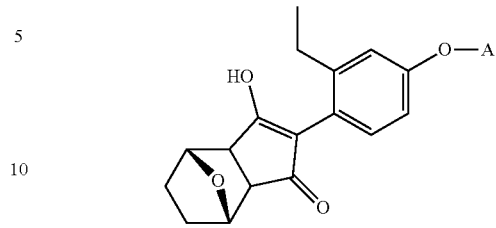

wherein A is as defined in Table 1.

Table 51 covers compounds of the following type

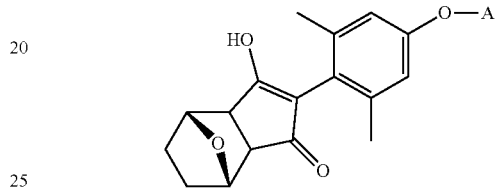

wherein A is as defined in Table 1.

Table 52 covers compounds of the following type

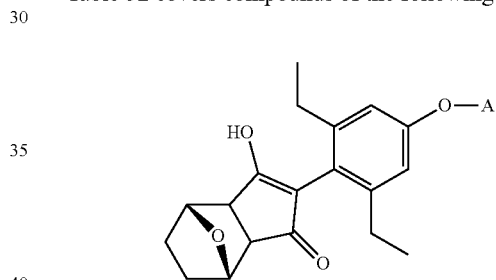

wherein A is as defined in Table 1.

Biological Examples

Seeds of a variety of test species were sown in standard soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

Test Plants:

*Lolium perenne* (LOLPE), *Alopecurus myosuroides* (ALOMY), *Echinochloa crus-galli* (ECHCG), and *Avena fatua* (AVEFA).

Pre-Emergence Activity

| Compound Number | Rate g/ha | LOLPE | ALOMY | ECHCG | AVEFA |
|---|---|---|---|---|---|
| A-1 | 250 | 20 | 20 | 30 | 0 |
| A-2 | 250 | 60 | 30 | 30 | 0 |
| A-3 | 250 | 80 | 80 | 90 | 30 |
| A-4 | 250 | 80 | 100 | 90 | 70 |
| A-5 | 250 | 50 | 40 | 60 | 30 |
| A-6 | 250 | 80 | 70 | 70 | 30 |
| A-7 | 250 | 90 | 70 | 100 | 90 |
| A-8 | 250 | 30 | 40 | 40 | 0 |
| A-9 | 250 | 60 | 20 | 50 | 0 |
| A-10 | 250 | 20 | 10 | 10 | 0 |
| A-11 | 250 | 100 | 90 | 70 | 90 |
| A-12 | 250 | 70 | 40 | 60 | 10 |
| A-13 | 250 | 60 | 60 | 70 | 0 |
| A-14 | 250 | 70 | 40 | 80 | 0 |
| A-15 | 250 | 90 | 60 | 70 | 70 |
| A-16 | 250 | 0 | 0 | 10 | 0 |
| A-17 | 250 | 0 | 0 | 30 | 0 |
| A-18 | 250 | 0 | 10 | 40 | 0 |
| A-19 | 250 | 0 | 0 | 10 | 0 |
| A-20 | 250 | 20 | 40 | 60 | 0 |
| A-21 | 250 | 30 | 10 | 50 | 0 |
| A-22 | 250 | 80 | 50 | 90 | 50 |
| A-23 | 250 | 90 | 30 | 90 | 20 |
| A-24 | 250 | 80 | 100 | 70 | 60 |
| A-25 | 250 | 80 | 40 | 70 | 30 |
| A-26 | 250 | 100 | 90 | 100 | 60 |
| A-32 | 250 | 10 | 0 | 50 | 0 |
| A-34 | 250 | 70 | 80 | 70 | 30 |
| A-35 | 250 | 0 | 0 | 70 | 0 |
| A-37 | 250 | 0 | 10 | 90 | 10 |
| A-38 | 250 | 70 | 80 | 100 | 0 |
| P-3 | 250 | 90 | 100 | 100 | 90 |
| P-4 | 250 | 90 | 80 | 100 | 70 |

Post-Emergence Activity

| Compound Number | Rate g/ha | LOLPE | ALOMY | ECHCG | AVEFA |
|---|---|---|---|---|---|
| A-1 | 250 | 70 | 70 | 100 | 80 |
| A-2 | 250 | 80 | 90 | 100 | 90 |
| A-3 | 250 | 90 | 100 | 100 | 90 |
| A-4 | 250 | 100 | 100 | 100 | 90 |
| A-5 | 250 | 70 | 60 | 90 | 50 |
| A-6 | 250 | 70 | 90 | 90 | 70 |
| A-7 | 250 | 100 | 100 | 100 | 90 |
| A-8 | 250 | 80 | 80 | 90 | 40 |
| A-9 | 250 | 60 | 60 | 90 | 40 |
| A-10 | 250 | 30 | 10 | 40 | 0 |
| A-11 | 250 | 90 | 90 | 100 | 90 |
| A-12 | 250 | 70 | 80 | 100 | 70 |
| A-13 | 250 | 60 | 80 | 50 | 30 |
| A-14 | 250 | 70 | 70 | 80 | 30 |
| A-15 | 250 | 90 | 90 | 100 | 90 |
| A-16 | 250 | 0 | 30 | 60 | 0 |
| A-17 | 250 | 10 | 10 | 40 | 10 |
| A-18 | 250 | 10 | 30 | 70 | 30 |
| A-19 | 250 | 0 | 10 | 60 | 10 |
| A-20 | 250 | 30 | 50 | 70 | 20 |
| A-21 | 250 | 0 | 10 | 70 | 0 |
| A-22 | 250 | 100 | 100 | 90 | 100 |
| A-23 | 250 | 50 | 60 | 70 | 80 |
| A-24 | 250 | 90 | 80 | 90 | 80 |
| A-25 | 250 | 80 | 90 | 70 | 70 |
| A-26 | 250 | 100 | 100 | 90 | 70 |
| A-32 | 250 | 0 | 0 | 0 | 0 |
| A-34 | 250 | 70 | 80 | 80 | 60 |
| A-35 | 250 | 20 | 0 | 80 | 0 |
| A-37 | 250 | 40 | 50 | 80 | 60 |
| A-38 | 250 | 80 | 90 | 100 | 80 |
| P-3 | 250 | 100 | 90 | 100 | 100 |
| P-4 | 250 | 70 | 90 | 90 | 60 |

What is claimed is:

1. A compound of formula I

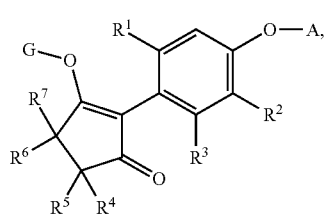

wherein

A is a mono- or bicyclic aryl or heteroaryl which contains a heteroatom selected from nitrogen, oxygen and sulfur, and which is unsubstituted or substituted;

$R^1$ is methyl, ethyl, n-propyl, isopropyl, cyclopropyl, halomethyl, haloethyl, vinyl, propenyl, ethynyl, propynyl, halogen, methoxy, ethoxy, halomethoxy or haloethoxy;

$R^2$ and $R^3$ are independently of each other hydrogen, methyl, ethyl, n-propyl, isopropyl, cyclopropyl, halomethyl, haloethyl, vinyl, propenyl, ethynyl, propynyl, halogen, methoxy, ethoxy, halomethoxy or haloethoxy; and $R^4$, $R^5$, $R^6$, and $R^7$ are independently of each other hydrogen, halogen, optionally substituted $C_1$-$C_6$alkyl, optionally substituted $C_3$-$C_7$cycloalkyl, optionally substituted $C_2$-$C_6$ alkenyl, optionally substituted $C_5$-$C_7$cycloalkenyl, optionally substituted $C_2$-$C_6$alkynyl, optionally substituted $C_1$-$C_6$ alkoxy, optionally substituted $C_3$-$C_7$cycloalkyloxy, optionally substituted $C_1$-$C_6$alkylthio, optionally substituted $C_1$-$C_6$alkylsulfinyl, optionally substituted $C_1$-$C_6$alkylsulfonyl, optionally substituted aryl, optionally substituted aryloxy, optionally substituted arylthio, optionally substituted arylsulfinyl, optionally substituted arylsulfonyl, optionally substituted heterocyclyl, optionally substituted heterocyclyloxy, optionally substituted heterocyclylthio, optionally substituted heterocyclylsulfinyl, optionally substituted heterocyclylsulfonyl, optionally substituted heteroaryl, optionally substituted heteroaryloxy, optionally substituted heteroarylthio, optionally substituted heteroarylsulfinyl, optionally substituted heteroarylsulfonyl, cyano or amino;

or $R^4$ and $R^5$, or $R^6$ and $R^7$, together with the atoms to which they are bonded, form an optionally substituted saturated or unsaturated carbocyclyl or heterocyclyl which contains one or two heteroatoms selected from nitrogen, oxygen and sulfur;

or $R^5$ and $R^6$, together with the atoms to which they are bonded, form an optionally substituted saturated or unsaturated carbocyclyl or heterocyclyl which contains one or two heteroatoms selected from nitrogen, oxygen and sulfur, and which carbocyclyl may further be bridged by optionally substituted $C_1$-$C_2$ alkyldiyl or by oxygen; and G is hydrogen or an agriculturally acceptable metal, sulfonium, ammonium or latentiating group;

and wherein, when G is a latentiating group, then G is phenyl$C_1$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$alkenyl, $C_3$haloalkenyl, $C_3$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$;

wherein $X^a$, $X^b$, $X^c$, $X^d$, $X^e$ and $X^f$ are independently of each other oxygen or sulfur; and wherein $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$haloalkyl, $C_2$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_8$-trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; or $C_3$-$C_7$cycloalkylamino, di-$C_3$-$C_7$cycloalkylamino or $C_3$-$C_7$cycloalkoxy;

or $R^c$ and $R^d$ are joined together to form a 3-7 membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$haloalkyl, $C_2$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl,
$C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$) alkylcarbonyl-N—($C_1$-$C_5$)alkylamino($C_1$-$C_5$)alkyl, $C_3$-$C_8$-trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino ($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$) alkyl, $C_3$-$C_5$alkenyloxy($C_1$-$C_5$)alkyl, $C_3$-$C_5$alkynyloxy ($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl ($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$) alkylcarbonyl-N—($C_2$-$C_5$)alkylaminoalkyl, $C_3$-$C_6$-trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_8$dialkylamino; or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$ aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy ($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$) alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

and wherein:

"aryl" means phenyl or naphthyl;

"heteroaryl" means an aromatic ring system containing at least one heteroatom and consisting either of a single ring or of two fused rings; and "heterocyclyl" means a non-aromatic monocyclic or bicyclic ring system containing up to 7 atoms including one or two heteroatoms selected from O, S and N;

and wherein:

when present, the optional substituents on an alkyl moiety, either alone or as part of a larger group, are one or more of halogen, nitro, cyano, $C_3$-$C_7$cycloalkyl (itself optionally substituted with $C_1$-$C_6$alkyl or halogen), $C_5$-$C_7$cycloalkenyl (itself optionally substituted with $C_1$-$C_4$alkyl or halogen), hydroxy, $C_1$-$C_{10}$ alkoxy, $C_1$-$C_{10}$ alkoxy($C_1$-$C_{10}$)alkoxy, tri($C_1$-$C_4$)alkylsilyl($C_1$-$C_6$) alkoxy, $C_1$-$C_6$alkoxy-carbonyl($C_1$-$C_{10}$)alkoxy, $C_1$-$C_{10}$haloalkoxy, aryl($C_1$-$C_4$)alkoxy (where the aryl group is optionally substituted), $C_3$-$C_7$cycloalkyloxy (where the cycloalkyl group is optionally substituted with $C_1$-$C_6$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio (where the aryl group is optionally substituted), $C_3$-$C_7$cycloalkylthio (where the cycloalkyl group is optionally substituted with $C_1$-$C_6$alkyl or halogen), tri ($C_1$-$C_4$)alkylsilyl($C_1$-$C_6$)alkylthio, arylthio (where the aryl group is optionally substituted), $C_1$-$C_6$alkylsulfonyl, $C_1$-$C_6$haloalkylsulfonyl, $C_1$-$C_6$alkylsulfinyl, $C_1$-$C_6$haloalkylsulfinyl, arylsulfonyl (where the aryl group is optionally substituted), tri ($C_1$-$C_4$)alkylsilyl, aryldi($C_1$-$C_4$)alkylsilyl, ($C_1$-$C_4$)alkyldiarylsilyl, triarylsilyl, aryl($C_1$-$C_4$)alkylthio($C_1$-$C_4$) alkyl, aryloxy($C_1$-$C_4$)alkyl, formyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$ alkyl)aminocarbonyl, N—($C_1$-$C_3$alkyl)-N—($C_1$-$C_3$ alkoxy)aminocarbonyl, $C_1$-$C_6$alkylcarbonyloxy, arylcarbonyloxy (where the aryl group is optionally substituted), di($C_1$-$C_6$)alkylaminocarbonyloxy, $C_1$-$C_6$alkyliminooxy, $C_3$-$C_6$alkenyloxyimino, aryloxyimino, aryl (itself optionally substituted), heteroaryl (itself optionally substituted), heterocyclyl (itself optionally substituted with $C_1$-$C_6$alkyl or halogen), aryloxy (where the aryl group is optionally substituted), heteroaryloxy (where the heteroaryl group is optionally substituted), heterocyclyloxy (where the heterocyclyl group is optionally substituted with $C_1$-$C_6$alkyl or halogen), amino, $C_1$-$C_6$alkylamino, di($C_1$-$C_6$)alkylamino, $C_1$-$C_6$alkylcarbonylamino, N—($C_1$-$C_6$)alkylcarbonyl-N—($C_1$-$C_6$)alkylamino, $C_2$-$C_6$alkenylcarbonyl, $C_2$-$C_6$alkynylcarbonyl, $C_3$-$C_6$alkenyloxycarbonyl, $C_3$-$C_6$alkynyloxycarbonyl, aryloxycarbonyl (where the aryl group is optionally substituted), or arylcarbonyl (where the aryl group is optionally substituted);

when present, the optional substituents on alkenyl or alkynyl are the optional substituents as defined for an alkyl moiety;

when present, the optional substituents on heterocyclyl are $C_1$-$C_6$alkyl or $C_1$-$C_6$haloalkyl or are the optional substituents as defined for an alkyl moiety;

when present, the optional substituents on cycloalkyl or cycloalkenyl are $C_1$-$C_3$alkyl or are the optional substituents as defined for an alkyl moiety;

and when present, the optional substituents on aryl, heteroaryl or carbocycles are selected, independently, from halogen, nitro, cyano, rhodano, isothiocyanato, $C_1$-$C_6$alkyl, $C_1$-$C_6$haloalkyl, $C_1$-$C_6$alkoxy($C_1$-$C_6$)alkyl, $C_2$-$C_6$alkenyl, $C_2$-$C_6$haloalkenyl, $C_2$-$C_6$alkynyl, $C_3$-$C_7$cycloalkyl (itself optionally substituted with $C_1$-$C_6$alkyl or halogen), $C_{5-7}$cycloalkenyl (itself optionally substituted with $C_1$-$C_6$alkyl or halogen), hydroxy, $C_1$-$C_{10}$alkoxy, $C_1$-$C_{10}$alkoxy($C_1$-$C_{10}$)alkoxy, tri($C_1$-$C_4$) alkylsilyl($C_1$-$C_6$)alkoxy, $C_1$-$C_6$alkoxycarbonyl($C_1$-$C_{10}$)alkoxy, $C_1$-$C_{10}$haloalkoxy, aryl($C_1$-$C_4$)alkoxy (where the aryl group is optionally substituted with halogen or $C_1$-$C_6$alkyl), $C_3$-$C_7$cycloalkyloxy (where the cycloalkyl group is optionally substituted with $C_1$-$C_6$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio, $C_3$-$C_7$cycloalkylthio (where the cycloalkyl group is optionally substituted with $C_1$-$C_6$alkyl or halogen), tri ($C_1$-$C_4$)-alkylsilyl($C_1$-$C_6$)alkylthio, arylthio, $C_1$-$C_6$alkylsulfonyl, $C_1$-$C_6$haloalkylsulfonyl, $C_1$-$C_6$alkylsulfinyl, $C_1$-$C_6$haloalkylsulfinyl, arylsulfonyl, tri($C_1$-$C_4$)alkylsilyl, aryldi($C_1$-$C_4$)alkylsilyl, $C_1$-$C_4$alkyldiarylsilyl, triarylsilyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$alkyl)-aminocarbonyl, N—($C_1$-$C_3$ alkyl)-N—($C_1$-$C_3$alkoxy)aminocarbonyl, $C_1$-$C_6$alkylcarbonyloxy, arylcarbonyloxy, di($C_1$-$C_6$)alkylaminocarbonyloxy, aryl (itself optionally substituted with $C_1$-$C_6$alkyl or halogen), heteroaryl (itself optionally substituted with $C_1$-$C_6$alkyl or halogen), heterocyclyl (itself optionally substituted with $C_1$-$C_6$alkyl or halogen), aryloxy (where the aryl group is optionally substituted with $C_1$-$C_6$alkyl or halogen), heteroaryloxy (where the heteroaryl group is optionally substituted with $C_1$-$C_6$alkyl or halogen), heterocyclyloxy (where the heterocyclyl group is optionally substituted with $C_1$-$C_6$alkyl or halogen), amino, $C_1$-$C_6$alkylamino, di($C_1$-$C_6$)alkylamino, $C_1$-$C_6$alkylcarbonylamino, N—($C_1$-$C_6$)alkylcarbonyl-N—($C_1$-$C_6$)alkylamino, and arylcarbonyl (where the aryl group is itself optionally substituted with halogen or $C_1$-$C_6$alkyl);

or two adjacent positions on an aryl or heteroaryl system are cyclised to form a 5, 6 or 7 membered carbocyclic or heterocyclic ring, itself optionally substituted with halogen or $C_1$-$C_6$alkyl.

2. A compound according to claim 1, wherein A is phenyl, naphthyl, a 5- or a 6-membered heteroaryl or a bicyclic 8- to 10-membered heteroaryl.

3. A compound according to claim 1, wherein A is substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro, cyano, $C_3$-$C_6$cycloalkyl, $C_1$-$C_3$alkylcarbonyl, $C_1$-$C_4$alkoxycarbonyl, aminocarbonyl, $C_1$-$C_3$alkylaminocarbonyl, di-$C_1$-$C_3$alkylaminocarbonyl, $C_1$-$C_3$alkylaminocarbonyloxy, di-$C_1$-$C_3$alkylaminocarbonyloxy, aminothiocarbonyl, $C_1$-$C_3$alkylaminothiocarbonyl, di$C_1$-$C_3$alkylaminothiocarbonyl, $C_1$-$C_4$alkylcarbonylamino, $C_3$-$C_6$cycloalkylcarbonylamino, $C_1$-$C_4$alkoxycarbonylamino, $C_1$-$C_4$alkylthiocarbonylamino, $C_1$-$C_3$alkoxy$C_1$-$C_3$alkyl, $C_1$-$C_6$alkylthio$C_1$-$C_6$alkyl, $C_1$-$C_6$alkylsulfinyl$C_1$-$C_6$alkyl, $C_1$-$C_6$alkylsulfonyl$C_1$-$C_6$alkyl, $C_1$-$C_3$alkylsulfonyloxy, $C_1$-$C_3$haloalkylsulfonyloxy or di$C_1$-$C_6$alkylaminosulfonyl, or 2 substituents on adjacent carbon atoms of A together form a $C_3$-$C_4$alkylene, wherein 1 or 2 methylene groups are optionally substituted by halogen, or wherein 1 or 2 of these methylene groups are replaced by oxygen.

4. A compound according to claim 2, wherein A is phenyl, naphthyl, pyridyl, pyrazinyl, pyrimidinyl, pyridazinyl, benzothiazolyl, benzoxazolyl, cinnolinyl, quinolinyl, quinazolinyl, quinoxalinyl or benzotriazinyl, in each case substituted by halogen, methyl, ethyl, trifluoromethyl, methoxy, difluoromethoxy, trifluoromethoxy, nitro or cyano.

5. A compound according to claim 1 wherein $R^1$ is methyl, ethyl, n-propyl, cyclopropyl, halogen, halomethoxy or haloethoxy.

6. A compound according to claim 5, wherein $R^1$ is methyl or ethyl.

7. A compound according to claim 1, wherein $R^2$ is hydrogen, methyl or halogen.

8. A compound according to claim 7, wherein $R^2$ is hydrogen.

9. A compound according to claim 1, wherein $R^3$ is hydrogen, methyl, ethyl, n-propyl, cyclopropyl, halogen, halomethoxy or haloethoxy.

10. A compound according to claim 9, wherein $R^3$ is hydrogen, methyl or ethyl.

11. A compound according to claim 1, wherein $R^4$, $R^5$, $R^6$ and $R^7$ are independently of each other hydrogen, $C_1$-$C_6$alkyl, $C_1$-$C_4$haloalkyl, $C_1$-$C_4$alkoxy$C_1$-$C_4$alkyl, optionally substituted five- or six-membered heterocyclyl, or optionally substituted five- or six-membered heterocyclyl$C_1$-$C_2$alkyl;

or $R^4$ and $R^5$, or $R^6$ and $R^7$, together with the atoms to which they are bonded, form an optionally substituted saturated or unsaturated five- or six-membered carbocyclyl or heterocyclyl which contains one or two oxygen atoms;

or $R^5$ and $R^6$, with the atoms to which they are bonded, form an optionally substituted five- or six-membered saturated or unsaturated carbocyclyl which is optionally bridged by $C_1$-$C_2$ alkyldiyl or by oxygen.

12. A compound according to claim 11, wherein $R^4$ and $R^7$ are hydrogen and $R^5$ and $R^6$, with the atoms to which they are bonded, form a six-membered saturated or unsaturated carbocyclyl which is bridged by $C_1$-$C_2$ alkyldiyl or by oxygen.

13. A compound according to claim 1, wherein "aryl" means phenyl.

14. A compound according to claim 1, wherein, when G is a latentiating group, then G is a group —C($X^a$)—$R^a$ or —C($X^b$)—$X^c$—$R^b$, and the meanings of $X^a$, $R^a$, $X^b$, $X^c$ and $R^b$ are as defined in claim 1.

15. A compound according to claim 1, wherein G is hydrogen, an alkali metal or an alkaline earth metal.

16. A process for the preparation of a compound of formula I according to claim 1, wherein G is hydrogen, which comprises reacting a compound of formula (BB)

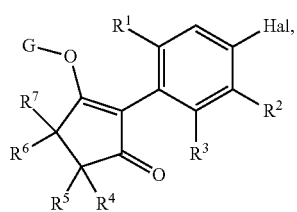

(BB)

wherein Hal is bromine or iodine and $R^1$ to $R^7$ are as defined in claim 1, with a compound A-OH, wherein A is as defined in claim 1, in the presence of a catalyst, a ligand or additive, a base and a solvent.

17. A process for the preparation of a compound of formula I according to claim 1, wherein G is hydrogen, which comprises reacting a compound of formula (DD)

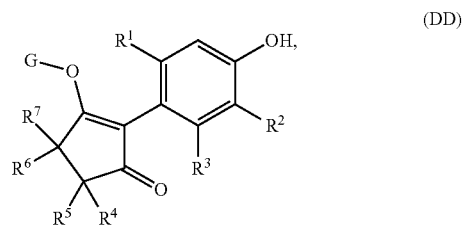

(DD)

wherein $R^1$ to $R^7$ are as defined in claim 1, with a compound A-Hal, wherein A is as defined in claim 1 and Hal is fluorine, chlorine, bromine or iodine, in the presence of a base and a solvent, and in the presence or absence of a catalyst and a ligand.

18. A process for the preparation of a compound of formula I according to claim 1, wherein G is hydrogen and $R^5$ and $R^6$, together with the atoms to which they are bonded, form an optionally substituted unsaturated carbocyclyl which is further bridged by optionally substituted $C_1$-$C_2$ alkyldiyl or oxygen, which comprises reacting a compound of formula (M)

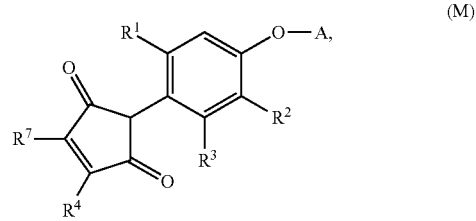

(M)

with a compound of formula (O)

(O)

wherein W is optionally substituted $C_1$-$C_2$ alkyldiyl or oxygen, and $R_b$ is hydrogen or a substituent suitable for preparing the compound of formula I, in the presence of a catalyst and a solvent.

19. A compound of formula (M)

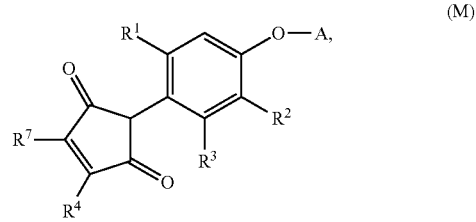

(M)

wherein A, $R^1$ to $R^4$ and $R^7$ are as defined in claim 1.

20. A herbicidal composition, which, in addition to comprising formulation adjuvants, comprises a herbicidally effective amount of a compound of formula I as defined in claim 1.

21. A herbicidal composition according to claim 20, which, in addition to comprising formulation adjuvants, comprises a herbicidally effective amount of the compound of formula I as defined in claim 1, a further herbicide, and optionally a safener.

22. A herbicidal composition according to claim 21, which, in addition to comprising formulation adjuvants, comprises a herbicidally effective amount of the compound of formula I as defined in claim 1, a safener, and optionally a further herbicide.

23. A method of controlling grasses and weeds in crops of useful plants, which comprises applying a herbicidally effective amount of a compound of formula I as defined in claim 1, or of a composition comprising such a compound, to the plants or to the locus thereof.

24. A method according to claim 23, which comprises applying a herbicidally effective amount of the composition comprising the compound to the plants or to the locus thereof, and wherein the crops of useful plants are cereals, rice, corn, rape, sugarbeet, sugarcane, soybean, cotton, sunflower, peanut or plantation crops.

25. A mixture of a compound of formula I, as defined in claim 1, in combination with a further herbicide, wherein the mixture of the compound of formula I is selected from:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester, compound of formula I+4-[(4,5-dihydro-3-methoxy-4-methyl-5-oxo)-1H-1,2,4-triazol-1-ylcarbonylsulfamoyl]-5-methylthiophene-3-carboxylic acid, compound of formula I+BAY747 as defined by Chemical Abstracts Service Registry Number 335104-84-2, compound of formula I+topramezone, compound of formula I+4-hydroxy-3-[[2[(2-methoxyethoxy)methyl]-6-(trifluoro-methyl)-3-pyridinyl]carbonyl]-bicyclo[3.2.1]oct-3-en-2-one, and compound of formula I+4-hydroxy-3-[[2-(3-methoxypropyl)-6-(difluoromethyl)-3-pyridinyl]carbonyl]bicyclo[3.2.1]oct-3-en-2-one;

and wherein the mixture partner for the compound of formula I is optionally in the form of an ester or a salt.

* * * * *